(12) United States Patent
Bhowmick et al.

(10) Patent No.: US 12,138,419 B2
(45) Date of Patent: *Nov. 12, 2024

(54) PERFUSION SYSTEM

(71) Applicant: Sun Pharmaceutical Industries Ltd., Mumbai (IN)

(72) Inventors: Subhas Balaram Bhowmick, Baroda (IN); Prashant Kane, Baroda (IN); Samarth Kumar, Baroda (IN); Kirti Ganorkar, Baroda (IN)

(73) Assignee: Sun Pharmaceutical Industries Ltd., Mumbai (IN)

( * ) Notice: Subject to any disclaimer, the term of this patent is extended or adjusted under 35 U.S.C. 154(b) by 54 days.

This patent is subject to a terminal disclaimer.

(21) Appl. No.: 18/057,595

(22) Filed: Nov. 21, 2022

(65) Prior Publication Data

US 2023/0158226 A1 May 25, 2023

Related U.S. Application Data

(63) Continuation of application No. 16/075,791, filed as application No. PCT/IN2017/050055 on Feb. 9, 2017, now Pat. No. 11,554,207.

(30) Foreign Application Priority Data

Feb. 9, 2016 (IN) .............................. 201621004576

(51) Int. Cl.
*A61M 5/14* (2006.01)
*A61K 9/00* (2006.01)
*A61M 5/168* (2006.01)

(52) U.S. Cl.
CPC ............. *A61M 5/14* (2013.01); *A61K 9/0019* (2013.01); *A61M 5/1407* (2013.01); *A61M 5/16827* (2013.01); *A61M 2205/6009* (2013.01)

(58) Field of Classification Search
CPC ...................... A61M 5/1408; A61M 5/16827
See application file for complete search history.

(56) References Cited

U.S. PATENT DOCUMENTS

| 4,447,230 A | 5/1984 | Gula et al. |
| 4,872,553 A | 10/1989 | Suzuki et al. |

(Continued)

FOREIGN PATENT DOCUMENTS

| CN | 102824345 A | 12/2012 |
| CN | 102885765 B | 11/2013 |

(Continued)

OTHER PUBLICATIONS

Dodds, H.M., et al., Photodegradation of Irinotecan (CPT-11) in Aqueous Solutions; Identification of Fluorescent Products and Influence of Solution Composition, J Pharm Sci, 86(12), pp. 1410-1416 (1997).

(Continued)

*Primary Examiner* — Emily L Schmidt
(74) *Attorney, Agent, or Firm* — Blank Rome LLP

(57) ABSTRACT

A perfusion container for directly administering to patients a dose of an antineoplastic drug calculated according to a patient's parameter, wherein the first perfusion container comprises a solution of antineoplastic drug at a concentration and volume such that the amount of antineoplastic drug in the container is equal to the calculated dose for one patient but less than the calculated dose for a second patient, the calculated dose is provided to first patient within 5% variance by directly administering the full volume of the solution of antineoplastic drug from the first perfusion container, further the first perfusion container is accompanied by a second top-up perfusion container comprising a solution of antineoplastic drug at a concentration and volume such that the calculated dose is provided within 5% variance by directly administering the full volume of the solution of (Continued)

antineoplastic drug from the first perfusion container and the second top-up container to the second patient.

20 Claims, 2 Drawing Sheets

(56) References Cited

U.S. PATENT DOCUMENTS

| | | | |
|---|---|---|---|
| 5,609,572 | A | 3/1997 | Lang |
| 5,786,344 | A | 7/1998 | Ratain et al. |
| 5,896,989 | A | 4/1999 | Ropiak et al. |
| 6,403,569 | B1 | 6/2002 | Achterrath |
| 6,673,805 | B2 | 1/2004 | Lauria et al. |
| 6,771,697 | B1 | 8/2004 | Goldstein et al. |
| 6,794,370 | B2 | 9/2004 | Achterrath |
| 7,235,583 | B1 | 6/2007 | Webb et al. |
| 7,352,770 | B1 | 4/2008 | Yonge et al. |
| 7,479,499 | B2 | 1/2009 | Govindarajan et al. |
| 7,490,639 | B2 | 2/2009 | Py |
| 7,932,241 | B2 | 4/2011 | Glausch et al. |
| 7,992,597 | B2 | 8/2011 | Py et al. |
| 8,529,520 | B2 | 9/2013 | Daniel |
| 9,241,948 | B2 | 1/2016 | Kumar et al. |
| 9,463,193 | B2 | 10/2016 | Gamelin et al. |
| 10,022,365 | B2 | 7/2018 | Tong et al. |
| 10,098,813 | B2 | 10/2018 | Kumar et al. |
| 11,253,642 | B2 | 2/2022 | Bhowmick et al. |
| 11,554,207 | B2 | 1/2023 | Bhowmick et al. |
| 2002/0176509 | A1 | 11/2002 | Gatherer et al. |
| 2003/0031240 | A1 | 2/2003 | Redfern et al. |
| 2003/0039306 | A1 | 2/2003 | Redfern |
| 2004/0220546 | A1 | 11/2004 | Heruth et al. |
| 2008/0009788 | A1 | 1/2008 | Hunter et al. |
| 2008/0242691 | A1 | 10/2008 | Nakazawa et al. |
| 2008/0243691 | A1 | 10/2008 | Malcolm |
| 2009/0177188 | A1 | 7/2009 | Steinkogler |
| 2009/0221622 | A1 | 9/2009 | Teja et al. |
| 2010/0111941 | A1 | 5/2010 | Deitcher et al. |
| 2011/0004187 | A1 | 1/2011 | Beiriger |
| 2011/0177161 | A1 | 7/2011 | Nekkanti et al. |
| 2012/0323212 | A1 | 12/2012 | Murphy et al. |
| 2013/0333796 | A1 | 12/2013 | Py |
| 2014/0005135 | A1 | 1/2014 | Prestrelski et al. |
| 2014/0005603 | A1 | 1/2014 | Holtwick et al. |
| 2015/0045289 | A1 | 2/2015 | West et al. |
| 2019/0046398 | A1 | 2/2019 | Kumar et al. |
| 2021/0100947 | A1 | 4/2021 | Bhowmick et al. |
| 2023/0087099 | A1 | 3/2023 | Kumar et al. |

FOREIGN PATENT DOCUMENTS

| | | |
|---|---|---|
| CN | 103989624 A | 8/2014 |
| CN | 103990201 A | 8/2014 |
| JP | 2004166847 A | 6/2004 |
| JP | 4787455 B2 | 7/2011 |
| JP | 2011250726 A | 12/2011 |
| JP | 2012531953 A | 12/2012 |
| KR | 20050044689 A | 5/2005 |
| KR | 20100044927 A | 4/2010 |
| WO | 2009111294 A1 | 9/2009 |
| WO | 2015006822 A1 | 1/2015 |

OTHER PUBLICATIONS

International Preliminary Report on Patentability (IPRP) for International Patent Application No. PCT/IN2016/050429, Jun. 8, 2018.
International Search Report (ISR) for International Patent Application No. PCT/IN2016/050429, Apr. 4, 2017.
Janssen Pharmaceuticals, Ortho Tri-Cylen Tablets Prescription Package Insert (2013).
Japanese Application No. 2015174012 Office Action Mailed May 15, 2020, 3 Pages.
Japanese Application No. 2018-541407, Office Action Mailed Dec. 15, 2020, pp. 1-8.
Li W Y, et al., Stability of Irinotecan Hyrochloride in Aqueous Solutions, Am J Health Syst Pharm. vol. 55, pp. 539-544 (2002).
Taiwan Application No. 104129237 Office Action Mailed Jan. 15, 2020 ,9 Pages.
Thiesen J et al., Physicochemical Stability of Irinotecan Injection Concentrate and Diluted Infusion Solutions in PVC Bags, J Oncol Phar Pract., vol. 6 (3) 115-121 (2001).
Van Riel, Jmgh, et al., Continuous Infusion of Hepatic Arterial Irinotecan in Pretreated Patients With Colorectal Canceer Metastatic to the Liver, Ann Oncol, 15, pp. 59-63, 2004.
International Search Report for PCT/IN2017/050055 dated Jul. 7, 2017 [PCT/ISA/210].
U.S. Appl. No. 17/933,593, filed Sep. 20, 2022.
"Data Sheet Gemcitabine Ebewe", [retrieved from internet on Aug. 30, 2024]. Retrieved from <https://web.archive.org/web/20160125164326/http://www.medsafe.govt.nz/profs/Datasheet/g/GemcitabineEbeweinj.pdf>. Jan. 26, 2016.
"Erbitux Highlights of Prescribing Information", [retrieved from internet on Aug. 30, 2024]. Retrieved from <https://web.archive.org/web/20150701215111/http://pi.lilly.com/us/erbitux-uspi.pdf>. Jul. 1, 2015 *Documents found in an original search.

PERFUSION SYSTEM

CROSS REFERENCE TO RELATED APPLICATIONS

This application is a continuation of U.S. Nonprovisional Application No. 16/075,791 filed Aug. 6, 2018, which is a nationals stage of International Patent Application No. PCT/IN2017/050055 filed Feb. 9, 2017, which claims the benefit of India Application No. 201621004576 filed Feb. 9, 2016.

FIELD OF THE INVENTION

The present invention relates to a perfusion system for directly administering to patients in need thereof a dose of an antineoplastic drug calculated according to a patient parameter.

BACKGROUND OF THE INVENTION

There are certain drawbacks associated with most of the commercially available parenteral dosage forms of antineoplastic drugs. For instance, the commercially available parenteral dosage forms are available as vial products having either lyophilized powder of drug or concentrated solutions which cannot be directly administered to a patient; rather they require manipulation.

Particularly, in case of lyophilized compositions, in addition to the requirement of reconstitution of the freeze dried powder, its manufacturing process is itself very complicated and expensive. Further, when the composition is in the form of a concentrated solution, there is an additional step of dilution prior to administration. These difficulties only multiply, when the dose of the drug is to be delivered in terms of the patient parameter, such as body surface area, renal clearance, in which cases the dose needs to be accurately calculated and dilution and/or reconstitutions need to be done taking care of the precision aspect of the dose of the drug. While attempting to deliver the accurate dose of the drug, surplus volume of reconstituted or diluted solution may be required or withdrawal of the volume may be required. These additional steps may provide a threat or risk of contamination or loss of sterility etc. or exposure of the cytotoxic drug to the involved personnel (workers, pharmacists, medical personnel, nurses). Since the patient parameter can vary over a very wide range, it becomes practically very difficult to cater to the precise dose of the drug.

Thus, given many potential hazards and errors associated with the use of the prior known products, there is therefore a need to provide a perfusion system for enabling hospitals or clinics to directly administer to patients in need thereof, a dose of an antineoplastic drug calculated according to a patient parameter, wherein the parameter varies over a range in the patient population. The present invention fulfills this need. The present invention provides a perfusion system comprising plurality of perfusion containers in different sets, each filled with an aqueous, ready-to-infuse perfusion solution of the antineoplastic drug and which enables hospitals or clinics to administer a dose of an antineoplastic drug calculated according to at least one patient parameter, to patients in need thereof, while avoiding any of the steps of manipulation, dilution, reconstitution, dispensing, sterilization, transfer, handling or compounding before intravenous administration.

SUMMARY OF THE INVENTION

Figure 1:
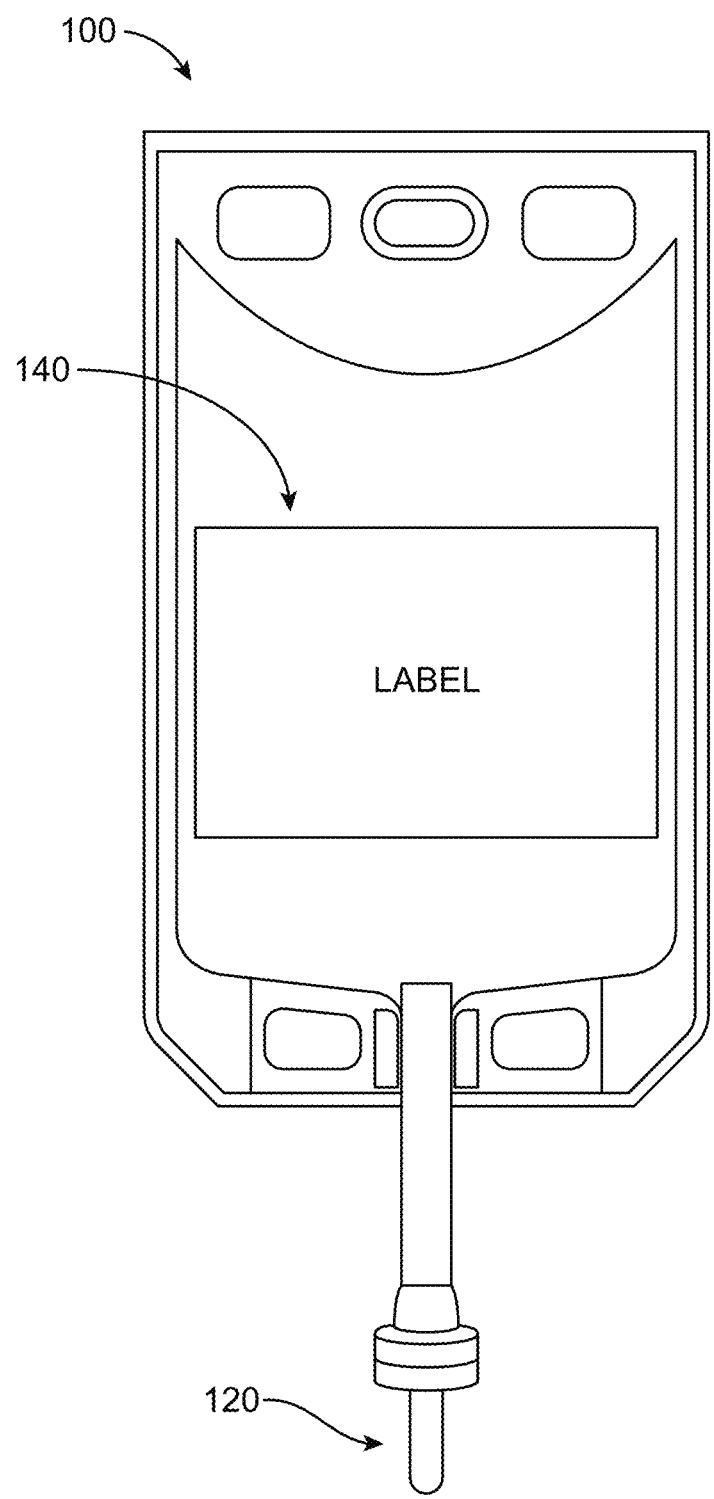
FIG. 1 is a schematic illustration of a perfusion container in accordance with various aspects of the disclosure.

The present invention provides a perfusion system for enabling hospitals or clinics to directly administer to patients in need thereof a dose of an antineoplastic drug calculated according to a patient parameter, wherein the parameter varies over a range in the patient population, said system comprising:
  plurality of perfusion containers, each container comprising a ready-to-infuse, aqueous perfusion solution of an antineoplastic drug, wherein said plurality of perfusion containers comprise a first set of perfusion container (s) comprising a ready-to-infuse, aqueous perfusion solution of an antineoplastic drug and a second set of top-up perfusion containers comprising a ready-to-infuse, aqueous perfusion solution of the antineoplastic drug and optionally a third set of top-up perfusion containers comprising a ready-to-infuse, aqueous perfusion solution of the antineoplastic drug, and
  instructions for selecting one or more perfusion container(s) from the first set and if required one or more top-up perfusion container(s) from the second and/or third set for directly administering the calculated dose of the antineoplastic drug from the selected perfusion containers The present invention further provides a method for directly administering to a patient in need thereof a dose of an antineoplastic drug calculated according to a patient parameter, wherein the parameter varies over a range in the patient population, the method comprising the steps of:
  providing the perfusion system of the present invention;
  calculating the dose according to a patient parameter,
  selecting one or more perfusion container(s) from the first set of perfusion container(s) and if necessary from the second and/or third set of top-up perfusion container(s) required for directly administering the calculated dose and
  directly administering to the patient in need thereof the perfusion solution in the selected containers.

DETAILED DESCRIPTION OF THE PRESENT INVENTION

The term "ready-to-infuse' or 'directly administer' or 'directly administering' or 'direct intravenous infusion' as used herein refers to direct intravenous infusion of the aqueous solution of antineoplastic drug to the patient without involving any intermediate steps of manipulation, dilution, reconstitution, dispensing, sterilization, transfer, handling or compounding before intravenous parenteral administration of the drug solution to the patient. The aqueous drug solution can be directly administered parenterally from the perfusion container. Suitably, the perfusion system and the method according to the present invention avoids any manipulation, any step of reconstituting or dilution such as those involved in conventional lyophilized or concentrated products. It further does not involve any step of transfer of infusion solution from one container to another before administration or any volume adjustment, i.e. addition or withdrawal of the aqueous solution from the perfusion container, before administration. The term "ready-to-infuse' or 'directly administer' or 'directly administering' or 'direct intravenous infusion' also includes within its meaning administering the perfusion solution present in the perfusion container without the need to monitor the volume perfused. This eliminates the risk of any potential calculation or dilution error as well as risk of microbiological contamination prior to administration. This also eliminates or minimizes contact of the drugs by hospital personnel, thus avoiding any potential side effects associated with the cytotoxic antineoplastic drugs. The terms "ready-to-infuse' or 'directly administer' or 'directly administering' or 'direct intravenous infusion' also means that the perfusion containers are filled with the aqueous perfusion solution of the antineoplastic drug and subjected to sterilization process in the pharmaceutical manufacturing facility. This is different from hospital compounding, which involves intermediate steps of dispensing or mixing of the aqueous solution which has been manufactured separately in a manufacturing plant or site and supplied in bulk volumes to the hospital or pharmacy. The term 'directly administer' excludes any transfer of the solution from a bulk container such as used in a pharmacy into the perfusion container from where the solution is intravenously administered.

Hereinafter, the terms "ready-to-infuse' or 'directly administer' or 'directly administering' or 'direct intravenous infusion' as used in the specification should be understood to refer to the meaning as defined herein.

The term 'perfusion' as used herein in the present invention, refers to the intravenous infusion or administration of a solution of a drug to a patient.

The term 'calculated dose' or 'dose calculated according to at least one patient parameter' as used herein means the dose of the antineoplastic drug that is to be administered to the patient depending upon the disease condition or indication and the patient parameters such as body surface area, body weight, renal clearance or hepatic function and other factors, that may affect the dose calculation.

The term "administering the calculated dose" as used herein means administering the calculated dose with precision. For example as shown in illustrative tables (a) to (m), as the body surface area increases by increments of 0.1 mg/m$^2$ there is or are available perfusion containers in the set, for delivery of a precise dose. The tables illustrate that the precise dose is within ±5% of the calculated dose.

The term 'instructions' as used herein refers to the instructions accompanying the perfusion system of the present invention, which may be in the form of a written or electronic communication. The instructions may be provided with one or more perfusion container(s) of the perfusion system or a single set of instructions with the perfusion system or may be made available electronically. The instructions involve directions for arriving at the dose desired for a patient based on patient parameter and for appropriately selecting perfusion containers from the first or second or third set of perfusion containers and for directly administering the drug from the perfusion containers to deliver the desired dose within ±5% variance. The electronic instructions may be in the form of a chip or barcode which correspond to the instructions that can be read with the help of an electronic device.

The present invention provides a perfusion system for enabling hospitals or clinics to directly administer a dose of an antineoplastic drug calculated according to at least one patient parameter, to patients in need thereof, wherein the parameter varies over a range in the patient population. The direct administration avoids any of the steps of manipulation, dilution, reconstitution, dispensing, sterilization, transfer, handling or compounding before intravenous administration.

The antineoplastic drugs that may be used according to the present invention includes, but are not limited to cisplatin, carboplatin, oxaliplatin, vincristine, vinblastine, vinorelbine, vindesine, pemetrexed, gemcitabine, irinotecan, topotecan, methotrexate, docetaxel, paclitaxel, doxorubicin, daunonibicin, epirubicin, idarubicin, streptozocin, mitomycin, gentamicin, tenoposide, 5-fluorouracil, ifosfamide, cyclophosphamide, mechlorethamine, carmustine, dacarbazine, cladribine, clofarabine, fulvestrant, pegfilgrastim, pamidronate, zoledronic acid, mitoxantrone, leukovorin, etoposide, triplatin, picoplatin, satraplatin, lobaplatin or pharmaceutically acceptable salts thereof. According to some preferred embodiments, the antineoplastic drugs include platinum complex compounds such as cisplatin, carboplatin and oxaliplatin; vinca alkaloid drugs such as vincristine, vinblastine, vinorelbine, vindesine, antifolates such as pemetrexed; nucleoside metabolic inhibitor such as gemcitabine, topoisomerase inhibitor such as irinotecan or pharmaceutically acceptable salts thereof. The amount or concentration of the antineoplastic drugs in the perfusion system of the present invention is expressed in terms of the acid or base of the antineoplastic agent. The amount of antineoplastic drug is expressed in terms of the base used and when a salt is used, the amount may be converted into equivalent weight.

The perfusion system can be configured for a particular dosing regimen by using a specific concentration that can cater to a relatively wider range of patient population, such as for example patient population having body surface area varying from 1.4 to 2.6, preferable 1.6 to 2.1. For example for an antineoplastic drug irinotecan, such a specific concentration was found to be 0.7 mg/ml for a dosing regimen requiring 125 mg/m$^2$ or 180 mg/m$^2$ dose to be administered or a specific concentration was found to be 1.2 mg/ml for a dosing regimen requiring 350 mg/m$^2$ dose to be administered. For example for another antineoplastic drug carboplatin, such a specific concentration was found to be 2.0 mg/ml for a dosing regimen requiring 200 mg/m$^2$ dose to be administered. For example for another anti-neoplastic drug docetaxel, such a specific concentration was found to be 0.3 mg/ml for a dosing regimen requiring 55 mg/m$^2$ dose to be administered. For example for another anti-neoplastic drug oxaliplatin, such a specific concentration was found to be 0.7 mg/ml for a dosing regimen requiring 85 mg/m$^2$ dose to be administered. For example for another anti-neoplastic drug gemcitabine, such a specific concentration was found to be 10.0 mg/ml for a dosing regimen requiring 1000 mg/m$^2$ or 1250 mg/m$^2$ dose to be administered. For certain antineoplastic drugs, it was found that a combination of two different such specific concentrations could also be used to cater to a relatively wider range of patient population, such as for example patient population having body surface area varying from 1.4 to 2.6, preferable 1.6 to 2.1. Such drugs include cisplatin, topotecan, irinotecan, carboplatin, oxaliplatin, vincristine, vinblastine, vinorelbine, azacitidine, pemetrexed, gemcitabine, paclitaxel, cyclophosphamide, docetaxel, arsenic trioxide, fluorouracil and the like. For example, for an anti-neoplastic drug paclitaxel at a dose of 50 mg/m$^2$, the concentration of solution was found to be 0.5 mg/ml in first perfusion container and 0.4 mg/ml in the second set of top-up perfusion container. For example, for an anti-neoplastic drug irinotecan at a dose of 180 mg/m$^2$, the concentration of solution was found to be 1.5 mg/ml in first perfusion container and 0.2 mg/ml in the second set of top-up perfusion container.

In some embodiments the perfusion system comprises a kit with perfusion containers of two or more antineoplastic drugs so as to cater to the desired doses as per combination regimens. For example in case of colorectal cancer combination regimen, a combination of irinotecan, leucovorin and 5-fluorouracil needs to be administered and the combination regimen involves administering 180 mg/m2 irinotecan as intravenous infusion over 90 minutes on days 1, 15 and 29 with leucovorin 200 mg/m² intravenous infusion over two hours on days 1, 2, 15, 16, 29 and 30 followed by 5-fluorouracil 400 mg/m² intravenous bolus infusion on days 1, 2, 15, 16, 29 and 30 and 5-fluorouracil 600 mg/m² intravenous infusion over 22 hours on days 1, 2, 15, 16, 29 and 30.

In some embodiments, the perfusion system according to the present invention comprises plurality of perfusion containers prepared in large scale manufacturing unit, each container comprising a ready-to-infuse, aqueous perfusion solution of an antineoplastic drug. The plurality of perfusion containers according to the present invention includes a first set of perfusion container(s) comprising a ready-to-infuse, aqueous perfusion solution of an antineoplastic drug and a second set of top-up perfusion containers comprising a ready-to-infuse, aqueous perfusion solution of the antineoplastic drug and optionally a third set of top-up perfusion containers comprising a ready-to-infuse, aqueous perfusion solution of the antineoplastic drug. The number of containers per set may range from one to fifteen containers. For instance, each set of containers may include 1 to 10 containers having varying amount of the antineoplastic drug per container. The perfusion system further includes instructions to the user such as pharmacist or hospital staff to select appropriate number of containers from one or more set of the perfusion containers so as to administer the calculated dose with precision. Suitably the precise dose delivered is equal to or within ±5%, preferably within ±3% of a dose calculated according to at least one patient parameter.

Whereas in some embodiments, the number of containers in each set may be selected such that for almost the entire patient population with varying patient parameter such as body surface area or weight, a combination of containers to deliver the calculated dose can be found. There are provided other embodiments that target a smaller population with a narrower range of patient parameter. In such embodiments, the number of containers per set is 1, 2, 3, 4, 5, 6, 7 and not more than 10. In preferred embodiments, the number of first perfusion containers may be 5 and the number of second top-up containers may be 1, 2, 3, 4, 5, 6, 7, 8, 9 or 10, preferably, 1 or 2 or 3.

In a more preferred example there is provided one container from the first set and a second container from the second set. For example, for an antineoplastic drug with a dose of 180 mg/m², the first set has only one container having a concentration of antineoplastic drug at 1.5 mg/ml and a volume of 200 ml, and second set has only two containers each having a concentration of antineoplastic drug at 0.2 mg/ml and a volume of 150 ml. The set can be used for accurate dosing of patients with body surface area in the range 1.6 to 2.1 mg/m² as illustrated below:

| BSA ($m^2$) | Total Target Dose to be delivered (mg) D | First Perfusion container, 200 ml (blue band) Antineoplastic drug at concentration of 1.5 mg/ml | | Top-up perfusion container, 150 ml (red band) Antineoplastic drug at concentration of 0.3 mg/ml: | | Total dose delivered (mg) (a + b) | % Variation** from delivered dose Vs calculated dose |
|---|---|---|---|---|---|---|---|
| | | Volume of perfusion container (ml) | Dose delivered from perfusion container (a) (mg) | Volume of top up container (ml) | Dose delivered from top up container (b) (mg) | | |
| 1.6 | 288 | 200 | 300 | 0 | 0 | 300 | 4.2 |
| 1.7 | 306 | 200 | 300 | 0 | 0 | 300 | −2.0 |
| 1.8 | 324 | 200 | 300 | 100 | 30 | 330 | 1.9 |
| 1.9 | 342 | 200 | 300 | 100 | 30 | 330 | −3.5 |
| 2.0 | 360 | 200 | 300 | 100 × 2 | 60 | 360 | 0.0 |
| 2.1 | 378 | 200 | 300 | 100 × 2 | 60 | 360 | −4.8 |

**% Variation from delivered dose Vs calculated dose = [((a + b) − D]/D × 100

The perfusion system of above Table is accompanied by suitable instructions for example as below:

| BSA ($m^2$) | Instructions |
|---|---|
| 1.6 and 1.7 | Infuse the full volume from one 200 ml container with blue band |
| 1.8 and 1.9 | Infuse the full volume from one 200 ml container with blue band and full volume from one 100 ml top-up container with red band |
| 2.0 and 2.1 | Infuse the full volume from one 200 ml container with blue band and full volume from two 100 ml top-up containers with red band |

Thus accordingly the present invention provides a perfusion container for directly administering to patients a dose of an antineoplastic drug calculated according to a patient's parameter, wherein the first perfusion container comprises a solution of antineoplastic drug at a concentration and volume such that the amount of antineoplastic drug in the container is equal to the calculated dose for one patient but less than the calculated dose for a second patient, the calculated dose is provided to first patient within 5% variance by directly administering the full volume of the solution of antineoplastic drug from the first perfusion container, further the first perfusion container is accompanied by a second top-up perfusion container comprising a solution of antineoplastic drug at a concentration and volume such that the calculated dose is provided within 5% variance by directly administering the full volume of the solution of antineoplastic drug from the first perfusion container and the second top-up container to the second patient.

According to one embodiment, the concentrations the concentration in the first perfusion container and the concentration in the second top-up perfusion container is same. According to one preferred embodiment, the concentration in the first perfusion container is higher than the concentration in the second top-up perfusion container.

According to one embodiment, the volume in the first perfusion container and the volume in the second top-up perfusion container is same. According to one preferred embodiment, the volume in the perfusion container is higher than the volume in the second top-up perfusion container.

Alternatively, the present invention also provides a perfusion container for directly administering to a patient a dose of an antineoplastic drug calculated according to the patient's parameter, wherein the perfusion container comprises a solution of antineoplastic drug at a concentration and volume such that the amount of antineoplastic drug in the container is less than the calculated dose, further wherein the perfusion container is accompanied by a second top-up perfusion container comprising a solution of antineoplastic drug at a concentration and volume such that the calculated dose is provided within 5% variance by directly administering the full volume of the solution of antineoplastic drug from the first perfusion container and the second top-up container.

According to one embodiment, the concentrations and volumes of perfusion solution in the selected set of containers are such that for each dose calculated according to a parameter for any given patient in the patient population, a first container and if necessary top-up perfusion container(s) can be selected to deliver the dose by administering the full volume in the selected containers without the need to monitor the volume of perfusion solution administered and the dose is delivered with precision. The dose can be delivered with precision, i.e. within ±5% variance, preferably within ±3% variance from the calculated dose.

According to one embodiment of the present invention, there is provided a perfusion container configured to be one of perfusion containers, in the perfusion system of the present invention, wherein the perfusion container comprises a ready to infuse perfusion solution of a partial dose of an antineoplastic drug for some patients in the patient population, wherein the dose is calculated according to a patient parameter.

According to the present there is further provided a method for directly administering to a patient in need thereof a dose of an antineoplastic drug calculated according to a patient parameter, wherein the parameter varies over a range in the patient population, the method comprising the steps of: providing the perfusion system of the present invention; calculating the dose according to a patient parameter, selecting one or more perfusion container(s) from the first set of perfusion container(s) and if necessary from the second and/or third set of top-up perfusion container(s) required for directly administering the calculated dose and directly administering to the patient in need thereof the perfusion solution in the selected containers.

The perfusion system and method of the present invention advantageously thus covers a range of patient population having wide range of patient parameter. For instance, when the patient parameter is body surface area (BSA), it is generally known to vary over a range of 1.2 to 2.8 mg/m$^2$ in a patient population. The perfusion system and method of the present invention advantageously covers the whole range of such a patient population and is suitable to directly administer the calculated dose with precision, which is achieved because of the unique configuration of the perfusion system of the present invention.

According to the present invention, there is provided instructions for arriving at the dose of antineoplastic drug desired for a patient in need thereof, based on one of patient parameter and for appropriately selecting one or more perfusion container(s) from the first set and if required one or more top-up perfusion container(s) from the second and/or third set perfusion containers and for directly administering the antineoplastic drug from the selected perfusion containers to deliver the desired calculated dose with precision. The instructions may be in the form of written instructions or electronic instruction or any other suitable form accompanying the perfusion system and/or with one or more perfusion container of the perfusion system. The written instructions may be in the form of a package insert or labeling. The electronic instructions may be in the form of a chip or barcode which correspond to the instructions that can be read with the help of an electronic device. Preferably the instructions are written instructions accompanying the perfusion system and/or with one or more perfusion container of the perfusion system.

The perfusion system and method according to the present invention comprises a first set of perfusion containers comprising a ready-to-infuse, aqueous perfusion solution of an antineoplastic drug at a first concentration, a second set of top-up perfusion containers comprising a ready-to-infuse, aqueous perfusion solution of the antineoplastic drug at a second concentration and optionally a third set of top-up perfusion containers comprising a ready-to-infuse, aqueous perfusion solution of the antineoplastic drug at a third concentration.

According to one embodiment of the present invention, the first, second and/or third concentrations may be same or different. Preferably, according to one embodiment, the first, second and/or third concentrations are different. According to one embodiment, the first, second and/or third concentrations are same.

According to one embodiment of the present invention, the volume of solution in the individual containers may be same or different. Preferably, according to one embodiment, the volume of solution in the individual containers is different. According to one embodiment, the volume of solution in the individual containers is same.

According to one preferred embodiment of the present invention, the first concentration, the second concentration and/or third concentration are different. According to this embodiment, the volume of solution in the first set, second set and/or third set of containers may be same or different. In one preferred embodiment, the first, second and/or third concentrations are different and the volume of solution in the first set is different from the volume of solution in the second set and/or third set of containers. In another embodiment, the first, second and/or third concentrations are different and the volume of solution in the first set and in the second set and/or third set of containers is same.

According to one embodiment of the present invention, the first, second and/or third concentrations are same. According to this embodiment, the volume of solution in the first set, second set and/or third set of containers are different.

According to one embodiment of the present invention, the first set of perfusion containers and the second set of top-up perfusion containers, and/or the third set of top-up perfusion containers each comprise a plurality of containers containing different volumes of ready-to-infuse, aqueous perfusion solution of an antineoplastic drug.

According to another preferred embodiment, the first, second and/or third concentrations are different and the first concentration is higher than the second and/or third concentration, further wherein the volume of solution in the first set is higher than the volume of solution in the second set and/or third set of containers. According to another embodiment, the first, second and/or third concentrations are different, further wherein the first concentration is higher than the second and/or third concentration, further wherein the volume of solution in the first set is lower than the volume of solution in the second set and/or third set of containers.

In one preferred embodiment, the perfusion system comprises the first set, the second set as well as the third set of perfusion containers. In one embodiment, the first concentration is higher than the second concentration and the second concentration is higher than the third concentration. In another embodiment, the first concentration is higher than the second concentration and the second concentration is same as the third concentration.

In one embodiment for antineoplastic drugs such as vincristine, vinblastine, vinorelbine, oxaliplatin, cisplatin, and the like whose dose based on the body surface area ($mg/m^2$) is low, the concentration of drug in the solution of the first set may be lower than the concentration of drug in the solution of second set and/or third set, and the volume of solution in the first set is higher than the volume of solution in the second set and/or third set of containers.

In another embodiment, for antineoplastic drugs such as gemcitabine, pemetrexed, carboplatin or irinotecan whose dose based on the body surface area ($mg/m^2$) is high, the concentration of drug in the solution of the first set is preferably higher than the concentration of drug in the solution of second set and/or third set, and the volume of solution in the first set may be higher or lower, preferably higher, than the volume of solution in the second set and/or third set of containers.

According to the present invention, the set of containers of the perfusion system may range in volume from a lower to a higher volume. The volume of the aqueous solution of drug contained in different perfusion containers may vary from about 10 ml to about 5000 ml, preferably from about 20 ml to about 2000 ml, more preferably from about 25 ml to about 1000 ml. In preferred embodiments, the different set of perfusion containers having different volumes may be distinguished. In particular, the different sets of perfusion containers may be visually distinguished, for example through the use of different patterns or colors on some or all of the containers. In particular different colors may be used for labeling.

According to the present invention, the aqueous perfusion solution may comprise parenterally acceptable, pharmaceutically acceptable excipients or adjuvants. The excipients that may be used are selected from but not limited to pH adjusting and/or buffering agents, tonicity adjusting agents, chelating agents, solvents etc.

In preferred embodiments, the perfusion container according to the present invention may be a perfusion bag, infusion bag, flexible pouch, infusion bottle. The container is made up of a suitable material such as plastic or other polymeric material or glass. The container may be single or multiple layered. In one embodiment, the perfusion containers have a single outlet for withdrawal of the aqueous solution from the container while being administered intravenously. This design avoids any manipulation, such as volume adjustment (addition or removal of aqueous solution) prior to intravenous infusion.

The perfusion container according to the present invention does not include devices such as syringes or autoinjectors, pen or any container that has a needle attached to it, through which the solution would be delivered, and that has low volume capacity such as 1-20 ml. Such containers are known to be used in the prior art to adjust the calculated dose of the drug in the main infusion container by transferring the drug solution from another container to the infusion container or withdrawing a volume of drug solution from the infusion container before administering to the patient.

The perfusion system of the present invention allows the hospital staff to select perfusion containers like infusion bags according to the calculated dose from a set and directly without any manipulation infuse the full volume from each infusion bag to the patient. This does not involve any manipulation or handling in hospital pharmacy and avoids any adjustment of contents and therefore any errors in dose or exposure of the formulation or exposure of the staff to the cytotoxic formulation.

In one embodiment, the perfusion containers may be packaged in a secondary packaging that surrounds the perfusion container. The secondary packaging may comprise a second container such as a pouch or overwrap or carton. The secondary packaging may comprise a suitable pouch, such as an aluminum pouch covering the perfusion container. The overwrap pouch may have a layer of oxygen absorbing material. The secondary packaging may further comprise an oxygen scavenger that may be placed in between the perfusion container and overwrap/pouch. In one preferred embodiment, the secondary packaging comprises both an aluminum pouch and an oxygen scavenger.

The perfusion system comprising containers filled with aqueous solution of anti-neoplastic drug according to the present invention are useful in the treatment of cancer or neoplastic disorders. In one preferred embodiment, wherein the drug is Irinotecan hydrochloride, the perfusion system is useful for the treatment of metastatic colorectal cancer wherein the target dose of irinotecan to be delivered is based on body surface area (BSA). It may be used as a Colorectal Combination Regimens, wherein 125 $mg/m^2$ intravenous (i.v.) infusion is administered over 90 minutes on Days 1, 8, 15, 22 in 6-week cycles with 5-fluorouracil and leucovorin. It may alternatively be used at 180 $mg/m^2$ as an i.v. infusion over 90 minutes on Days 1, 15, 29 in 6-week cycles with 5-fluorouracil and leucovorin. It may also be used as a Colorectal Single-Agent Regimens wherein 125 $mg/m^2$ i.v. infusion is administered over 90 minutes on Days 1, 8, 15, 22 followed by a 2-week rest or it may alternatively be used as 350 $mg/m^2$ i.v. infusion over 90 minutes once every 3 weeks.

Suitably, the perfusion system of the present invention is sterile. The term "sterile" as used in the context of the invention, means that the aqueous solution has been brought to a state of sterility and the solution complies with the sterility requirements of the standard Pharmacopoeias like United States Pharmacopoeias (USP). Sterilization may be achieved by suitable techniques such as filtration sterilization, radiation sterilization and the like.

FIG. 1 is a schematic illustration of a perfusion container 100 containing an antineoplastic drug in accordance with various aspects of the disclosure. As shown, the perfusion container 100 includes an outlet 120 and a label 140. Label 140 may include information regarding the contents of the perfusion container 100 including the name of the antineoplastic drug solution, the antineoplastic drug concentration within the solution, the volume of the antineoplastic drug solution within the perfusion container 100 and dosage information for treatment of a patient with the antineoplastic drug solution.

Figure 2:
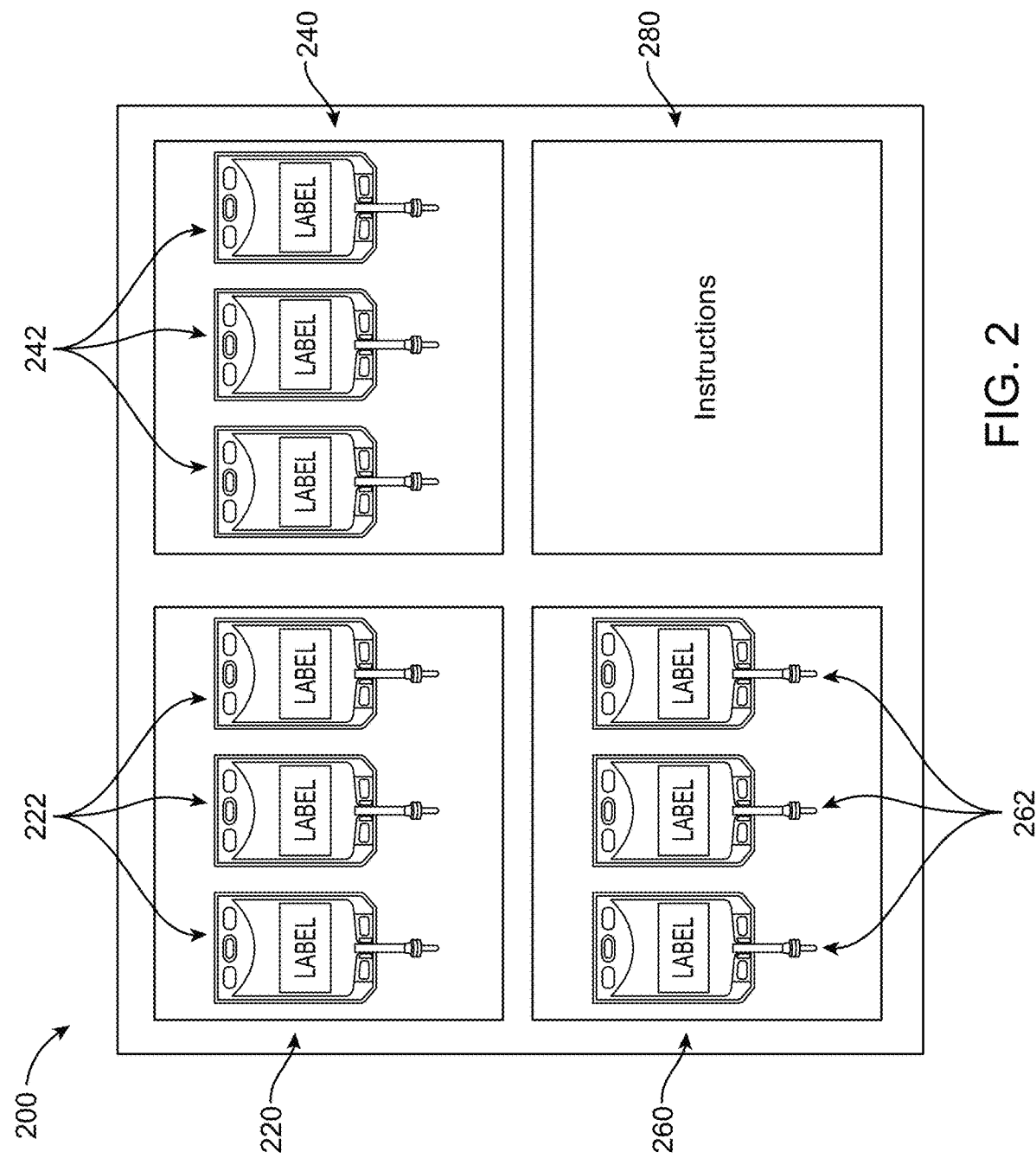
FIG. 2 is a schematic illustration of a perfusion system in accordance with various aspects of the disclosure.

FIG. 2 is a schematic illustration of a perfusion system 200 in accordance with various aspects of the disclosure. As shown, the perfusion system 200 includes a first set of perfusion containers 220, a second set of top-up perfusion containers 240, and a third set of top-up perfusion containers 260. In FIG. 2, the first set of perfusion containers 220 includes three perfusion containers 222, the second set of top-up perfusion containers 240 includes three perfusion containers 242, and the third set of top-up perfusion containers 260 includes three perfusion containers 262. As described herein, the sets of perfusion containers 220, 240, 260 may include 1 to 10 containers having varying concentrations and/or volumes of a particular antineoplastic drug solution and/or different antineoplastic drug solutions with different antineoplastic drugs, solution concentrations and/or solution volumes. The perfusion system further includes instructions 280 for selecting one or more perfusion containers from the first set of perfusion containers 220, the second set of top-up perfusion containers 240, and the third set of top-up perfusion containers 260 for directly administering to a patient the calculated dose of the antineoplastic drug from the selected perfusion containers.

Illustrations

According to one embodiment, there is provided a perfusion system for administration of irinotecan or its pharmaceutical acceptable salts and or hydrates thereof. Table 1 below provide details of the perfusion system having containers of first and second set with the ranges of concentration and volume of the solution or irinotecan per set.

TABLE 1

Perfusion system of Irinotecan:

| | First set of Perfusion container | Second set of top up perfusion container |
|---|---|---|
| Concentration range (mg/ml) | 1.0-3.0 | 0.1-0.8 |
| Preferred concentration range (mg/ml) | 1.5-2.0 | 0.2-0.4 |
| Volume range (ml) | 80-500 | 50-350 |
| Preferred volume range (ml) | 90-300 | 75-150 |

The perfusion system may comprise one or more perfusion containers in the first set and one or more perfusion containers in the second set. In some embodiments, the first set of perfusion containers contain solution having higher irinotecan concentration then the solution in second set of top-up perfusion containers. In some embodiments, the first set of perfusion container and second set of top-up perfusion containers contain solution having same irinotecan concentration, but different volume. Preferably the volume of solution in the first set of perfusion containers is higher than that in the second set of top-up containers.

In one preferred embodiment, the first set of infusion containers comprise perfusion solution having irinotecan or its pharmaceutical acceptable salts at a concentration ranging from about 1.0 mg/ml to 3.0 mg/ml and volume of solution ranging from about 80 ml to about 500 ml, further wherein the second or third set of infusion containers comprise perfusion solution having irinotecan at a concentration ranging from about 0.1 to 0.8 mg/ml and volume of solution ranging from about 50 ml to about 350 ml. The amount of irinotecan mentioned herein in the examples refers to the concentration of irinotecan base. When the solution contain a pharmaceutical acceptable salt or hydrate of irinotecan, the amount in mg/ml of the salt or hydrate will be higher depending upon the type of salt or hydrate and the said salt or hydrate will have an equivalent amount of irinotecan depending upon the molecular weight. For instance, if irinotecan hydrochloride trihydrate is used in amounts of 1.5 mg/ml, the equivalent amount of irinotecan that it will contain will be 1.3 mg/ml.

In one embodiment, irinotecan is used for the treatment of colorectal cancer and it may be either administered as a combination regimen having irinotecan, leucovorin and 5-fluorouracil or as a single agent regimen. Combination regimen 1 involves administering 125 mg/m$^2$ irinotecan as intravenous infusion over 90 minutes on days 1, 8, 15 and 22 with leucovorin 20 mg/m$^2$ intravenous bolus infusion on days 1, 8, 15, 22 followed by 5-fluorouracil 500 mg/m$^2$ intravenous bolus infusion on days 1, 8, 15, and 22 every 6-weeks. Combination regimen 2 involves administering 180 mg/m$^2$ irinotecan as intravenous infusion over 90 minutes on days 1, 15 and 29 with leucovorin 200 mg/m$^2$ intravenous infusion over two hours on days 1, 2, 15, 16, 29 and 30 followed by 5-fluorouracil 400 mg/m$^2$ intravenous bolus infusion on days 1, 2, 15, 16, 29 and 30 and 5-fluorouracil 600 mg/m$^2$ intravenous infusion over 22 hours on days 1, 2, 15, 16, 29 and 30. Single-Agent Regimen 1 involves 125 mg/m$^2$ i.v. infusion, administered over 90 minutes on Days 1, 8, 15, 22 followed by a 2-week rest. Single-Agent Regimen 2 involves 350 mg/m$^2$ i.v. infusion over 90 minutes once every 3 weeks.

The perfusion system of the present invention is so configured that it provides the desired target dose of irinotecan (within ±5% of variation) as per the regimens illustrated above and can cater to a relatively wider range of patient population, such as for example patient population having body surface area varying from 1.4 to 2.6, preferable 1.6 to 2.1 using limited number of perfusion containers.

As illustrated below in Table 2, for combination regimen 1 and single-agent regimen 1, (having irinotecan dose of 125 mg/m$^2$), it is possible to have the following kit with 5 containers and with following instructions to cater to the desired target dose of irinotecan for patient population having body surface area varying from 1.3 to 2.6:

TABLE 2

Description of perfusion system of Irinotecan according to one embodiment:

| | | First set of Perfusion container Drug concentration—0.7 mg/ml: | | Top-up perfusion containers- Second set Drug concentration—0.7 mg/ml: | | | |
|---|---|---|---|---|---|---|---|
| BSA (m$^2$) | Total Target Dose at 125 mg/m2 to be delivered (mg) D | Volume delivered from first perfusion container (ml) | Dose delivered from first perfusion container (a) (mg) | Volume delivered from second top up perfusion container (ml) | Dose delivered from top-up container (b) (mg) | Total dose delivered (mg) (a + b) | % Variation** from delivered dose Vs calculated dose |
| 1.3 | 162.5 | 240 | 168 | 0 | 0 | 168 | 3.4 |
| 1.4 | 175 | 240 | 168 | 0 | 0 | 168 | −4.0 |
| 1.5 | 187.5 | 270 | 189 | 0 | 0 | 189 | 0.8 |

TABLE 2-continued

Description of perfusion system of Irinotecan according to one embodiment:

| BSA (m²) | Total Target Dose at 125 mg/m2 to be delivered (mg) D | First set of Perfusion container Drug concentration—0.7 mg/ml: | | Top-up perfusion containers- Second set Drug concentration—0.7 mg/ml: | | Total dose delivered (mg) (a + b) | % Variation** from delivered dose Vs calculated dose |
|---|---|---|---|---|---|---|---|
| | | Volume delivered from first perfusion container (ml) | Dose delivered from first perfusion container (a) (mg) | Volume delivered from second top up perfusion container (ml) | Dose delivered from top-up container (b) (mg) | | |
| 1.6 | 200 | 240 | 168 | 50 | 35 | 203 | 1.5 |
| 1.7 | 212.5 | 240 | 168 | 50 | 35 | 203 | -4.5 |
| 1.8 | 225 | 270 | 189 | 50 | 35 | 224 | -0.4 |
| 1.9 | 237.5 | 240 | 168 | 100 | 70 | 238 | 0.2 |
| 2.0 | 250 | 270 | 189 | 100 | 70 | 259 | 3.6 |
| 2.1 | 262.5 | 270 | 189 | 100 | 70 | 259 | -1.3 |
| 2.2 | 275 | 400 | 280 | 0 | 0 | 280 | 1.8 |
| 2.3 | 287.5 | 400 | 280 | 0 | 0 | 280 | -2.6 |
| 2.4 | 300.0 | 400 | 280 | 50 | 35 | 315 | 5.0 |
| 2.6 | 325.0 | 400 | 280 | 50 | 35 | 315 | -3.1 |

**% Variation from delivered dose Vs calculated dose = [((a + b) − D]/D × 100

The abbreviation BSA as used in the illustrations stands for patient's Body Surface Area.

The containers of the perfusion system of Table (2) may be alphabetically coded as follows:

| First set of Perfusion containers Irinotecan concentration 0.7 mg/ml | | Second set of top-up perfusion containers; Irinotecan concentration 0.7 mg/ml: | |
|---|---|---|---|
| Volume of perfusion container (ml) | Alphabetical Code | Volume of top up container (ml) | Alphabetical Code |
| 240 | A | 50 | D |
| 270 | B | 100 | E |
| 400 | C | | |

The perfusion system of above Table (2) is accompanied by suitable instructions for example as below:

| BSA (m²) | Instructions |
|---|---|
| 1.3 and 1.4 | Infuse the full volume from one 240 ml container having an alphabetical code A |
| 1.5 | Infuse the full volume from one 270 ml container having an alphabetical code B |
| 1.6 and 1.7 | Connect one 240 ml container having an alphabetical code A to one 50 ml container having an alphabetical code D and infuse the full volume |
| 1.8 | Connect one 270 ml container having an alphabetical code B to one 50 ml container having an alphabetical code D and infuse the full volume |
| 1.9 | Connect one 240 ml container having an alphabetical code A to one 100 ml container having an alphabetical code E and Infuse the full volume |
| 2.0 and 2.1 | Connect one 270 ml container having an alphabetical code B to one 100 ml container having an alphabetical code E and Infuse the full volume |
| 2.2 and 2.3 | Infuse the full volume from one 400 ml container having an alphabetical code C |
| 2.4 and 2.6 | Connect one 400 ml container having an alphabetical code C to one 50 ml container having an alphabetical code D and infuse the full volume |

As illustrated below in Table 3, for combination regimen 2, (having irinotecan dose of 180 mg/m²), it is possible to have the following kit with 5 containers and with following instructions to cater to the desired target dose of irinotecan for patient population having body surface area varying from 1.3 to 2.6:

TABLE 3

Description of perfusion system of Irinotecan according to one embodiment:

| BSA* (m²) | Total Target Dose to be delivered (mg) D | First set of Perfusion containers Irinotecan concentration 0.7 mg/ml | | Second set of top-up perfusion containers; Irinotecan concentration 0.7 mg/ml: | | Total dose delivered (mg) (a + b) | % Variation** from delivered dose Vs calculated dose |
|---|---|---|---|---|---|---|---|
| | | Volume of perfusion container (ml) | Dose delivered from perfusion container (a) (mg) | Volume of top up container (ml) | Dose delivered from top-up container (b) (mg) | | |
| 1.3 | 234 | 350 | 245 | 0 | 0 | 245 | 3.8 |
| 1.4 | 252 | 350 | 245 | 0 | 0 | 245 | -2.8 |
| 1.5 | 270 | 350 | 245 | 50 | 35 | 280 | 3.7 |
| 1.6 | 288 | 350 | 245 | 50 | 35 | 280 | -2.8 |
| 1.7 | 306 | 450 | 315 | 0 | 0 | 315 | 2.9 |
| 1.8 | 324 | 450 | 315 | 0 | 0 | 315 | -2.8 |
| 1.9 | 342 | 450 | 315 | 50 | 35 | 350 | 2.3 |

TABLE 3-continued

Description of perfusion system of Irinotecan according to one embodiment:

| | | First set of Perfusion containers Irinotecan concentration 0.7 mg/ml | | Second set of top-up perfusion containers; Irinotecan concentration 0.7 mg/ml: | | | |
|---|---|---|---|---|---|---|---|
| BSA* ($m^2$) | Total Target Dose to be delivered (mg) D | Volume of perfusion container (ml) | Dose delivered from perfusion container (a) (mg) | Volume of top up container (ml) | Dose delivered from top-up container (b) (mg) | Total dose delivered (mg) (a + b) | % Variation** from delivered dose Vs calculated dose |
| 2 | 360 | 450 | 315 | 50 | 35 | 350 | −2.8 |
| 2.1 | 378 | 550 | 385 | 0 | 0 | 385 | 1.9] |
| 2.2 | 396 | 550 | 385 | 0 | 0 | 385 | −2.8 |
| 2.3 | 414 | 550 | 385 | 50 | 35 | 420 | 1.4 |
| 2.4 | 432 | 550 | 385 | 50 | 35 | 420 | −2.8 |
| 2.5 | 450 | 550 | 455 | 100 | 70 | 455 | 1.1 |
| 2.6 | 468 | 550 | 455 | 100 | 70 | 455 | −2.8 |

**% Variation from delivered dose Vs calculated dose = [((a + b) − D]/D × 100

The containers of the perfusion system of Table (3) may be alphabetically coded as follows:

| First set of Perfusion containers Irinotecan concentration 0.7 mg/ml | | Second set of top-up perfusion containers; Irinotecan concentration 0.7 mg/ml: | |
|---|---|---|---|
| Volume of perfusion container (ml) | Alphabetical code | Volume of top up container (ml) | Alphabetical code |
| 350 | F | 50 | D |
| 450 | G | 100 | E |
| 550 | H | | |

The perfusion system of above Table (3) is accompanied by suitable instructions for example as below:

| BSA ($m^2$) | Instructions |
|---|---|
| 1.3 and 1.4 | Infuse the full volume from one 350 ml container having an alphabetical code F |
| 1.5 and 1.6 | Connect one 350 ml container having an alphabetical code F to one 50 ml container having an alphabetical code D and infuse the full volume |
| 1.7 and 1.8 | Infuse the full volume from one 450 ml container having an alphabetical code G |
| 1.9 and 2.0 | Connect one 450 ml container having an alphabetical code G to one 50 ml container having an alphabetical code D and infuse the full volume |
| 2.1 and 2.2 | Connect one 550 ml container having an alphabetical code H and Infuse the full volume |
| 2.3 and 2.4 | Connect one 550 ml container having an alphabetical code H to one 50 ml container having an alphabetical code D and Infuse the full volume |
| 2.5 and 2.6 | Connect one 550 ml container having an alphabetical code H to one 100 ml container having an alphabetical code E and Infuse the full volume |

As illustrated below in Table 4, for combination regimen 4, (having irinotecan dose of 350 mg/m²), it is possible to have the following kit with 5 containers and with following instructions to cater to the desired target dose of irinotecan for patient population having body surface area varying from 1.3 to 2.4:

TABLE 4

Description of perfusion system of Irinotecan according to one embodiment:

| | | First set of Perfusion container Drug concentration—1.2 mg/ml: | | Top-up perfusion containers - Second set Drug concentration—1.2 mg/ml: | | | |
|---|---|---|---|---|---|---|---|
| BSA ($m^2$) | Total Target Dose to be delivered (mg) D | Volume delivered from first perfusion container (ml) | Dose delivered from first perfusion container (a) (mg) | Volume delivered from second top up perfusion container (ml) | Dose delivered from top-up container (b) (mg) | Total dose delivered (a + b) | % Variation** from delivered dose Vs calculated dose |
| 1.3 | 455 mg | 370 | 444 | 0 | 0 | 444 | −2.4 |
| 1.4 | 490 mg | 370 | 444 | 50 | 60 | 504 | 2.9 |
| 1.5 | 525 mg | 450 | 540 | 0 | 0 | 540 | 2.8 |
| 1.6 | 560 mg | 450 | 540 | 0 | 0 | 540 | −3.6 |
| 1.7 | 595 mg | 450 | 540 | 50 | 60 | 600 | 0.8 |
| 1.8 | 630 mg | 450 | 540 | 50 | 60 | 600 | −4.8 |
| 1.9 | 665 mg | 570 | 684 | 0 | 0 | 684 | 2.9 |
| 2.0 | 700 mg | 570 | 684 | 0 | 0 | 684 | −2.9 |
| 2.1 | 735 mg | 570 | 684 | 50 | 60 | 744 | 1.5 |
| 2.2 | 770 mg | 650 | 780 | 0 | 0 | 780 | 1.3 |
| 2.3 | 805 mg | 650 | 780 | 0 | 0 | 780 | −3.1 |
| 2.4 | 840 mg | 650 | 780 | 50 | 60 | 840 | 0 |

The containers of the perfusion system of Table (4) may be alphabetically coded as follows:

| First set of Perfusion containers Irinotecan concentration 1.2 mg/ml | | Second set of top-up perfusion containers; Irinotecan concentration 1.2 mg/ml: | |
|---|---|---|---|
| Volume of perfusion container (ml) | Alphabetical code | Volume of top up container (ml) | Alphabetical code |
| 370 | I | 50 | M |
| 450 | J | | |
| 570 | K | | |
| 650 | L | | |

The perfusion system of above Table (4) is accompanied by suitable instructions for example as below:

| BSA (m$^2$) | Instructions |
|---|---|
| 1.3 | Infuse the full volume from one 370 ml container having an alphabetical code I |
| 1.4 | Connect one 370 ml container having an alphabetical code I to one 50 ml container having an alphabetical code M and infuse the full volume |
| 1.5 and 1.6 | Infuse the full volume from one 450 ml container having an alphabetical code J |
| 1.7 and 1.8 | Connect one 450 ml container having an alphabetical code J to one 50 ml container having an alphabetical code M and infuse the full volume |
| 1.9 and 2.0 | Infuse the full volume from one 570 ml container having an alphabetical code K |
| 2.1 | Connect one 570 ml container having an alphabetical code K to one 50 ml container having an alphabetical code M and infuse the full volume |
| 2.2 and 2.3 | Infuse the full volume from one 650 ml container having an alphabetical code L |
| 2.4 | Connect one 650 ml container having an alphabetical code L to one 50 ml container having an alphabetical code M and infuse the full volume |

For meeting all the dosage requirements (covering all approved dosage regimens for irinotecan and covering wide range of patient population, such as for example patient population having body surface area varying from 1.4 to 2.6), 13 containers coded A to M are required but for each patient only one or 2 containers are used at any one time. In case when two perfusion containers are to be infused to a patient then they may be connected with a Y connector. The perfusion containers have a single outlet for withdrawal of the aqueous solution from the container while being administered intravenously. This design avoids any manipulation, such as volume adjustment (addition or removal of aqueous solution) prior to intravenous infusion.

In another embodiment, there are provided perfusion containers in the first set having drug solution at higher concentration and top-up perfusion containers having drug solution at lower concentration. The dose of Irinotecan for a particular indication is 180 mg/m$^2$ based on patient's body surface area. There is provided instructions to calculate the total dose to be delivered to a patient based on the body surface area and select one container from the first set and one container from the top-up perfusion container to deliver the calculated dose within ±5% variance. This is presented in table 5 below:

TABLE 5

Description of perfusion system of Irinotecan according to one embodiment:

| | | First set of Perfusion containers Irinotecan concentration 1.5 mg/ml | | Second set of top-up perfusion containers; Irinotecan concentration 0.2 mg/ml: | | | |
|---|---|---|---|---|---|---|---|
| BSA* (m$^2$) | Total Target Dose to be delivered (mg) D | Volume of perfusion container (ml) | Dose delivered from perfusion container (a) (mg) | Volume of top up container (ml) | Dose delivered from top-up container (b) (mg) | Total dose delivered (mg) (a + b) | % Variation** from delivered dose Vs calculated dose |
| 1.3 | 234 | 160 | 240 | 0 | 0 | 240 | 2.6 |
| 1.4 | 252 | 160 | 240 | 0 | 0 | 240 | −4.8 |
| 1.5 | 270 | 160 | 240 | 150 | 30 | 270 | 0.0 |
| 1.6 | 288 | 200 | 300 | 0 | 0 | 300 | 4.2 |
| 1.7 | 306 | 200 | 300 | 0 | 0 | 300 | −2.0 |
| 1.8 | 324 | 200 | 300 | 150 | 30 | 330 | 1.9 |
| 1.9 | 342 | 200 | 300 | 150 | 30 | 330 | −3.5 |
| 2 | 360 | 240 | 360 | 0 | 0 | 360 | 0.0 |
| 2.1 | 378 | 240 | 360 | 150 | 30 | 390 | 3.2 |
| 2.2 | 396 | 240 | 360 | 150 | 30 | 390 | −1.5 |
| 2.3 | 414 | 280 | 420 | 0 | 0 | 420 | 1.4 |
| 2.4 | 432 | 280 | 420 | 0 | 0 | 420 | −2.8 |
| 2.5 | 450 | 280 | 420 | 150 | 30 | 450 | 0.0 |
| 2.6 | 468 | 280 | 420 | 150 | 30 | 450 | −3.8 |

**% Variation from delivered dose Vs calculated dose = [((a + b) − D]/D × 100
*BSA—Body Surface Area The containers of the perfusion system of Table (5) may be alphabetically coded as follows:

| First set of Perfusion containers Irinotecan concentration 1.5 mg/ml | | Second set of top-up perfusion containers; Irinotecan concentration 0.2 mg/ml: | |
|---|---|---|---|
| Volume of perfusion container (ml) | Alphabetical code | Volume of top up container (ml) | Alphabetical code |
| 160 | O | 150 | S |
| 200 | P | | |
| 240 | Q | | |
| 280 | R | | |

The perfusion system of Table (5) is accompanied by suitable instructions for example as below:

| BSA (m$^2$) | Instructions |
|---|---|
| 1.3 and 1.4 | Infuse the full volume from one 160 ml container having an alphabetical code O |
| 1.5 | Connect one 160 ml container having an alphabetical code O to one 150 ml container having an alphabetical code S and Infuse the full volume |
| 1.6 and 1.7 | Connect one 200 ml container having an alphabetical code P and one 150 ml container having an alphabetical code S and and Infuse the full volume |
| 1.8 and 1.9 | Connect one 200 ml container having an alphabetical code P to one 150 ml container having an alphabetical code S and Infuse the full volume |
| 2.0 | Infuse the full volume from one 240 ml container having an alphabetical code Q |
| 2.1 and 2.2 | Connect one 240 ml container having an alphabetical code Q to one 150 ml container having an alphabetical code S and Infuse the full volume |
| 2.3 and 2.4 | Infuse the full volume from one 280 ml container having an alphabetical code R |
| 2.5 and 2.6 | Connect one 280 ml container having an alphabetical code R and one 150 ml container having an alphabetical code S and Infuse the full volume |

As described above, the target dose of Irinotecan for a person having a specific body surface area can be delivered (within ±5% variance), by the perfusion system of the present invention, by infusing the full volume of solution from the selected perfusion containers of the first set and top-up perfusion containers from the second set.

In another embodiment, wherein the dose of Irinotecan for a particular indication is 180 mg/m$^2$ based on patient's body surface area, there is provided following instructions (Table 6) to calculate the total dose to be delivered to a patient based on the body surface area and to select one or more perfusion containers from different sets, to deliver the calculated dose within ±5% variance.

TABLE 6

Description of perfusion system of Irinotecan according to one embodiment:

| | | First Set of Perfusion container (200 ml) (code P) Irinotecan at concentration of 1.5 mg/ml | | Second Set of Top-up perfusion containers (150 ml) (Code S) Irinotecan at concentration of 0.2 mg/ml: | | | |
|---|---|---|---|---|---|---|---|
| Patient BSA* (m$^2$) | Total Target Dose to be delivered (mg) D | Volume of perfusion container (ml) | Dose delivered from perfusion container (a) (mg) | Volume of top up container (ml) | Dose delivered from top-up container (b) (mg) | Total dose delivered (mg) (a + b) | % Variation** from delivered dose Vs calculated dose |
| 1.6 | 288 | 200 | 300 | 0 | 0 | 300 | 4.2 |
| 1.7 | 306 | 200 | 300 | 0 | 0 | 300 | −2.0 |
| 1.8 | 324 | 200 | 300 | 150 | 30 | 330 | 1.9 |
| 1.9 | 342 | 200 | 300 | 150 | 30 | 330 | −3.5 |
| 2.0 | 360 | 200 | 300 | 150 × 2 | 60 | 360 | 0.0 |
| 2.1 | 378 | 200 | 300 | 150 × 2 | 60 | 360 | −4.8 |

**% Variation from delivered dose Vs calculated dose = [((a + b) − D]/D × 100

The perfusion system of above Table (6) is accompanied by suitable instructions for example as below:

| BSA (m²) | Instructions |
|---|---|
| 1.6 and 1.7 | Infuse the full volume from one 200 ml container having an alphabetical code P |
| 1.8 and 1.9 | Infuse the full volume from one 200 ml container having an alphabetical code P and full volume from one 150 ml top-up container having an alphabetical code S |
| 2.0 and 2.1 | Infuse the full volume from one 200 ml container having an alphabetical code P and full volume from two 150 ml top-up containers having an alphabetical code S |

In the above illustration, wherever solution of two bags have to be delivered for the desired dose, the two bags can be connected together via a suitable connector such as a Y connector/joint and the full volume of solution from the two bags can be then infused. In one embodiment, the outlet of the Y joint can be connected to an infusion pump to control the rate of infusion. In this embodiment, only two or three bags are sufficient for delivering the desired calculated dose of irinotecan (within ±5% variance) for a wide range of patient population.

According to one embodiment, there is provided a perfusion system for administration of carboplatin. The Table 7 below provide details of the perfusion system having containers of first, second and/or third set with the ranges of concentration and volume of the solution per set.

TABLE 7

Perfusion system of Carboplatin:

| From set of container of the perfusion system | First set of Perfusion container | Second set of top up perfusion container | Third set of top up perfusion container |
|---|---|---|---|
| Concentration range (mg/ml) | 0.4-5.0 | 0.01-3.0 | 0.01-3.0 |
| Preferred concentration range (mg/ml) | 1.0-3.0 | 0.01-2.0 | 0.01-2.0 |
| Volume range (ml) | 50-1000 | 30-200 | 30-200 |
| Preferred volume range (ml) | 50-500 | 30-100 | 30-100 |

The perfusion system may comprise one or more perfusion containers in the first set and one or more perfusion containers in the second and/or third set. The containers in different sets according to one preferred embodiment of the present invention are given below in Tables 8-10.

TABLE 8

Perfusion containers of the first set having carboplatin:

| Volume of solution in bag (ml) | Perfusion containers of first set | | | | | |
|---|---|---|---|---|---|---|
| | 180 | 200 | 250 | 300 | 350 | 400 |
| Carboplatin amount per bag (mg) (at a concentration of 2 mg/ml) | 360 | 400 | 500 | 600 | 700 | 800 |

TABLE 9

Perfusion containers of the second set having carboplatin:

| | Perfusion containers of second set | | |
|---|---|---|---|
| Volume of solution in bag (ml) | 50 | 40 | 60 |
| Carboplatin amount per bag (mg) (at a concentration of 0.6 mg/ml) | 30 | 24 | 36 |

TABLE 10

Perfusion containers of the third set having carboplatin:

| | Perfusion containers of third set | | |
|---|---|---|---|
| Volume of solution in bag (ml) | 50 | 40 | 60 |
| Carboplatin amount per bag (mg) (at a concentration of 0.4 mg/ml) | 20 | 16 | 24 |

In preferred embodiments, the first set of infusion containers comprise perfusion solution having carboplatin at a concentration ranging from about 0.4 mg/ml to 5.0 mg/ml and volume of solution ranging from about 50 ml to about 1000 ml, further wherein the second or third set of infusion containers comprise perfusion solution having carboplatin at a second and/or third concentration ranging from about 0.01 mg/ml to 2.5 mg/ml and volume of solution ranging from about 30 ml to about 100 ml; further wherein the perfusion solution has a pH ranging from about 3.0 to 7.0.

In one specific embodiment, the dose of carboplatin for a particular indication is 360 mg/m² based on patient's body surface area. There is provided instructions to calculate the total dose to be delivered to a patient based on the body surface area and select one container from the first set and one or more container from the top-up perfusion container to deliver the calculated dose within ±5% variance and is presented in table (11) below:

TABLE 11

Description of perfusion system of carboplatin according to one embodiment:

| | | First set of Perfusion container having carboplatin at 2.0 mg/ml | | Second set of Top-up perfusion containers having carboplatin at 0.8 mg/ml | | | |
|---|---|---|---|---|---|---|---|
| BSA (m²) | Total Target Dose to be delivered D (mg) | Volume of perfusion container (ml) | Dose delivered from perfusion container (a) (mg) | Volume of top up container (ml) | Dose delivered from top-up container (b) (mg) | Total dose delivered (mg) (a + b) | % Variation from delivered dose Vs calculated dose |
| 1.5 | 540.0 | 270 | 540 | 0 | 0 | 0 | 0 |
| 1.6 | 576.0 | 270 | 540 | 65 | 52 | 592 | 2.7 |
| 1.7 | 612.0 | 270 | 540 | 65 | 52 | 592 | -3.3 |
| 1.8 | 648.0 | 330 | 660 | 0 | 0 | 660 | 1.9 |

TABLE 11-continued

Description of perfusion system of carboplatin according to one embodiment:

| | | First set of Perfusion container having carboplatin at 2.0 mg/ml | | Second set of Top-up perfusion containers having carboplatin at 0.8 mg/ml | | | |
|---|---|---|---|---|---|---|---|
| BSA (m²) | Total Target Dose to be delivered D (mg) | Volume of perfusion container (ml) | Dose delivered from perfusion container (a) (mg) | Volume of top up container (ml) | Dose delivered from top-up container (b) (mg) | Total dose delivered (mg) (a + b) | % Variation from delivered dose Vs calculated dose |
| 1.9 | 684.0 | 330 | 660 | 0 | 0 | 660 | −3.5 |
| 2.0 | 720.0 | 330 | 660 | 65 | 52 | 712 | −1.1 |

**% Variation from delivered dose Vs calculated dose = [((a + b) − D]/D × 100
*BSA—Body Surface Area The containers of the perfusion system of Table (11) may be color coded as follows:

| First set of Perfusion containers carboplatin concentration 2.0 mg/ml | | Second set of top-up perfusion containers; carboplatin concentration 0.8 mg/ml: | |
|---|---|---|---|
| Volume of perfusion container (ml) | Alphabetical code | Volume of top up container (ml) | Alphabetical code |
| 270 | A | 65 | C |
| 330 | B | | |

The perfusion system of above Table (11) is accompanied by suitable instructions for example as below:

| BSA (m²) | Instructions |
|---|---|
| 1.5 | Infuse the full volume from one 270 ml container having an alphabetical code A |
| 1.6 and 1.7 | Connect one 270 ml container having an alphabetical code A to one 65 ml top-up container having an alphabetical code C and infuse the full volume |
| 1.8 and 1.9 | Infuse the full volume from one 330 ml container having an alphabetical code B |
| 2.0 | Connect one 330 ml container having an alphabetical code B to one 65 ml top-up container having an alphabetical code C and Infuse the full volume |

In one specific embodiment, the dose of carboplatin for a particular indication is 300 mg/m² based on patient's body surface area. There is provided instructions to calculate the total dose to be delivered to a patient based on the body surface area and select one or more perfusion containers of carboplatin from different sets, to deliver the calculated dose within ±5% variance and is presented in table (12) below:

TABLE 12

Description of perfusion system of carboplatin according to one embodiment:

| | | First set of Perfusion container; Carboplatin concentration—2.0 mg/ml | | Second Set of Top-up perfusion containers; Carboplatin concentration—0.6 mg/ml: | | Third Set of Top-up perfusion containers— Carboplatin concentration—0.4 mg/ml: | | | |
|---|---|---|---|---|---|---|---|---|---|
| BSA* (m²) | Total Target Dose to be delivered (mg) D | Volume of perfusion container (ml) | Dose delivered from perfusion container (a) (mg) | Volume of top up container (ml) | Dose delivered from top-up container (b) (mg) | Volume of top up container (ml) | Dose delivered from top-up container (c) (mg) | Total dose delivered (mg) (a + b + c) | % Variation** from delivered dose Vs calculated dose |
| 1.3 | 390 | 180 | 360 | 50 | 30 | 0 | 0 | 390 | 0.00 |
| 1.4 | 420 | 180 | 360 | 50 | 30 | 50 | 20 | 410 | −2.38 |
| 1.5 | 450 | 200 | 400 | 50 | 30 | 50 | 20 | 450 | 0.00 |
| 1.6 | 480 | 250 | 500 | 0 | 0 | 0 | 0 | 500 | 4.2 |
| 1.7 | 510 | 250 | 500 | 0 | 0 | 0 | 0 | 500 | −2.0 |
| 1.8 | 540 | 250 | 500 | 50 | 30 | 50 | 20 | 550 | 1.9 |
| 1.9 | 570 | 250 | 500 | 50 × 2 | 60 | 0 | 0 | 560 | −1.8 |
| 2.0 | 600 | 300 | 600 | 0 | 0 | 0 | 0 | 600 | 0.00 |
| 2.1 | 630 | 300 | 600 | 50 | 30 | 0 | 0 | 630 | 0.00 |
| 2.2 | 660 | 300 | 600 | 50 | 30 | 50 | 20 | 650 | −1.5 |
| 2.3 | 690 | 350 | 700 | 0 | 0 | 0 | 0 | 0 | 1.4 |
| 2.4 | 720 | 350 | 700 | 0 | 0 | 50 | 20 | 720 | 0.00 |

**% Variation from delivered dose Vs calculated dose = [((a + b + c) − D]/D × 100
*BSA—Body Surface Area The containers of the perfusion system of Table (12) may be color coded as follows:

| First set of Perfusion containers; Carboplatin concentration 2.0 mg/ml | | Second set of top-up perfusion containers; Carboplatin concentration 0.8 mg/ml: | | Third set of top-up perfusion containers; Carboplatin concentration 0.4 mg/ml: | |
|---|---|---|---|---|---|
| Volume of perfusion container (ml) | Alphabetical code | Volume of top up container (ml) | Alphabetical code | Volume of top up container (ml) | Alphabetical code |
| 180 | D | 50 | I | 50 | J |
| 200 | E | | | | |
| 250 | F | | | | |
| 300 | G | | | | |
| 350 | H | | | | |

The perfusion system of Table (12) is accompanied by suitable instructions for example as below:

| BSA ($m^2$) | Instructions |
|---|---|
| 1.3 | Connect one 180 ml container having an alphabetical code D to one 50 ml container having an alphabetical code I and infuse the full volume |
| 1.4 | Connect one 180 ml container having an alphabetical code D + one 50 ml container having an alphabetical code I + one 50 ml container having an alphabetical code J and infuse the full volume |
| 1.5 | Connect one 200 ml container having an alphabetical code E + one 50 ml container having an alphabetical code I band and one 50 ml container having an alphabetical code J and infuse the full volume |
| 1.6 and 1.7 | Infuse the full volume from one 250 ml container having an alphabetical code F |
| 1.8 | Connect one 250 ml container having an alphabetical code F + one 50 ml container having an alphabetical code I + one 50 ml container having an alphabetical code J and infuse the full volume |
| 1.9 | Connect one 250 ml container having an alphabetical code F to two 50 ml container having an alphabetical code I and infuse the full volume |
| 2.0 | Infuse the full volume from one 300 ml container having an alphabetical code G |
| 2.1 | Connect one 300 ml container having an alphabetical code G and one 50 ml container having an alphabetical code I and infuse the full volume |
| 2.2 | Connect one 300 ml container having an alphabetical code G + one 50 ml container having an alphabetical code I + one 50 ml container having an alphabetical code J and infuse the full volume |
| 2.3 | Infuse the full volume from one 350 ml container having an alphabetical code H |
| 2.4 | Connect one 350 ml container having an alphabetical code H to one 50 ml container having an alphabetical code J and infuse the full volume |

In another specific embodiment, the dose of carboplatin for a particular indication is 360 mg/m² based on patient's body surface area. There is provided instructions to calculate the total dose to be delivered to a patient based on the body surface area and select one or more perfusion containers of carboplatin from different sets, to deliver the calculated dose within ±5% variance and is presented in table (13) below:

TABLE 13

Description of perfusion system of carboplatin according to one embodiment:

| | | First set of Perfusion container Carboplatin concentration—2.2 mg/ml: | | Second set of Top-up perfusion containers— Carboplatin concentration—0.6 mg/ml: | | Third set of Top-up perfusion containers— Carboplatin concentration—0.4 mg/ml: | | | |
|---|---|---|---|---|---|---|---|---|---|
| BSA* ($m^2$) | Total Target Dose to be delivered (mg) D | Volume of perfusion container (ml) | Dose delivered from perfusion container (a) (mg) | Volume of top up container (ml) | Dose delivered from top-up container (b) (mg) | Volume of top up container (ml) | Dose delivered from top-up container (c) (mg) | Total dose delivered (a + b + c) | % Variation** from delivered dose Vs calculated dose |
| 1.2 | 432 | 180.0 | 396 | 0 | 0 | 50 | 20 | 416 | −3.7 |
| 1.3 | 468 | 180 | 396 | 100 | 60 | 0 | 0 | 456 | −2.6 |
| 1.4 | 504 | 200 | 440 | 100 | 60 | 0 | 0 | 500 | −0.8 |
| 1.5 | 540 | 250 | 550 | 0 | 0 | 0 | 0 | 550 | 1.9 |
| 1.6 | 576 | 250 | 550 | 0 | 0 | 50 | 20 | 570 | −1.0 |
| 1.7 | 612 | 250 | 550 | 100 | 60 | 0 | 0 | 610 | −0.3 |
| 1.8 | 648 | 300 | 660 | 0 | 0 | 0 | 0 | 660 | 1.9 |
| 1.9 | 684 | 300 | 660 | 0 | 0 | 50 | 20 | 680 | −0.6 |
| 2.0 | 720 | 300 | 660 | 100 | 60 | 0 | 0 | 720 | 0 |
| 2.1 | 756 | 350 | 770 | 0 | 0 | 0 | 0 | 770 | 1.9 |
| 2.2 | 792 | 350 | 770 | 0 | 0 | 50 | 20 | 790 | −0.3 |
| 2.3 | 828 | 350 | 770 | 100 | 60 | 0 | 0 | 830 | 0.2 |
| 2.4 | 864 | 350 | 770 | 100 | 60 | 50 | 20 | 850 | −1.6 |
| 2.6 | 936 | 400 | 880 | 100 | 60 | 0 | 0 | 940 | 0.4 |

**% Variation from delivered dose Vs calculated dose = [((a + b + c) − D]/D × 100

*BSA—Body Surface Area

The containers of the perfusion system of Table (13) may be color coded as follows:

| First set of Perfusion containers; Carboplatin concentration 2.2 mg/ml: | | Second set of top-up perfusion containers; Carboplatin concentration 0.6 mg/ml: | | Third set of top-up perfusion containers; Carboplatin concentration 0.4 mg/ml: | |
|---|---|---|---|---|---|
| Volume of perfusion container (ml) | Alphabetical code | Volume of top up container (ml) | Alphabetical code | Volume of top up container (ml) | Alphabetical code |
| 180 | K | 100 | Q | 50 | R |
| 200 | L | | | | |
| 250 | M | | | | |
| 300 | N | | | | |
| 350 | O | | | | |
| 400 | P | | | | |

The perfusion system of Table (13) is accompanied by suitable instructions for example as below:

| BSA (m$^2$) | Instructions |
|---|---|
| 1.2 | Connect one 180 ml container having an alphabetical code K to one 50 ml container having an alphabetical code R and infuse the full volume |
| 1.3 | Connect one 180 ml container having an alphabetical code K to one 100 ml container having an alphabetical code Q and infuse the full volume |
| 1.4 | Connect one 200 ml container having an alphabetical code L to one 100 ml container having an alphabetical code Q and infuse the full volume |
| 1.5 | Infuse the full volume from one 250 ml container having an alphabetical code M |
| 1.6 | Connect one 250 ml container having an alphabetical code M to one 50 ml container having an alphabetical code R and infuse the full volume |
| 1.7 | Connect one 250 ml container having an alphabetical code M to one 100 ml container having an alphabetical code Q and infuse the full volume |
| 1.8 | Infuse the full volume from one 300 ml container having an alphabetical code N |
| 1.9 | Connect one 300 ml container having an alphabetical code N to one 50 ml container having an alphabetical code R and infuse the full volume |
| 2.0 | Connect one 300 ml container having an alphabetical code N to one 100 ml container having an alphabetical code Q and infuse the full volume |
| 2.1 | Infuse the full volume from one 350 ml container having an alphabetical code O |
| 2.2 | Connect one 350 ml container having an alphabetical code O to one 50 ml container having an alphabetical code R and infuse the full volume |
| 2.3 | Connect one 350 ml container having an alphabetical code O to one 100 ml container having an alphabetical code Q and infuse the full volume |
| 2.4 | Connect one 350 ml container having an alphabetical code O + one 100 ml container having an alphabetical code Q + one 50 ml container having an alphabetical code R and infuse the full volume |
| 2.6 | Connect one 400 ml container with having an alphabetical code P to one 100 ml container having an alphabetical code Q and infuse the full volume |

In one specific embodiment, the dose of carboplatin for a particular indication is 200 mg/m$^2$ based on patient's body surface area. There is provided instructions to calculate the total dose to be delivered to a patient based on the body surface area and select one or more perfusion containers from different sets, to deliver the calculated dose within ±5% variance and is presented in table (14) below:

TABLE 14

Description of perfusion system of carboplatin according to one embodiment:

| | | First set of Perfusion container; Carboplatin concentration—2.0 mg/ml: | | Second set of Top-up perfusion containers; Carboplatin concentration 2.0 mg/ml: | | | |
|---|---|---|---|---|---|---|---|
| BSA* (m$^2$) | Total Target Dose to be delivered D (mg) | Volume of perfusion container (ml) | Dose delivered from perfusion container (a) (mg) | Volume of top up perfusion container (ml) | Dose delivered from top-up perfusion container (b) (mg) | Total dose delivered (mg) (a + b) | % Variation from delivered dose Vs calculated dose |
| 1.6 | 320.0 | 160 | 320.0 | 0 | 0 | 320.0 | 0.0 |
| 1.7 | 340.0 | 125 | 250.0 | 50 | 100 | 350.0 | 2.9 |
| 1.8 | 360.0 | 125 | 250.0 | 50 | 100 | 350.0 | −2.8 |
| 1.9 | 380.0 | 190 | 380.0 | 0 | 0 | 380.0 | 0.0 |
| 2.0 | 400.0 | 125 | 250.0 | 80 | 160 | 410.0 | 2.5 |
| 2.1 | 420.0 | 125 | 250.0 | 80 | 160 | 410.0 | −2.4 |
| 2.2 | 440.0 | 145 | 290.0 | 80 | 160 | 450.0 | 2.3 |
| 2.3 | 460.0 | 145 | 290.0 | 80 | 160 | 450.0 | −2.2 |
| 2.4 | 480.0 | 245 | 490.0 | 0 | 0 | 490.0 | 2.1 |

**% Variation from delivered dose Vs calculated dose = [((a + b + c) − D]/D × 100

* BSA—Body Surface Area

The containers of the perfusion system of Table (14) may be color coded as follows:

| First set of Perfusion containers Carboplatin concentration 2.0 mg/ml | | Second set of top-up perfusion containers; Carboplatin concentration 2.0 mg/ml: | |
| --- | --- | --- | --- |
| Volume of perfusion container (ml) | Color code | Volume of top up container (ml) | Color code |
| 125 | S | 50 | X |
| 160 | T | 80 | Y |
| 190 | U | | |
| 145 | V | | |
| 245 | W | | |

The perfusion system of Table (14) is accompanied by suitable instructions for example as below:

| BSA ($m^2$) | Instructions |
| --- | --- |
| 1.6 | Infuse the full volume from one 160 ml container having an alphabetical code T |
| 1.7 and 1.8 | Connect one 125 ml container having an alphabetical code S to one 50 ml container having an alphabetical code X and infuse the full volume |
| 1.9 | Infuse the full volume from one 190 ml container having an alphabetical code U |
| 2.0 and 2.1 | Connect one 125 ml container having an alphabetical code S and one 80 ml container having an alphabetical code Y and infuse the full volume |
| 2.2 and 2.3 | Connect one 145 ml container having an alphabetical code V to one 80 ml container having an alphabetical code Y and infuse the full volume |
| 2.4 | Infuse the full volume from one 245 ml container having an alphabetical code W |

As described above, the target dose of carboplatin for a person having a specific body surface area can be delivered (within ±5% variance), by the perfusion system of the present invention, by infusing the full volume of solution from the selected perfusion containers of the first set and top-up perfusion containers from the second and/or third set.

According to one embodiment, there is provided a perfusion system for administration of topotecan or its pharmaceutically acceptable salt. Table 15 below provides details of the perfusion system having containers of first, second and/or third set with the ranges of concentration and volume of the solution per set.

TABLE 15

| Perfusion system of topotecan: | | | |
| --- | --- | --- | --- |
| From set of container of the perfusion system | First set of perfusion container | Second set of top up perfusion container | Third set of top up perfusion container |
| Concentration range (mg/ml) | 0.001 to 0.072 | 0.0005-0.003 | 0.003-0.005 |
| Preferred concentration range (mg/ml) | 0.01 | 0.002 | 0.004 |
| Volume range (ml) | 50-500 | 30-200 | 30-200 |
| Preferred volume range (ml) | 50-340 | 50-100 | 50-100 |

The perfusion system may comprise one or more perfusion containers in the first set and one or more perfusion containers in the second and/or third set. The containers in different sets according to one preferred embodiment of the present invention are given below in Tables 16-18.

TABLE 16

| Perfusion containers of the first set having topotecan: | | | | | | | | |
| --- | --- | --- | --- | --- | --- | --- | --- | --- |
| | Perfusion containers of first set | | | | | | | |
| Volume of solution in bag (ml) | 50 | 100 | 160 | 250 | 340 | 400 | 450 | 500 |
| Topotecan amount per bag (mg) (at a concentration of 0.01 mg/ml) | 0.5 | 1.0 | 1.6 | 2.5 | 3.4 | 4.0 | 4.5 | 5.0 |

TABLE 17

| Perfusion containers of the second set having topotecan: | | | | |
| --- | --- | --- | --- | --- |
| | Perfusion containers of second set | | | |
| Volume of solution in bag (ml) | 50 | 75 | 100 | 200 |
| Topotecan amount per bag (mg) (at a concentration of 0.002 mg/ml) | 0.1 | 0.15 | 0.2 | 0.4 |

TABLE 18

| Perfusion containers of the third set having topotecan: | | | |
| --- | --- | --- | --- |
| | Perfusion containers of third set | | |
| Volume of solution in bag (ml) | 50 | 75 | 100 |
| Topotecan amount per bag (mg) (at a concentration of 0.004 mg/ml) | 0.2 | 0.3 | 0.4 |

In one particularly preferred embodiment wherein the antineoplastic drug is topotecan, the first set of infusion containers comprise perfusion solution having topotecan at a concentration ranging from about 0.001 mg/ml to 0.072 mg/ml and volume of solution ranging from about 50 ml to about 500 ml, further wherein the second or third set of infusion containers comprise perfusion solution having topotecan at a concentration ranging from about 0.0005-0.005 mg/ml and volume of solution ranging from about 30 ml to about 100 ml.

In one specific embodiment, the dose of topotecan for a particular indication is 1.5 mg/$m^2$ based on patient's body surface area. There is provided instructions for calculating the total dose to be delivered to a patient based on the body surface area and instructions for selecting one container from the first set and one container from the top-up perfusion container to deliver the calculated dose within ±5% variance and is presented in table (19) below.

TABLE 19

Description of perfusion system of Topotecan according to one embodiment:

| | | First set of Perfusion containers; (250 ml, code A) topotecan concentration 0.01 mg/ml | | Second set of Top-up perfusion containers (50 ml, code B; 200 ml code C); topotecan concentration 0.002 mg/ml: | | | |
|---|---|---|---|---|---|---|---|
| BSA* $(m^2)$ | Total Target Dose to be delivered D (mg) | Volume of perfusion container (ml) | Dose delivered from perfusion container (a) (mg) | Volume of top up container (ml) | Dose delivered from top-up container (b) (mg) | Total dose delivered (mg) (a + b) | % Variation** from delivered dose Vs calculated dose |
| 1.6 | 2.4 | 250 | 2.5 | 0 | 0 | 2.5 | −4.3 |
| 1.7 | 2.55 | 250 | 2.5 | 50 | 0.1 | 2.6 | −2.0 |
| 1.8 | 2.7 | 250 | 2.5 | 50 | 0.1 | 2.6 | −3.7 |
| 1.9 | 2.85 | 250 | 2.5 | 200 | 0.4 | 2.9 | 1.8 |
| 2.0 | 3 | 250 | 2.5 | 200 | 0.4 | 2.9 | −3.3 |

**% Variation from delivered dose Vs calculated dose = [((a + b) − D]/D × 100
*BSA—Body Surface Area The perfusion system of above Table (19) is accompanied by suitable instructions for example as below:

| BSA $(m^2)$ | Instructions |
|---|---|
| 1.6 | Infuse the full volume from one 250 ml container having an alphabetical code A |
| 1.7 and 1.8 | Infuse the full volume from one 250 ml container having an alphabetical code A and full volume from one 50 ml top-up container having an alphabetical code B |
| 1.9 and 2.0 | Infuse the full volume from one 250 ml container having an alphabetical code A and full volume from one 200 ml top-up containers having an alphabetical code C |

In one specific embodiment, the dose of topotecan for a particular indication is 1.5 mg/m² based on patient's body surface area. There is provided instructions for calculating the total dose to be delivered to a patient based on the body surface area and instructions for selecting one or more perfusion containers of topotecan from first set and one or more top-up perfusion container from the second and/or third set of top-up perfusion containers, to deliver the calculated dose within ±5% variance and is presented below in table (20):

TABLE 20

Description of perfusion system of topotecan according to one embodiment:

| | | First set of Perfusion container topotecan concentration 0.01 mg/ml | | Second set of Top-up perfusion containers; topotecan concentration 0.002 mg/ml: | | Third set of Top-up perfusion containers; topotecan concentration 0.004 mg/ml: | | | |
|---|---|---|---|---|---|---|---|---|---|
| BSA* $(m^2)$ | Total Target Dose to be delivered (mg) D | Volume of perfusion container (ml) | Dose delivered from perfusion container (a) (mg) | Volume of top up container (ml) | Dose delivered from top-up container (b) (mg) | Volume of top up container (ml) | Dose delivered from top-up container (c) (mg) | Total dose delivered (mg) (a + b + c) | % Variation** from delivered dose Vs calculated dose |
| 1.4 | 2.1 | 160 | 1.6 | 0 | 0 | 100 | 0.4 | 2.0 | −4.8 |
| 1.5 | 2.25 | 160 | 1.6 | 100 | 0.2 | 100 | 0.4 | 2.2 | −2.2 |
| 1.6 | 2.4 | 250 | 2.5 | 0 | 0 | 0 | 0 | 2.5 | 4.2 |
| 1.7 | 2.55 | 250 | 2.5 | 0 | 0 | 0 | 0 | 2.5 | −2.0 |
| 1.8 | 2.7 | 250 | 2.5 | 100 | 0.2 | 0 | 0 | 2.7 | 0.0 |
| 1.9 | 2.85 | 250 | 2.5 | 0 | 0 | 100 | 0.4 | 2.9 | 1.8 |
| 2 | 3 | 250 | 2.5 | 0 | 0 | 100 | 0.4 | 2.9 | −3.3 |
| 2.1 | 3.15 | 250 | 2.5 | 100 | 0.2 | 100 | 0.4 | 3.1 | −1.6 |
| 2.2 | 3.3 | 340 | 3.4 | 0 | 0 | 0 | 0 | 3.4 | 3.0 |
| 2.3 | 3.45 | 340 | 3.4 | 0 | 0 | 0 | 0 | 3.4 | −1.4 |
| 2.4 | 3.6 | 340 | 3.4 | 100 | 0.2 | 0 | 0 | 3.6 | 0.0 |

**% Variation from delivered dose Vs calculated dose = [((a + b + c) − D]/D × 100
*BSA—Body Surface Area The containers of the perfusion system of Table (20) may be color coded as follows:

| First set of Perfusion containers topotecan concentration 0.01 mg/ml | | Second set of top-up perfusion containers; topotecan concentration 0.002 mg/ml: | | Third set of top-up perfusion containers; topotecan concentration 0.004 mg/ml: | |
|---|---|---|---|---|---|
| Volume of perfusion container (ml) | Alphabetical code | Volume of top up container (ml) | Alphabetical code | Volume of top up container (ml) | Alphabetical code |
| 160 | D | 100 | F | 100 | G |
| 250 | A | | | | |
| 340 | E | | | | |

The perfusion system of Table (20) is accompanied by suitable instructions for example as below:

| BSA (m$^2$) | Instructions |
|---|---|
| 1.4 | Connect one 160 ml container having an alphabetical code D to one 100 ml container having an alphabetical code F and infuse the full volume |
| 1.5 | Infuse the full volume from one 160 ml container having an alphabetical code D+; one 100 ml container having an alphabetical code F + one 100 ml container having an alphabetical code G |
| 1.6 and 1.7 | Infuse the full volume from one 250 ml container having an alphabetical code A |
| 1.8 | Connect one 250 ml container having an alphabetical code A and one 100 ml container having an alphabetical code F and infuse the full volume |
| 1.9 and 2.0 | Connect one 250 ml container having an alphabetical code A and one 100 ml container having an alphabetical code G and infuse the full volume |
| 2.1 | Connect one 250 ml container having an alphabetical code A + one 100 ml container having an alphabetical code G + one 100 ml container having an alphabetical code F and infuse the full volume |
| 2.2 and 2.3 | Infuse the full volume from one 340 ml container having an alphabetical code E |
| 2.4 | Connect one 340 ml container having an alphabetical code E and one 100 ml container having an alphabetical code F and infuse the full volume |

As described above, the target dose of topotecan for a person having a specific body surface area can be delivered (within ±5% variance), by the perfusion system of the present invention, by infusing the full volume of solution from the selected perfusion containers of the first set and top-up perfusion containers from the second and/or third set.

According to the present invention, the below embodiment provides perfusion system for administration of docetaxel or its pharmaceutically acceptable salt. Table 21 below provides details of the perfusion system having containers of first, second and/or third set with the ranges of concentration and volume of the solution per set.

TABLE 21

| Perfusion system of docetaxel | | | |
|---|---|---|---|
| From set of container of the perfusion system | First set of perfusion container | Second set of top up perfusion container | Third set of top up perfusion container |
| Concentration range (mg/ml) | 0.1 to 2 | 0.1 to 2 | 0.1 to 2 |
| Preferred concentration range (mg/ml) | 0.3 to 0.74 | 0.3 to 0.74 | 0.3 to 0.74 |
| Volume range (ml) | 50-800 | 25-150 | 25-100 |
| Preferred volume range (ml) | 50-500 | 50-100 | 50-100 |

The perfusion system may comprise one or more perfusion containers in the first set and one or more perfusion containers in the second and/or third set. The containers in different sets according to one preferred embodiment of the present invention are given below in Tables 22-24.

TABLE 22

| Perfusion containers of the first set having docetaxel: | | | | | | | | | |
|---|---|---|---|---|---|---|---|---|---|
| Volume of solution | Perfusion containers of first set | | | | | | | | |
| in bag (ml) | 185 | 200 | 215 | 230 | 290 | 315 | 395 | 430 | 465 |
| Docetaxel amount per bag (mg) (at a concentration of 0.5 mg/ml) | 92.5 | 100 | 107.5 | 115 | 135 | 157.5 | 197.5 | 215 | 232.5 |

TABLE 23

| Perfusion containers of the second set having docetaxel: | | | | |
|---|---|---|---|---|
| | Perfusion containers of second set | | | |
| Volume of solution in bag (ml) | 50 | 75 | 100 | 150 |
| Docetaxel amount per bag (mg) (at a concentration of 0.3 mg/ml) | 15 | 22.5 | 30 | 45 |

TABLE 24

| Perfusion containers of the third set having docetaxel: | | | | |
|---|---|---|---|---|
| | Perfusion containers of third set | | | |
| Volume of solution in bag (ml) | 50 | 75 | 100 | 150 |
| Docetaxel amount per bag (mg) (at a concentration of 0.15 mg/ml) | 7.5 | 11.25 | 15.0 | 22.5 |

In one particularly preferred embodiment wherein the antineoplastic drug is docetaxel, the first set of infusion containers comprise perfusion solution having docetaxel at a concentration ranging from about 0.1 mg/ml to 2.0 mg/ml and volume of solution ranging from about 50 ml to about 800 ml, further wherein the second or third set of infusion containers comprise perfusion solution having Docetaxel at a concentration ranging from about 0.1-2.0 mg/ml and volume of solution ranging from about 25 ml to about 150 ml.

In one specific embodiment, the dose of docetaxel for a particular indication is 100 mg/m$^2$ based on patient's body surface area. There is provided instructions to calculate the total dose to be delivered to a patient based on the body surface area and select one or more perfusion containers from different sets to deliver the calculated dose within ±5% variance and is presented in table (25) below.

TABLE 25

Description of perfusion system of Docetaxel according to one embodiment:

| BSA* ($m^2$) | Total Target Dose to be delivered (mg) D | First set of Perfusion container; Docetaxel concentration 0.6 mg/ml | | Second set of Top-up perfusion containers; Docetaxel concentration 0.3 mg/ml: | | Third set of Top-up perfusion containers; Docetaxel concentration 0.15 mg/ml: | | Total dose delivered (mg) (a + b + c) | % Variation** from delivered dose Vs calculated dose |
|---|---|---|---|---|---|---|---|---|---|
| | | Volume of perfusion container (ml) | Dose delivered from perfusion container (a) (mg) | Volume of top up container (ml) | Dose delivered from top-up container (b) (mg) | Volume of top up container (ml) | Dose delivered from top-up container (c) (mg) | | |
| 1.6 | 160.0 | 270 | 162 | 0 | 0 | 0 | 0 | 162.00 | 1.3 |
| 1.7 | 170.0 | 270 | 162 | 0 | 0 | 50 | 7.5 | 169.50 | −0.3 |
| 1.8 | 180.0 | 290 | 174 | 50 | 15 | 0 | 0 | 189.00 | 5.0 |
| 1.9 | 190.0 | 290 | 174 | 50 | 15 | 0 | 0 | 189.00 | −0.5 |
| 2 | 200.0 | 340 | 204 | 0 | 0 | 0 | 0 | 204.00 | 2.0 |
| 2.1 | 210.0 | 340 | 204 | 50 | 15 | 0 | 0 | 219.00 | 4.3 |
| 2.2 | 220.0 | 340 | 204 | 50 | 15 | 0 | 0 | 219.00 | −0.5 |
| 2.3 | 230.0 | 340 | 204 | 50 | 15 | 50 | 7.5 | 226.50 | −1.5 |
| 2.4 | 240.0 | 395 | 237 | 0 | 0 | 0 | 0 | 237.00 | −1.3 |

**% Variation from delivered dose Vs calculated dose = [((a + b + c) − D]/D × 100

The containers of the perfusion system of Table (25) may be alphabetically coded as follows:

| First set of Perfusion containers; docetaxel concentration 0.6 mg/ml | | Second set of top-up perfusion containers; docetaxel concentration 0.3 mg/ml: | | Third set of top-up perfusion containers; docetaxel concentration 0.15 mg/ml: | |
|---|---|---|---|---|---|
| Volume of perfusion container (ml) | Alphabetical code | Volume of top up container (ml) | Alphabetical code | Volume of top up container (ml) | Alphabetical code |
| 270 | A | 50 | E | 50 | F |
| 290 | B | | | | |
| 340 | C | | | | |
| 395 | D | | | | |

The perfusion system of Table (25) is accompanied by suitable instructions for example as below:

| BSA ($m^2$) | Instructions |
|---|---|
| 1.6 | Infuse the full volume from one 270 ml container having an alphabetical code A |
| 1.7 | Connect one 270 ml container having an alphabetical code A to one 50 ml container having an alphabetical code E and infuse the full volume |
| 1.8 and 1.9 | Connect one 290 ml container having an alphabetical code B to one 50 ml container having an alphabetical code E and infuse the full volume |
| 2.0 | Infuse the full volume from one 340 ml container having an alphabetical code C |
| 2.1 and 2.2 | Connect one 340 ml container having an alphabetical code C and one 50 ml container having an alphabetical code E and infuse the full volume |
| 2.3 | Connect one 340 ml container having an alphabetical code C + one 50 ml container having an alphabetical code E + one 50 ml container having an alphabetical code F and infuse the full volume |
| 2.4 | Infuse the full volume from one 395 ml container having an alphabetical code D |

In one specific embodiment, the dose of docetaxel for a particular indication is 55 mg/$m^2$ based on patient's body surface area. There is provided instructions to calculate the total dose to be delivered to a patient based on the body surface area and select one container from the first set and one or more container from the top-up perfusion container to deliver the calculated dose within ±5% variance and is presented in table (26) below.

TABLE 26

Description of perfusion system of Docetaxel according to one embodiment:

| BSA* ($m^2$) | Total Target Dose to be delivered (mg) D | First set of Perfusion container: Docetaxel concentration 0.3 mg/ml | | Second set of Top-up perfusion containers; Docetaxel concentration 0.3 mg/ml: | | Total dose delivered (mg) (a + b) | % Variation** from delivered dose Vs calculated dose |
|---|---|---|---|---|---|---|---|
| | | Volume of perfusion container (ml) | Dose delivered from perfusion container (a) (mg) | Volume of top up container (ml) | Dose delivered from top-up container (b) (mg) | | |
| 1.3 | 71.5 | 200 | 60 | 50 | 15 | 75.00 | 4.9 |
| 1.4 | 77.0 | 200 | 60 | 50 | 15 | 75.00 | −2.6 |
| 1.5 | 82.5 | 270 | 81.00 | 0 | 0 | 81.00 | −1.8 |
| 1.6 | 88.0 | 290 | 87.00 | 0 | 0 | 87.00 | −1.1 |
| 1.7 | 93.5 | 315 | 94.50 | 0 | 0 | 94.50 | 1.1 |
| 1.8 | 99.0 | 290 | 87.00 | 50 | 15 | 102.00 | 3.0 |
| 1.9 | 104.5 | 290 | 87.00 | 50 | 15 | 102.00 | −2.4 |
| 2 | 110.0 | 365 | 109.50 | 0 | 0 | 109.50 | −0.5 |

TABLE 26-continued

Description of perfusion system of Docetaxel according to one embodiment:

| | | First set of Perfusion container: Docetaxel concentration 0.3 mg/ml | | Second set of Top-up perfusion containers; Docetaxel concentration 0.3 mg/ml: | | | |
|---|---|---|---|---|---|---|---|
| BSA* ($m^2$) | Total Target Dose to be delivered (mg) D | Volume of perfusion container (ml) | Dose delivered from perfusion container (a) (mg) | Volume of top up container (ml) | Dose delivered from top-up container (b) (mg) | Total dose delivered (mg) (a + b) | % Variation** from delivered dose Vs calculated dose |
| 2.1 | 115.5 | 395 | 118.50 | 0 | 0 | 118.50 | 2.6 |
| 2.2 | 121.0 | 395 | 118.50 | 0 | 0 | 118.50 | −2.1 |

**% Variation from delivered dose Vs calculated dose = [((a + b) − D]/D × 100
*BSA—Body Surface Area The containers of the perfusion system of Table (26) may be alphabetically coded as follows:

| First set of Perfusion containers; docetaxel concentration 0.3 mg/ml | | Second set of top-up perfusion containers; docetaxel concentration 0.3 mg/ml: | |
|---|---|---|---|
| Volume of perfusion container (ml) | Alphabetical code | Volume of top up container (ml) | Alphabetical code |
| 200 | G | 50 | E |
| 270 | A | | |
| 290 | B | | |
| 315 | H | | |
| 365 | I | | |
| 395 | J | | |

The perfusion system of Table (26) is accompanied by suitable instructions for example as below:

| BSA ($m^2$) | Instructions |
|---|---|
| 1.3 and 1.4 | Connect one 200 ml container having an alphabetical code G to one 50 ml container having an alphabetical code pink band and infuse the full volume |
| 1.5 | Infuse the full volume from one 270 ml container having an alphabetical code A |
| 1.6 | Infuse the full volume from one 290 ml container having an alphabetical code B |
| 1.7 | Infuse the full volume from one 315 ml container having an alphabetical code H |
| 1.8 and 1.9 | Connect one 290 ml container having an alphabetical code B and one 50 ml container having an alphabetical code and infuse the full volume |
| 2.0 | Infuse the full volume from one 365 ml container having an alphabetical code I |
| 2.1 and 2.2 | Infuse the full volume from one 395 ml container having an alphabetical code J |

As described above, the target dose of docetaxel for a person having a specific body surface area can be delivered (within ±5% variance), by the perfusion system of the present invention, by infusing the full volume of solution from the selected perfusion containers of the first set and top-up perfusion containers from the second and/or third set.

According to the present invention, the below embodiment provides perfusion system for administration of cisplatin. Table 27 below provides details of the perfusion system having containers of first, second and/or third set with the ranges of concentration and volume of the solution per set.

TABLE 27

Perfusion system of Cisplatin:

| From set of container of the perfusion system | First set of perfusion container | Second set of top up perfusion container | Third set of top up perfusion container |
|---|---|---|---|
| Concentration range (mg/ml) | 0.03-0.8 | 0.005-0.5 | 0.005-0.5 |
| Preferred concentration range (mg/ml) | 0.1-0.8 | 0.005 0.08 | 0.005-0.08 |
| Volume range (ml) | 50-1000 | 10-500 | 10-500 |
| Preferred volume range (ml) | 50-900 | 20-100 | 20-100 |

The perfusion system may comprise one or more perfusion containers in the first set and one or more perfusion containers in the second and/or third set. The containers in different sets according to one preferred embodiment of the present invention are given below in Tables 28-30.

TABLE 28

Perfusion containers of the first set having cisplatin:

| | Perfusion containers of first set | | | | |
|---|---|---|---|---|---|
| Volume of solution in bag (ml) | 500 | 600 | 700 | 800 | 900 |
| Cisplatin amount per bag (mg) (at a concentration of 0.13 mg/ml) | 65 | 78 | 91 | 104 | 117 |

TABLE 29

Perfusion containers of the second set having cisplatin:

| | Perfusion containers of second set | | |
|---|---|---|---|
| Volume of solution in bag (ml) | 50 | 60 | 100 |
| Cisplatin amount per bag (mg) (at a concentration of 0.05 mg/ml) | 2.5 | 3.0 | 5.0 |

TABLE 30

Perfusion containers of the third set having cisplatin:

| | Perfusion containers of third set | | |
|---|---|---|---|
| Volume of solution in bag (ml) | 40 | 50 | 60 |
| Cisplatin amount per bag (mg) (at a concentration of 0.03 mg/ml) | 1.2 | 1.5 | 1.8 |

In one particular embodiment of the present invention wherein the antineoplastic drug is cisplatin, the first set of infusion containers comprise perfusion solution having cisplatin at a concentration ranging from about 0.03 mg/ml to 0.8 mg/ml and volume of solution ranging from about 50 ml to about 1000 ml, further wherein the second or third set of infusion containers comprise perfusion solution having cisplatin at a concentration ranging from about 0.005 mg/ml to 0.08 mg/ml and volume of solution ranging from about 20 ml to about 100 ml; further wherein the perfusion solution has a pH ranging from about 3.0 to 7.0.

According to one embodiment, the dose for a particular indication is 50 mg/m$^2$ based on body surface area as the patient parameter. There is provided instructions to calculate the dose based on the body surface area and select one or more perfusion containers of cisplatin from different sets, to deliver the calculated dose within ±5% variance and is presented in table (31) below:

TABLE 31

Description of perfusion system of cisplatin:

| BSA (m$^2$) | Total Target Dose to be delivered (mg) D | First set of Perfusion container; Cisplatin concentration 0.13 mg/ml: | | Second set of Top-up perfusion containers; Cisplatin concentration 0.05 mg/ml: | | Third set of Top-up perfusion container; Cisplatin concentration 0.03 mg/ml: | | Total dose delivered (mg) (a + b + c) | % Variation** from delivered dose Vs calculated dose |
|---|---|---|---|---|---|---|---|---|---|
| | | Volume of perfusion container (ml) | Dose delivered from perfusion container (a) (mg) | Volume of top up container (ml) | Dose delivered from top-up container (b) (mg) | Volume of top up perfusion container (ml) | Dose delivered from top-up container (c) (mg) | | |
| 1.3 | 65 | 500 | 65 | 0 | 0 | 0 | 0 | 65 | 0 |
| 1.4 | 70 | 500 | 65 | 100 | 5 | 0 | 0 | 70 | 0 |
| 1.5 | 75 | 600 | 78 | 0 | 0 | 0 | 0 | 78 | 3.8 |
| 1.6 | 80 | 600 | 78 | 0 | 0 | 0 | 0 | 78 | −2.5 |
| 1.7 | 85 | 600 | 78 | 100 | 5 | 0 | 0 | 83 | −2.4 |
| 1.8 | 90 | 700 | 91 | 0 | 0 | 0 | 0 | 91 | 1.1 |
| 1.9 | 95 | 700 | 91 | 100 | 5 | 0 | 0 | 96 | 1.0 |
| 2.0 | 100 | 700 | 91 | 100 | 5 | 50 | 1.5 | 97.5 | −2.6 |
| 2.1 | 105 | 800 | 104 | 0 | 0 | 0 | 0 | 104 | −0.9 |
| 2.2 | 110 | 800 | 104 | 100 | 5 | 0 | 0 | 109 | −0.9 |
| 2.3 | 115 | 900 | 117 | 0 | 0 | 0 | 0 | 117 | 1.7 |
| 2.4 | 120 | 900 | 117 | 0 | 0 | 50 | 1.5 | 118.5 | −1.3 |
| 2.6 | 130 | 500 × 2 | 130 | 0 | 0 | 0 | 0 | 130 | 0.0 |

**% Variation from delivered dose Vs calculated dose = [((a + b + c) − D]/D × 100

The containers of the perfusion system of Table (31) may be alphabetical coded as follows:

| First set of Perfusion containers; cisplatin concentration 0.13 mg/ml | | Second set of top-up perfusion containers; cisplatin concentration 0.05 mg/ml: | | Third set of top-up perfusion containers; cisplatin concentration 0.03 mg/ml: | |
|---|---|---|---|---|---|
| Volume of perfusion container (ml) | Alphabetical code | Volume of top up container (ml) | Alphabetical code | Volume of top up container (ml) | Alphabetical code |
| 500 | A | 100 | F | 50 | G |
| 600 | B | | | | |
| 700 | C | | | | |
| 800 | D | | | | |
| 900 | E | | | | |

The perfusion system of Table (31) is accompanied by suitable instructions for example as below:

| BSA (m²) | Instructions |
|---|---|
| 1.3 | Infuse the full volume from one 500 ml container having an alphabetical code A |
| 1.4 | Connect one 500 ml container having an alphabetical code A to one 100 ml container having an alphabetical code F and infuse the full volume |
| 1.5 and 1.6 | Infuse the full volume from one 600 ml container having an alphabetical code B |
| 1.7 | Connect one 600 ml container having an alphabetical code B to one 100 ml container having an alphabetical code F and infuse the full volume |
| 1.8 | Infuse the full volume from one 700 ml container having an alphabetical code C |
| 1.9 | Connect one 700 ml container having an alphabetical code C to one 100 ml container having an alphabetical code F and infuse the full volume |
| 2.0 | Connect one 700 ml container having an alphabetical code C + one 100 ml container having an alphabetical code F + one 50 ml container having an alphabetical code G and infuse the full volume |
| 2.1 | Infuse the full volume from one 800 ml container having an alphabetical code D |
| 2.2 | Connect one 800 ml container having an alphabetical code D to one 100 ml container having an alphabetical code F and infuse the full volume |
| 2.3 | Infuse the full volume from one 900 ml container having an alphabetical code E |
| 2.4 | Connect one 900 ml container having an alphabetical code E to one 50 ml container having an alphabetical code G and infuse the full volume |
| 2.6 | Infuse the full volume from two 500 ml container having an alphabetical code A |

According to another embodiment, the table (32) below gives instructions for calculation of the dose and instructions for selecting one or more perfusion containers of cisplatin from different sets, at a dose of 100 mg/m², in accordance with body surface area as the patient parameter, to deliver the calculated dose within ±5% variance:

TABLE 32

Description of perfusion system of cisplatin:

| | | First set of Perfusion container; Cisplatin concentration—0.26 mg/ml: | | Second set of Top-up perfusion containers; Cisplatin concentration—0.10 mg/ml: | | | |
|---|---|---|---|---|---|---|---|
| BSA (m²) | Total Target Dose to be delivered (mg) D | Volume of perfusion container (ml) | Dose delivered from perfusion container (a) (mg) | Volume of top up container (ml) | Dose delivered from top-up container (b) (mg) | Total dose delivered (mg) (a + b) | % Variation** from delivered dose Vs calculated dose |
| 1.3 | 130 | 500 | 130 | 0 | 0 | 130 | 0.0 |
| 1.4 | 140 | 500 | 130 | 100 | 10 | 140 | 0.0 |
| 1.5 | 150 | 600 | 156 | 0 | 0 | 156 | 4.0 |
| 1.6 | 160 | 600 | 156 | 50 | 5 | 161 | 0.6 |
| 1.7 | 170 | 600 | 156 | 100 | 10 | 166 | −2.4 |
| 1.8 | 180 | 700 | 182 | 0 | 0 | 182 | 1.1 |
| 1.9 | 190 | 700 | 182 | 100 | 10 | 192 | 1.1 |
| 2 | 200 | 700 | 182 | 100 | 10 | 192 | −4.0 |
| 2.1 | 210 | 800 | 208 | 0 | 0 | 208 | −0.9 |
| 2.2 | 220 | 800 | 208 | 100 | 10 | 218 | −0.9 |
| 2.3 | 230 | 900 | 234 | 0 | 0 | 234 | 1.7 |
| 2.4 | 240 | 900 | 234 | 50 | 5 | 239 | −0.4 |
| 2.6 | 260 | 1000.0 | 260 | 0 | 0 | 260 | 0.00 |

**% Variation from delivered dose Vs calculated dose = [((a + b) − D]/D × 100

The containers of the perfusion system of Table (32) may be alphabetical coded as follows:

| First set of Perfusion containers; cisplatin concentration 0.13 mg/ml | | Second set of top-up perfusion containers; cisplatin concentration 0.05 mg/ml: | |
|---|---|---|---|
| Volume of perfusion container (ml) | Alphabetical code | Volume of top up container (ml) | Alphabetical code |
| 500 | H | 50 | N |
| 600 | I | 100 | O |
| 700 | J | | |
| 800 | K | | |
| 900 | L | | |
| 1000 | M | | |

The perfusion system of Table (32) is accompanied by suitable instructions for example as below:

| BSA (m$^2$) | Instructions |
|---|---|
| 1.3 | Infuse the full volume from one 500 ml container having an alphabetical code H |
| 1.4 | Connect one 500 ml container having an alphabetical code H to one 100 ml container having an alphabetical code O and infuse the full volume |
| 1.5 | Infuse the full volume from one 600 ml container having an alphabetical code I |
| 1.6 | Connect one 600 ml container having an alphabetical code I to one 50 ml container having an alphabetical code N and infuse the full volume |
| 1.7 | Connect one 600 ml container having an alphabetical code I to one 100 ml container having an alphabetical code O and infuse the full volume |
| 1.8 | Infuse the full volume from one 700 ml container having an alphabetical code J |
| 1.9 and 2.0 | Connect one 700 ml container having an alphabetical code J to one 100 ml container having an alphabetical code O and infuse the full volume |
| 2.1 | Infuse the full volume from one 800 ml container having an alphabetical code K |
| 2.2 | Connect one 800 ml container having an alphabetical code K to one 100 ml container having an alphabetical code O and infuse the full volume |
| 2.3 | Infuse the full volume from one 900 ml container having an alphabetical code L |
| 2.4 | Connect one 900 ml container having an alphabetical code L to one 50 ml container having an alphabetical code N and infuse the full volume |
| 2.6 | Infuse the full volume from one 1000 ml container having an alphabetical code M |

As described above, the target dose of docetaxel for a person having a specific body surface area can be delivered (within ±5% variance), by the perfusion system of the present invention, by infusing the full volume of solution from the selected perfusion containers of the first set and top-up perfusion containers from the second and/or third set.

According to the present invention, the below embodiment provides perfusion system for administration of oxaliplatin. Table 33 below provides details of the perfusion system having containers of first, second and/or third set with the ranges of concentration and volume of the solution per set.

TABLE 33

Perfusion system of Oxaliplatin:

| From set of container of the perfusion system | First set of perfusion container | Second set of top up perfusion container | Third set of top up perfusion container |
|---|---|---|---|
| Concentration range (mg/ml) | 0.4-2.0 | 0.05-1.25 | 0.05-1.25 |
| Preferred concentration range (mg/ml) | 0.6-1.0 | 0.1-0.5 | 0.1-0.5 |
| Volume range (ml) | 50-1000 | 25-500 | 25-500 |
| Preferred volume range (ml) | 70-500 | 25-100 | 25-100 |

The perfusion system may comprise one or more perfusion containers in the first set and one or more perfusion containers in the second and/or third set. The containers in different sets according to one preferred embodiment of the present invention are given below in Table 34-36:

TABLE 34

Perfusion containers of the first set having oxaliplatin:

| | Perfusion containers of first set | | | | |
|---|---|---|---|---|---|
| Volume of solution in bag (ml) | 150 | 180 | 220 | 260 | 300 |
| Oxaliplatin amount per bag (mg) (at a concentration of 0.7 mg/ml) | 105 | 126 | 154 | 182 | 210 |

TABLE 35

Perfusion containers of the second set having oxaliplatin

| | Perfusion containers of second set | | |
|---|---|---|---|
| Volume of solution in bag (ml) | 50 | 40 | 60 |
| Oxaliplatin amount per bag (mg) (at a concentration of 0.15 mg/ml) | 7.5 | 6.0 | 9.0 |

TABLE 36

Perfusion containers of the third set having oxaliplatin

| | Perfusion containers of third set | | |
|---|---|---|---|
| Volume of solution in bag (ml) | 50 | 40 | 60 |
| Oxaliplatin amount per bag (mg) (at a concentration of 0.10 mg/ml) | 5.0 | 4.0 | 6.0 |

In one particular embodiment of the present invention wherein the antineoplastic drug is oxaliplatin, the first set of infusion containers comprise perfusion solution having oxaliplatin at a concentration ranging from about 0.4 mg/ml to 2.0 mg/ml and volume of solution ranging from about 50 ml to about 1000 ml, further wherein the second or third set of infusion containers comprise perfusion solution having oxaliplatin at a concentration ranging from about 0.05 mg/ml to 0.25 mg/ml and volume of solution ranging from about 20 ml to about 100 ml; further wherein the perfusion solution has a pH ranging from about 3.0 to 7.0.

According to one embodiment, the antineoplastic drug is oxaliplatin and the dose for a particular indication is 85 mg/m$^2$ based on body surface area as the patient parameter.

There is provided instructions to calculate the dose based on the body surface area of the patient and select appropriately one or more perfusion containers of oxaliplatin from different sets, to deliver the calculated dose within ±5% variance and is presented in table (37) below:

TABLE 37

Description of perfusion system of oxaliplatin:

| BSA* ($m^2$) | Total Target Dose to be delivered (mg) D | First set of Perfusion container Oxaliplatin concentration— 0.7 mg/ml: | | Second set of Top-up perfusion containers; Oxaliplatin concentration— 0.15 mg/ml: | | Total dose delivered (a + b) | % Variation** from delivered dose Vs calculated dose |
|---|---|---|---|---|---|---|---|
| | | Volume of perfusion container (ml) | Dose delivered from perfusion container (a) (mg) | Volume of top up container (ml) | Dose delivered from top-up container (b) (mg) | | |
| 1.2 | 102 | 150 | 105 | 0 | 0 | 105 | 2.9 |
| 1.4 | 119 | 150 | 105 | 100 | 15 | 120 | 0.8 |
| 1.5 | 127.5 | 180 | 126 | 0 | 0 | 126 | −1.2 |
| 1.6 | 136 | 180 | 126 | 50 | 7.5 | 133.5 | −1.8 |
| 1.7 | 144.5 | 180 | 126 | 100 | 15 | 141 | −2.4 |
| 1.8 | 153 | 220 | 154 | 0 | 0 | 154 | 0.7 |
| 1.9 | 161.5 | 220 | 154 | 50 | 7.5 | 161.5 | 0.0 |
| 2.0 | 170 | 220 | 154 | 100 | 15 | 169 | −0.6 |
| 2.1 | 178.5 | 260 | 182 | 0 | 0 | 182 | 1.96 |
| 2.2 | 187 | 260 | 182 | 50 | 7.5 | 189.5 | 1.3 |
| 2.3 | 195.5 | 260 | 182 | 100 | 15 | 197 | 0.8 |
| 2.4 | 204 | 260 | 182 | 100 | 15 | 19 | −3.4 |
| 2.6 | 221 | 300 | 210 | 100 | 15 | 225 | 1.8 |

**% Variation from delivered dose Vs calculated dose = [((a + b) − D]/D × 100
*BSA—Body Surface Area The containers of the perfusion system of Table (37) may be alphabetical coded as follows:

| First set of Perfusion containers; oxaliplatin concentration 0.7 mg/ml | | Second set of top-up perfusion containers; oxaliplatin concentration 0.15 mg/ml: | |
|---|---|---|---|
| Volume of perfusion container (ml) | Alphabetical code | Volume of top up container (ml) | Alphabetical code |
| 150 | A | 50 | F |
| 180 | B | 100 | G |
| 220 | C | | |
| 260 | D | | |
| 300 | E | | |

The perfusion system of Table (37) is accompanied by suitable instructions for example as below:

| BSA ($m^2$) | Instructions |
|---|---|
| 1.2 | Infuse the full volume from one 150 ml container having an alphabetical code A |
| 1.4 | Connect one 150 ml container having an alphabetical code A to one 100 ml container having an alphabetical code G and infuse the full volume |
| 1.5 | Infuse the full volume from one 180 ml container having an alphabetical code B |
| 1.6 | Connect one 180 ml container having an alphabetical code B to one 50 ml container having an alphabetical code F and infuse the full volume |
| 1.7 | Connect one 180 ml container having an alphabetical code B to one 100 ml container having an alphabetical code G and infuse the full volume |
| 1.8 | Infuse the full volume from one 220 ml container having an alphabetical code C |
| 1. | Connect one 220 ml container having an alphabetical code C to one 50 ml container having an alphabetical code F and infuse the full volume |
| 2.0 | Connect one 220 ml container having an alphabetical code C to one 100 ml container having an alphabetical code G and infuse the full volume |
| 2.1 | Infuse the full volume from one 260 ml container having an alphabetical code D |
| 2.2 | Connect one 260 ml container having an alphabetical code D to one 50 ml container having an alphabetical code F and infuse the full volume |
| 2.3 and 2.4 | Connect one 260 ml container having an alphabetical code D to one 100 ml container having an alphabetical code G and infuse the full volume |
| 2.6 | Connect one 300 ml container having an alphabetical code E to one 100 ml container having an alphabetical code G and infuse the full volume |

According to another embodiment, the table (38) below gives instructions for calculating the dose and instructions for selecting one or more perfusion containers of oxaliplatin from different sets, at a dose of 85 mg/$m^2$, in accordance with body surface area as the patient parameter, to deliver the calculated dose within ±5% variance:

TABLE 38

Description of perfusion system of oxaliplatin:

| | | First set of Perfusion container oxaliplatin concentration— 0.7 mg/ml: | | Second set of Top-up perfusion containers; oxaliplatin concentration 0.7 mg/ml: | | Third set of Top-up perfusion containers; oxaliplatin concentration 0.7 mg/ml: | | | |
|---|---|---|---|---|---|---|---|---|---|
| BSA ($m^2$) | Total Target Dose to be delivered (mg) D | Volume of perfusion container (ml) | Dose delivered from perfusion container (a) (mg) | Volume of top up container (ml) | Dose delivered from top-up container (b) (mg) | Volume of top up perfusion container (ml) | Dose delivered from top-up container (c) (mg) | Total dose delivered (a + b + c) | % Variation** from delivered dose Vs calculated dose |
| 1.2 | 102 | 100 | 70 | 50 | 35 | 0 | 0 | 105 | 2.9 |
| 1.3 | 110.5 | 100 | 70 | 50 | 35 | 0 | 0 | 105 | -4.97 |
| 1.4 | 119 | 120 | 84 | 50 | 35 | 0 | 0 | 119 | 0.0 |
| 1.5 | 127.5 | 130 | 91 | 50 | 35 | 0 | 0 | 126 | -1.2 |
| 1.6 | 136 | 145 | 102 | 50 | 35 | 0 | 0 | 137 | 0.4 |
| 1.7 | 144.5 | 160 | 112 | 50 | 35 | 0 | 0 | 147 | 1.7 |
| 1.8 | 153 | 160 | 112 | 50 | 35 | 0 | 0 | 147 | -3.9 |
| 1.9 | 161.5 | 170 | 119 | 50 | 35 | 0 | 0 | 154 | -4.6 |
| 2 | 170 | 145 | 102 | 0 | 0 | 100 | 70 | 172 | 1.2 |
| 2.1 | 178.5 | 160 | 112 | 0 | 0 | 100 | 70 | 182 | 2.0 |
| 2.2 | 187 | 160 | 112 | 0 | 0 | 100 | 70 | 182 | -2.7 |
| 2.3 | 195.5 | 180 | 126 | 0 | 0 | 100 | 70 | 196 | 0.3 |
| 2.4 | 204 | 180 | 126 | 0 | 0 | 100 | 70 | 196 | -3.9 |
| 2.5 | 212.5 | 160 | 112 | 50 | 35 | 100 | 70 | 217 | 2.1 |
| 2.6 | 221 | 180 | 126 | 50 | 35 | 100 | 70 | 231 | 4.5 |

**% Variation from delivered dose Vs calculated dose = [((a + b + c) − D]/D × 100

The containers of the perfusion system of Table (38) may be alphabetical coded as follows:

| First set of Perfusion containers; oxaliplatin concentration 0.7 mg/ml | | Second set of top-up perfusion containers; oxaliplatin concentration 0.7 mg/ml: | | Third set of top-up perfusion containers; oxaliplatin concentration 0.7 mg/ml: | |
|---|---|---|---|---|---|
| Volume of perfusion container (ml) | Alphabetical code | Volume of top up container (ml) | Alphabetical code | Volume of top up container (ml) | Alphabetical code |
| 100 | H | 50 | N | 100 | O |
| 120 | I | | | | |
| 130 | J | | | | |
| 145 | K | | | | |
| 160 | L | | | | |
| 170 | M | | | | |
| 180 | B | | | | |

The perfusion system of Table (38) is accompanied by suitable instructions for example as below:

| BSA ($m^2$) | Instructions |
|---|---|
| 1.2 and 1.3 | Connect one 100 ml container having an alphabetical code H and one 50 ml container having an alphabetical code N and infuse the full volume |
| 1.4 | Connect one 120 ml container having an alphabetical code I and one 50 ml container having an alphabetical code pink and infuse the full volume |
| 1.5 | Connect one 130 ml container having an alphabetical code J and one 50 ml container having an alphabetical code J and infuse the full volume |
| 1.6 | Connect one 145 ml container having an alphabetical code K and one 50 ml container having analphabetical code N and infuse the full volume |
| 1.7 and 1.8 | Connect one 160 ml container having an alphabetical code L and one 50 ml container having an alphabetical code N and infuse the full volume |
| 1.9 | Connect one 170 ml container having an alphabetical code M and one 50 ml container having an alphabetical code N and infuse the full volume |
| 2.0 | Connect one 145 ml container having an alphabetical code K and one 100 ml container having an alphabetical code O and infuse the full volume |
| 2.1 and 2.2 | Connect one 160 ml container having an alphabetical code L and one 100 ml container having analphabetical code O and infuse the full volume |
| 2.3 and 2.4 | Connect one 180 ml container having an alphabetical code B and one 100 ml container having analphabetical code O and infuse the full volume |
| 2.5 | Connect one 160 ml container having an alphabetical code L + one 50 ml container having analphabetical code N + one 100 ml container having an alphabetical code O and infuse the full volume |
| 2.6 | Connect one 180 ml container having an alphabetical code B + one 50 ml container having analphabetical code N + one 100 ml container having an alphabetical code O and infuse the full volume |

According to the instructions, one or more perfusion containers can be selected from first, second and/or third set of perfusion containers to deliver the calculated target dose within ±5% of variation.

According to the present invention, the below embodiment provides perfusion system for administration of vinorelbine or its pharmaceutically acceptable salt such as vinorelbine tartrate. Table 39 below provides details of the perfusion system having containers of first, second and/or third set with the ranges of concentration and volume of the solution per set.

TABLE 39

Perfusion system of Vinorelbine:

| From set of container of the perfusion system | First set of perfusion container | Second set of top up perfusion container | Third set of top up perfusion container |
|---|---|---|---|
| Concentration range (mg/ml) | 0.2-2.5 | 0.01-1.25 | 0.01-1.25 |
| Preferred concentration range (mg/ml) | 0.5-1.5 | 0.01-0.8 | 0.01-0.8 |
| Volume range (ml) | 25-1000 | 20-500 | 20-500 |
| Preferred volume range (ml) | 60-600 | 20-100 | 20-100 |

The perfusion system may comprise one or more perfusion containers in the first set and one or more perfusion containers in the second and/or third set. The containers in different sets according to one preferred embodiment of the present invention are given below in Tables 40-42.

TABLE 40

Perfusion containers of the first set having vinorelbine:

| | Perfusion containers of first set | | | | | |
|---|---|---|---|---|---|---|
| Volume of solution in bag (ml) | 70 | 80 | 100 | 120 | 140 | 160 |
| Vinorelbine amount per bag (mg) (at a concentration of 0.5 mg/ml) | 35 | 40 | 50 | 60 | 70 | 80 |

TABLE 41

Perfusion containers of the second set having vinorelbine:

| | Perfusion containers of second set | | |
|---|---|---|---|
| Volume of solution in bag (ml) | 40 | 50 | 60 |
| Vinorelbine amount per bag (mg) (at a concentration of 0.05 mg/ml) | 2 | 2.5 | 3 |

TABLE 42

Perfusion containers of the third set having vinorelbine:

| | Perfusion containers of third set | |
|---|---|---|
| Volume of solution in bag (ml) | 40 | 50 |
| Vinorelbine amount per bag (mg) (at a concentration of 0.025 mg/ml) | 1 | 1.25 |

In one particular embodiment of the present invention wherein the antineoplastic drug is vinorelbine, the first set of infusion containers comprise perfusion solution having vinorelbine at a concentration ranging from about 0.2 mg/ml to 2.5 mg/ml and volume of solution ranging from about 50 ml to about 1000 ml, further wherein the second or third set of infusion containers comprise perfusion solution having vinorelbine at a concentration ranging from about 0.01 mg/ml to 1.25 mg/ml and volume of solution ranging from about 20 ml to about 100 ml; further wherein the perfusion solution has a pH ranging from about 3.8 to 5.0.

According to one embodiment, the dose of vinorelbine for a particular indication is 30 mg/m$^2$ based on body surface area as the patient parameter. There is provided instructions to calculate the dose based on the body surface area of the patient and select one or more perfusion containers of vinorelbine from different sets, to deliver the calculated dose within ±5% variance and is presented in table (43) below:

TABLE 43

Description of perfusion system of vinorelbine:

| BSA (m$^2$) | Total Target Dose to be delivered (mg) D | First set of Perfusion container Vinorelbine concentration— 0.5 mg/ml | | Second set of Top-up perfusion containers; Vinorelbine concentration— 0.05 mg/ml | | Third set of Top-up perfusion containers; Vinorelbine concentration— 0.025 mg/ml | | Total dose delivered (mg) (a + b + c) | % Variation** from delivered dose Vs calculated dose |
|---|---|---|---|---|---|---|---|---|---|
| | | Volume of perfusion container (ml) | Dose delivered from perfusion container (a) (mg) | Volume of top up container (ml) | Dose delivered from top-up container (b) (mg) | Volume of top up container (ml) | Dose delivered from top-up container (c) (mg) | | |
| 1.4 | 42 | 80 | 40 | 40 | 2 | 0 | 0 | 42 | 0 |
| 1.5 | 45 | 90 | 45 | 0 | 0 | 0 | 0 | 45 | 0 |
| 1.6 | 48 | 90 | 45 | 40 | 2 | 40 | 1 | 48 | 0 |
| 1.7 | 51 | 100 | 50 | 0 | 0 | 40 | 1 | 51 | 0 |
| 1.8 | 54 | 100 | 50 | 40 × 2 | 4 | 0 | 0 | 54 | 0 |
| 1.9 | 57 | 110 | 55 | 40 | 2 | 0 | 0 | 57 | 0 |
| 2.0 | 60 | 120 | 60 | 0 | 0 | 0 | 0 | 60 | 0 |
| 2.1 | 63 | 120 | 60 | 40 | 2 | 40 | 1 | 63 | 0 |
| 2.2 | 66 | 130 | 65 | 0 | 0 | 40 | 1 | 66 | 0 |
| 2.3 | 69 | 130 | 65 | 40 × 2 | 4 | 0 | 0 | 69 | 0 |
| 2.4 | 72 | 140 | 70 | 40 | 2 | 0 | 0 | 72 | 0 |
| 2.5 | 75 | 150 | 75 | 0 | 0 | 0 | 0 | 75 | 0 |
| 2.6 | 78 | 150 | 75 | 40 | 2 | 40 | 1 | 78 | 0 |

**% Variation from delivered dose Vs calculated dose = [((a + b + c) − D]/D × 100

The containers of the perfusion system of Table (43) may be alphabetical coded as follows:

| First set of Perfusion containers; vinorelbine concentration 0.5 mg/ml | | Second set of top-up perfusion containers; vinorelbine concentration 0.05 mg/ml: | | Third set of top-up perfusion containers; vinorelbine concentration 0.025 mg/ml: | |
|---|---|---|---|---|---|
| Volume of perfusion container (ml) | Alphabetical code | Volume of top up container (ml) | Alphabetical code | Volume of top up container (ml) | Alphabetical code |
| 80 | A | 40 | I | 40 | J |
| 90 | B | | | | |
| 100 | C | | | | |
| 110 | D | | | | |
| 120 | E | | | | |
| 130 | F | | | | |
| 140 | G | | | | |
| 150 | H | | | | |

The perfusion system of Table (43) is accompanied by suitable instructions for example as below:

| BSA (m²) | Instructions |
|---|---|
| 1.4 | Connect one 80 ml container having an alphabetical code A and one 40 ml container having an alphabetical code I and infuse the full volume |
| 1.5 | Infuse the full volume from one 90 ml container having an alphabetical code B |
| 1.6 | Connect one 90 ml container having an alphabetical code B + one 40 ml container having an alphabetical code I + one 40 ml container having an alphabetical code J and infuse the full volume |
| 1.7 | Connect one 100 ml container having an alphabetical code C and one 40 ml container having an alphabetical code J and infuse the full volume |
| 1.8 | Connect one 100 ml container having an alphabetical code C and two 40 ml container having an alphabetical code I and infuse the full volume |
| 1.9 | Connect one 110 ml container having an alphabetical code D and one 40 ml container having an alphabetical code I and infuse the full volume |
| 2.0 | Infuse the full volume from one 120 ml container having an alphabetical code E |
| 2.1 | Connect one 120 ml container having an alphabetical code E + one 40 ml container having an alphabetical code I + one 40 ml container having an alphabetical code J and infuse the full volume |
| 2.2 | Connect one 130 ml container having an alphabetical code F and one 40 ml container having an alphabetical code J and infuse the full volume |
| 2.3 | Connect one 130 ml container having an alphabetical code F and two 40 ml container having an alphabetical code I and infuse the full volume |
| 2.4 | Connect one 140 ml container having an alphabetical code G and one 40 ml container having an alphabetical code I and infuse the full volume |
| 2.5 | Infuse the full volume from one 150 ml container having an alphabetical code H |
| 2.6 | Connect one 150 ml container having an alphabetical code H + one 40 ml container having an alphabetical code I and one 40 ml container having an alphabetical code J and infuse the full volume |

According to the instructions, one or more perfusion containers can be selected from first, second and/or third set of perfusion containers to deliver the calculated target dose within ±5% of variation.

According to the present invention, the below embodiment provides perfusion system for administration of pemetrexed or its pharmaceutically acceptable salt such as pemetrexed disodium heptahydrate. Table 44 below provides details of the perfusion system having containers of first, second and/or third set with the ranges of concentration and volume of the solution per set.

TABLE 44

Perfusion system of pemetrexed:

| From set of container of the perfusion system | First set of perfusion container | Second set of top up perfusion container | Third set of top up perfusion container |
|---|---|---|---|
| Concentration range (mg/ml) | 0.2-20.0 | 0.01-10.0 | 0.01-10.0 |
| Preferred concentration range (mg/ml) | 1.0-11.0 | 0.02-5.0 | 0.01-5.0 |
| Volume range (ml) | 25-1000 | 20-500 | 20-500 |
| Preferred volume range (ml) | 50-600 | 20-100 | 20-100 |

The perfusion system may comprise one or more perfusion containers in the first set and one or more perfusion containers in the second and/or third set. The containers in different sets according to one preferred embodiment of the present invention are given below in Tables 45-47.

TABLE 45

Perfusion containers of the first set having Pemetrexed:

| Volume of solution in bag (ml) | Perfusion containers of first set | | | | | |
|---|---|---|---|---|---|---|
| | 100 | 120 | 140 | 170 | 200 | 250 |
| Pemetrexed amount per bag (mg) (at a concentration of 5.0 mg/ml) | 500 | 600 | 700 | 850 | 1000 | 1250 |

TABLE 46

Perfusion containers of the second set having Pemetrexed:

| | Perfusion containers of second set | | | |
|---|---|---|---|---|
| Volume of solution in bag (ml) | 25 | 40 | 50 | 60 |
| Pemetrexed amount per bag (mg) (at a concentration of 1.0 mg/ml) | 25 | 40 | 50 | 60 |

TABLE 47

Perfusion containers of the third set having Pemetrexed:

| | Perfusion containers of third set | | | |
|---|---|---|---|---|
| Volume of solution in bag (ml) | 20 | 25 | 40 | 50 |
| Pemetrexed amount per bag (mg) (at a concentration of 0.5 mg/ml) | 10 | 12.5 | 20 | 25 |

In one particularly preferred embodiment wherein the antineoplastic drug is pemetrexed, the first set of infusion containers comprise perfusion solution having pemetrexed at a concentration ranging from about 0.2 mg/ml to 20.0 mg/ml and volume of solution ranging from about 25 ml to about 1000 ml, further wherein the second or third set of infusion containers comprise perfusion solution having pemetrexed at a concentration ranging from about 0.01 mg/ml to 10.0 mg/ml and volume of solution ranging from about 20 ml to about 100 ml, further wherein the perfusion solution has a pH ranging from about 6.0 to 8.0.

In one embodiment, the dose of pemetrexed for a particular indication is 500 mg/m² based on patient's body surface area. There is provided instructions for calculating the dose based on the body surface area and instructions for selecting one or more perfusion containers of pemetrexed from different sets, to deliver the calculated dose within ±5% variance and is presented in table (48):

TABLE 48

Description of perfusion system of pemetrexed:

| | | First set of Perfusion container Pemetrexed concentration—5.0 mg/ml | | Second set of Top-up perfusion containers; Pemetrexed concentration 1.0 mg/ml | | | |
|---|---|---|---|---|---|---|---|
| BSA (m²) | Total Target Dose to be delivered (mg) D | Volume of perfusion container (ml) | Dose delivered from perfusion container (a) (mg) | Volume of top up container (ml) | Dose delivered from top-up container (b) (mg) | Total dose delivered (mg) (a + b + c) | % Variation** from delivered dose Vs calculated dose |
| 1.2 | 600 | 100 | 500 | 50 × 2 | 100 | 600 | 0.0 |
| 1.3 | 650 | 120 | 600 | 50 | 50 | 650 | 0.0 |
| 1.4 | 700 | 140 | 700 | 0 | 0 | 700 | 0.0 |
| 1.5 | 750 | 140 | 700 | 50 | 50 | 750 | 0.0 |
| 1.6 | 800 | 140 | 700 | 50 × 2 | 100 | 800 | 0.0 |
| 1.7 | 850 | 170 | 850 | 0 | 0 | 850 | 0.0 |
| 1.8 | 900 | 170 | 850 | 50 | 50 | 900 | 0.0 |
| 1.9 | 950 | 170 | 850 | 50 × 2 | 100 | 950 | 0.0 |
| 2.0 | 1000 | 200 | 1000 | 0 | 0 | 1000 | 0.0 |
| 2.1 | 1050 | 200 | 1000 | 50 | 50 | 1050 | 0.0 |
| 2.2 | 1100 | 200 | 1000 | 50 × 2 | 100 | 1100 | 0.0 |
| 2.3 | 1150 | 200 | 1000 | 50 × 2 | 100 | 1100 | −4.3 |
| 2.4 | 1200 | 250 | 1250 | 0 | 0 | 1250 | 4.2 |
| 2.5 | 1250 | 250 | 1250 | 0 | 0 | 1250 | 0.0 |
| 2.6 | 1300 | 250 | 1250 | 50 | 50 | 1300 | 0.0 |

**% Variation from delivered dose Vs calculated dose = [((a + b + c) − D]/D × 100

The containers of the perfusion system of Table (48) may be alphabetical coded as follows:

| First set of Perfusion containers; pemetrexed concentration 5.0 mg/ml | | Second set of top-up perfusion containers; pemetrexed concentration 1.0 mg/ml | |
|---|---|---|---|
| Volume of perfusion container (ml) | Alphabetical code | Volume of top up container (ml) | Alphabetical code |
| 100 | A | 50 | G |
| 120 | B | | |
| 140 | C | | |
| 170 | D | | |
| 200 | E | | |
| 250 | F | | |

The perfusion system of Table (48) is accompanied by suitable instructions for example as below:

| BSA (m²) | Instructions |
|---|---|
| 1.2 | Connect one 100 ml container having an alphabetical code A and two 50 ml container having an alphabetical code G and infuse the full volume |
| 1.3 | Connect one 120 ml container having an alphabetical code B and one 50 ml container having an alphabetical code G |
| 1.4 | Infuse the full volume from one 140 ml container having an alphabetical code C |
| 1.5 | Connect from one 140 ml container having an alphabetical code C and one 50 ml container having an alphabetical code G and infuse the full volume |
| 1.6 | Connect one 140 ml container having an alphabetical code C and two 50 ml container having an alphabetical code G and infuse the full volume |

-continued

| BSA (m²) | Instructions |
|---|---|
| 1.7 | Infuse the full volume from one 170 ml container having an alphabetical code D |
| 1.8 | Connect one 170 ml container having an alphabetical code D and one 50 ml container having an alphabetical code G and infuse the full volume |
| 1.9 | Connect one 170 ml container having an alphabetical code D and two 50 ml container having an alphabetical code G and infuse the full volume |
| 2.0 | Infuse the full volume from one 200 ml container having an alphabetical code E |
| 2.1 | Connect one 200 ml container having an alphabetical code E and one 50 ml container having an alphabetical code G and infuse the full volume |
| 2.2 and 2.3 | Connect one 200 ml container having an alphabetical code E and two 50 ml container having an alphabetical code G and infuse the full volume |
| 2.4 and 2.5 | Infuse the full volume from one 250 ml container having an alphabetical code F |
| 2.6 | Connect one 250 ml container having an alphabetical code F and one 50 ml container having an alphabetical code G and infuse the full volume |

According to the instructions, one or more perfusion containers can be selected from first, second and/or third set of perfusion containers to deliver the calculated target dose within ±5% of variation.

According to the present invention, the below embodiment provides perfusion system for administration of gemcitabine or its pharmaceutically acceptable salt such as gemcitabine hydrochloride. Table 49 below provides details of the perfusion system having containers of first, second and/or third set with the ranges of concentration and volume of the solution per set.

TABLE 49

Perfusion system of gemcitabine:

| From set of container of the perfusion system | First set of perfusion container | Second set of top up perfusion container | Third set of top up perfusion container |
|---|---|---|---|
| Concentration range (mg/ml) | 0.1-15.0 | 0.005-7.5 | 0.005-7.5 |
| Preferred concentration range (mg/ml) | 1.0-10.0 | 0.01-5.0 | 0.01-5.0 |
| Volume range (ml) | 80-2000 | 20-800 | 20-800 |
| Preferred volume range (ml) | 100-1000 | 50-200 | 50-200 |

The perfusion system may comprise one or more perfusion containers in the first set and one or more perfusion containers in the second and/or third set. The containers in different sets according to one preferred embodiment of the present invention are given below in Tables 50-52.

TABLE 50

Perfusion containers of first set having gemcitabine:

| | Perfusion containers of first set | | | | | |
|---|---|---|---|---|---|---|
| Volume of solution in bag (ml) | 100 | 120 | 150 | 180 | 210 | 240 |
| Gemcitabine amount per bag (mg) (at a concentration of 10 mg/ml) | 1000 | 1200 | 1500 | 1800 | 2100 | 2400 |

TABLE 51

Perfusion containers of second set having gemcitabine:

| | Perfusion containers of second set | | | |
|---|---|---|---|---|
| Volume of solution in bag (ml) | 25 | 50 | 80 | 100 |
| Gemcitabine amount per bag (mg) (at a concentration of 2.0 mg/ml) | 50 | 100 | 160 | 200 |

TABLE 52

Perfusion containers of the third set having gemcitabine:

| | Perfusion containers of third set | | | |
|---|---|---|---|---|
| Volume of solution in bag (ml) | 20 | 25 | 50 | 100 |
| Gemcitabine amount per bag (mg) (at a concentration of 1.0 mg/ml) | 20 | 25 | 50 | 100 |

In one particularly preferred embodiment wherein the antineoplastic drug is gemcitabine, the first set of infusion containers comprise perfusion solution having gemcitabine at a concentration ranging from about 0.1 mg/ml to 15.0 mg/ml and volume of solution ranging from about 25 ml to about 2000 ml, further wherein the second or third set of infusion containers comprise perfusion solution having gemcitabine at a concentration ranging from about 0.005 mg/ml to 7.5 mg/ml and volume of solution ranging from about 20 ml to about 100 ml, further wherein the perfusion solution has a pH ranging from about 6.0 to 8.0.

According to one embodiment, the dose of gemcitabine for a particular indication is 1000 mg/m² based on body surface area. There is provided instructions for calculating the dose and instructions for selecting one or more perfusion containers of gemcitabine from different sets, to deliver the calculated dose within ±5% variance and is presented in table (53) below:

TABLE 53

Description of perfusion system of gemcitabine:

| | | First set of Perfusion container Gemcitabine concentration 10 mg/ml | | Second set of Top-up perfusion containers; Gemcitabine concentration 2 mg/ml: | | Third Set of Top-up perfusion containers; Gemcitabine concentration 1 mg/ml | | | |
|---|---|---|---|---|---|---|---|---|---|
| BSA ($m^2$) | Total Target Dose to be delivered (mg) D | Volume of perfusion container (ml) | Dose delivered from perfusion container (a) (mg) | Volume of top up container (ml) | Dose delivered from top-up container (b) (mg) | Volume of top up container (ml) | Dose delivered from top-up container (c) (mg) | Total dose delivered (mg) (a + b + c) | % Variation** from delivered dose Vs calculated dose |
| 1.2 | 1200 | 100 | 1000 | 100 | 200 | 0 | 0 | 1200 | 0.0 |
| 1.3 | 1300 | 120 | 1200 | 0 | 0 | 100 | 100 | 1300 | 0.0 |
| 1.4 | 1400 | 120 | 1200 | 100 | 200 | 0 | 0 | 1400 | 0.0 |
| 1.5 | 1500 | 120 | 1200 | 100 | 200 | 100 | 100 | 1500 | 0.0 |
| 1.6 | 1600 | 150 | 1500 | 0 | 0 | 100 | 100 | 1600 | 0.0 |
| 1.7 | 1700 | 150 | 1500 | 100 | 200 | 0 | 0 | 1700 | 0.0 |
| 1.8 | 1800 | 150 | 1500 | 100 | 200 | 100 | 100 | 1800 | 0.0 |
| 1.9 | 1900 | 180 | 1800 | 0 | 0 | 100 | 100 | 1900 | 0.0 |
| 2.0 | 2000 | 180 | 1800 | 100 | 200 | 0 | 0 | 2000 | 0.0 |
| 2.1 | 2100 | 210 | 2100 | 0 | 0 | 0 | 0 | 2100 | 0.0 |
| 2.2 | 2200 | 210 | 2100 | 0 | 0 | 100 | 100 | 2200 | 0.0 |
| 2.3 | 2300 | 210 | 2100 | 100 | 200 | 0 | 0 | 2300 | 0.0 |
| 2.4 | 2400 | 210 | 2100 | 100 | 200 | 100 | 100 | 2400 | 0.0 |
| 2.5 | 2500 | 240 | 2400 | 0 | 0 | 100 | 100 | 2500 | 0.0 |
| 2.6 | 2600 | 240 | 2400 | 100 | 200 | 0 | 0 | 2600 | 0.0 |

**% Variation from delivered dose Vs calculated dose = [((a + b + c) − D]/D × 100

The containers of the perfusion system of Table (53) may be alphabetically coded as follows:

| First set of Perfusion containers; gemcitabine concentration 10 mg/ml | | Second set of top-up perfusion containers; gemcitabine concentration 2 mg/ml | | Third set of top-up perfusion containers; gemcitabine concentration 1 mg/ml: | |
|---|---|---|---|---|---|
| Volume of perfusion container (ml) | Alpha-betical code | Volume of top up container (ml) | Alpha-betical code | Volume of top up container (ml) | Alpha-betical code |
| 100 | A | 100 | G | 100 | H |
| 120 | B | | | | |
| 150 | C | | | | |
| 180 | D | | | | |
| 210 | E | | | | |
| 240 | F | | | | |

The perfusion system of Table (53) is accompanied by suitable instructions for example as below:

| BSA (m$^2$) | Instructions |
|---|---|
| 1.2 | Connect one 100 ml container having an alphabetical code A and one 100 ml container having an alphabetical code G and infuse the full volume |
| 1.3 | Connect one 100 ml container having an alphabetical code A and one 100 ml container having an alphabetical code H and infuse the full volume |
| 1.4 | Connect one 120 ml container having an alphabetical code B and one 100 ml container having an alphabetical code G and infuse the full volume |
| 1.5 | Connect one 120 ml container having an alphabetical code B + one 100 ml container having an alphabetical code G + one 100 ml container having an alphabetical code H and infuse the full volume |
| 1.6 | Connect one 150 ml container having an alphabetical code C and one 100 ml container having an alphabetical code H and infuse the full volume |
| 1.7 | Connect one 150 ml container having an alphabetical code C and one 100 ml container having an alphabetical code G and infuse the full volume |
| 1.8 | Connect one 150 ml container having an alphabetical code C + one 100 ml container having an alphabetical code G + one 100 ml container having an alphabetical code H and infuse the full volume |
| 1.9 | Connect one 180 ml container having an alphabetical code D + one 100 ml container having an alphabetical code H and infuse the full volume |
| 2.0 | Connect one 180 ml container having an alphabetical code D and one 100 ml container having an alphabetical code G and infuse the full volume |
| 2.1 | Infuse the full volume from one 210 ml container having an alphabetical code E |
| 2.2 | Connect one 210 ml container having an alphabetical code E and one 100 ml container having an alphabetical code H and infuse the full volume |
| 2.3 | Connect one 210 ml container having an alphabetical code E and one 100 ml container having an alphabetical code G and infuse the full volume |
| 2.4 | Connect one 210 ml container having an alphabetical code E + one 100 ml container having an alphabetical code G + one 100 ml container having an alphabetical code H and infuse the full volume |
| 2.5 | Connect one 240 ml container having an alphabetical code F + one 100 ml container having an alphabetical code H and infuse the full volume |
| 2.6 | Connect one 240 ml container having an alphabetical code F + one 100 ml container having an alphabetical code G and infuse the full volume |

According to the instructions, one or more perfusion containers can be selected from first, second and/or third set of perfusion containers to deliver the calculated target dose within ±5% of variation.

According to yet another embodiment for gemcitabine at a dose is 1000 mg/m$^2$ in accordance with body surface area as the patient parameter, the table (54) below provides instructions for calculation of the dose and instructions for selecting one or more perfusion containers of gemcitabine from different sets, to deliver the calculated dose within ±5% variance:

(54): Description of perfusion system of gemcitabine:

| BSA (m$^2$) | Total Target Dose to be delivered (mg) D | First set of Perfusion container Gemcitabine concentration 10 mg/ml | | Second set of Top-up perfusion containers; Gemcitabine concentration 4 mg/ml: | | Third Set of Top-up perfusion containers; Gemcitabine concentration 4 mg/ml | | Total dose delivered (mg) (a + b + c) | % Variation** from delivered dose Vs calculated dose |
|---|---|---|---|---|---|---|---|---|---|
| | | Volume of perfusion container (ml) | Dose delivered from perfusion container (a) (mg) | Volume of top up container (ml) | Dose delivered from top-up container (b) (mg) | Volume of top up container (ml) | Dose delivered from top-up container (c) (mg) | | |
| 1.2 | 1200 | 100 | 1000 | 50 | 200 | 0 | 0 | 1200 | 0.0 |
| 1.3 | 1300 | 120 | 1200 | 0 | 0 | 25 | 100 | 1300 | 0.0 |
| 1.4 | 1400 | 120 | 1200 | 50 | 200 | 0 | 0 | 1400 | 0.0 |
| 1.5 | 1500 | 120 | 1200 | 50 | 200 | 25 | 100 | 1500 | 0.0 |
| 1.6 | 1600 | 150 | 1500 | 0 | 0 | 25 | 100 | 1600 | 0.0 |
| 1.7 | 1700 | 150 | 1500 | 50 | 200 | 0 | 0 | 1700 | 0.0 |
| 1.8 | 1800 | 150 | 1500 | 50 | 200 | 25 | 100 | 1800 | 0.0 |
| 1.9 | 1900 | 180 | 1800 | 0 | 0 | 25 | 100 | 1900 | 0.0 |
| 2.0 | 2000 | 180 | 1800 | 50 | 200 | 0 | 0 | 2000 | 0.0 |
| 2.1 | 2100 | 210 | 2100 | 0 | 0 | 0 | 0 | 2100 | 0.0 |
| 2.2 | 2200 | 210 | 2100 | 0 | 0 | 25 | 100 | 2200 | 0.0 |
| 2.3 | 2300 | 210 | 2100 | 50 | 200 | 0 | 0 | 2300 | 0.0 |
| 2.4 | 2400 | 210 | 2100 | 50 | 200 | 25 | 100 | 2400 | 0.0 |
| 2.5 | 2500 | 240 | 2400 | 0 | 0 | 25 | 100 | 2500 | 0.0 |
| 2.6 | 2600 | 240 | 2400 | 50 | 200 | 0 | 0 | 2600 | 0.0 |

**% Variation from delivered dose Vs calculated dose = [((a + b + c) − D]/D × 100

The containers of the perfusion system of Table (54) may be alphabetical coded as follows:

| First set of Perfusion containers; gemcitabine concentration 10 mg/ml | | Second set of top-up perfusion containers; vinblastine concentration 4 mg/ml | | Third set of top-up perfusion containers; vinblastine concentration 4 mg/ml: | |
|---|---|---|---|---|---|
| Volume of perfusion container (ml) | Alphabetical code | Volume of top up container (ml) | Alphabetical code | Volume of top up container (ml) | Alphabetical code |
| 100 | A | 50 | I | 25 | J |
| 120 | B | | | | |
| 150 | C | | | | |
| 180 | D | | | | |
| 210 | E | | | | |
| 240 | F | | | | |

The perfusion system of Table (54) is accompanied by suitable instructions for example as below:

| BSA ($m^2$) | Instructions |
|---|---|
| 1.2 | Connect one 100 ml container having an alphabetical code A and one 50 ml container having an alphabetical code I and infuse the full volume |
| 1.3 | Connect one 120 ml container having an alphabetical code B + one 25 ml container having an alphabetical code J and infuse the full volume |
| 1.4 | Connect one 120 ml container having an alphabetical code B + one 50 ml container having an alphabetical code I and infuse the full volume |
| 1.5 | Connect one 120 ml container having an alphabetical code B + one 50 ml container having an alphabetical code I + one 25 ml container having an alphabetical code J and infuse the full volume |
| 1.6 | Connect one 150 ml container having an alphabetical code C + one 25 ml container having an alphabetical code J and infuse the full volume |
| 1.7 | Connect one 150 ml container having an alphabetical code C + one 50 ml container having an alphabetical code I and infuse the full volume |
| 1.8 | Connect one 150 ml container having an alphabetical code C + one 50 ml container having an alphabetical code I + one 25 ml container having an alphabetical code J and infuse the full volume |
| 1.9 | Connect one 180 ml container having an alphabetical code D + one 25 ml container having an alphabetical code J and infuse the full volume |
| 2.0 | Connect one 180 ml container having an alphabetical code D + one 50 ml container having an alphabetical code I and infuse the full volume |
| 2.1 | Infuse the full volume from one 210 ml container having an alphabetical code E |
| 2.2 | Connect one 210 ml container having an alphabetical code E + one 25 ml container having an alphabetical code J and infuse the full volume |
| 2.3 | Connect one 210 ml container having an alphabetical code E + one 50 ml container having an alphabetical code I and infuse the full volume |
| 2.4 | Connect one 210 ml container having an alphabetical code E + one 50 ml container having an alphabetical code I + one 25 ml container having an alphabetical code J and infuse the full volume |
| 2.5 | Connect one 240 ml container having an alphabetical code F + one 25 ml container having an alphabetical code J and infuse the full volume |
| 2.6 | Connect one 240 ml container having an alphabetical code F + one 50 ml container having an alphabetical code I and infuse the full volume |

According to the instructions, one or more perfusion containers can be selected from first, second and/or third set of perfusion containers to deliver the calculated target dose within ±5% of variation.

According to yet another embodiment for gemcitabine, the dose for a particular indication is 1000 mg/m² in accordance with body surface area as the patient parameter. The table (55) below provides instruction for calculation of total dose to be delivered to a patient based on the body surface area and instructions for selecting one or more perfusion containers of gemcitabine from different sets, to deliver the calculated dose within ±5% variance:

TABLE 55

Description of perfusion system of gemcitabine:

| | | First set of Perfusion container Gemcitabine concentration 10 mg/ml | | Second set of Top-up perfusion containers; Gemcitabine concentration 10 mg/ml: | | | |
|---|---|---|---|---|---|---|---|
| BSA ($m^2$) | Total Target Dose to be delivered (mg) D | Volume of perfusion container (ml) | Dose delivered from perfusion container (a) (mg) | Volume of top up container (ml) | Dose delivered from top-up container (b) (mg) | Total dose delivered (mg) (a + b) | % Variation** from delivered dose Vs calculated dose |
| 1.2 | 1200 | 120 | 1200 | 0 | 0 | 1200.00 | 0.00 |
| 1.3 | 1300 | 130 | 1300 | 0 | 0 | 1300.00 | 0.00 |
| 1.4 | 1400 | 140 | 1400 | 0 | 0 | 1400.00 | 0.00 |
| 1.5 | 1500 | 150 | 1500 | 0 | 0 | 1500.00 | 0.00 |
| 1.6 | 1600 | 160 | 1600 | 0 | 0 | 1600.00 | 0.00 |
| 1.7 | 1700 | 170 | 1700 | 0 | 0 | 1700.00 | 0.00 |
| 1.8 | 1800 | 180 | 1800 | 0 | 0 | 1800.00 | 0.00 |
| 1.9 | 1900 | 190 | 1900 | 0 | 0 | 1900.00 | 0.00 |
| 2 | 2000 | 200 | 2000 | 0 | 0 | 2000.00 | 0.00 |
| 2.1 | 2100 | 200 | 2000 | 0 | 0 | 2000.00 | −4.76 |
| 2.2 | 2200 | 220 | 2200 | 0 | 0 | 2200.00 | 0.00 |
| 2.3 | 2300 | 220 | 2200 | 0 | 0 | 2200.00 | −4.35 |
| 2.4 | 2400 | 120 | 1200 | 120 | 1200 | 2400.00 | 0.00 |
| 2.5 | 2500 | 130 | 1300 | 120 | 1200 | 2500.00 | 0.00 |
| 2.6 | 2600 | 130 | 1300 | 130 | 1300 | 2600.00 | 0.00 |

***% Variation from delivered dose Vs calculated dose = [((a + b + c) − D]/D × 100

The containers of the perfusion system of Table (55) may be alphabetical coded as follows:

| First set of Perfusion containers; gemcitabine concentration 10 mg/ml | | Second set of top-up perfusion containers; vinblastine concentration 4 mg/ml | | Third set of top-up perfusion containers; vinblastine concentration 4 mg/ml: | |
|---|---|---|---|---|---|
| Volume of perfusion container (ml) | Alphabetical code | Volume of top up container (ml) | Alphabetical code | Volume of top up container (ml) | Alphabetical code |
| 120 | B | 120 | B | 130 | K |
| 130 | K | | | | |
| 140 | L | | | | |
| 150 | C | | | | |
| 160 | M | | | | |
| 170 | N | | | | |
| 180 | D | | | | |
| 190 | O | | | | |
| 200 | P | | | | |
| 220 | Q | | | | |

The perfusion system of Table (55) is accompanied by suitable instructions for example as below:

| BSA ($m^2$) | Instructions |
|---|---|
| 1.2 | Infuse the full volume from one 120 ml container having an alphabetical code B |
| 1.3 | Infuse the full volume from one 130 ml container having an alphabetical code K |
| 1.4 | Infuse the full volume from one 140 ml container having an alphabetical code L |
| 1.5 | Infuse the full volume from one 150 ml container having an alphabetical code C |
| 1.6 | Infuse the full volume from one 160 ml container having an alphabetical code M |
| 1.7 | Infuse the full volume from one 170 ml container having an alphabetical code N |
| 1.8 | Infuse the full volume from one 180 ml container having an alphabetical code D |
| 1.9 | Infuse the full volume from one 190 ml container having an alphabetical code O |
| 2.0 and 2.1 | Infuse the full volume from one 200 ml container having an alphabetical code P |
| 2.2 and 2.3 | Infuse the full volume from one 220 ml container having an alphabetical code Q |
| 2.4 | Connect two 120 ml container having an alphabetical code B and infuse the full volume |
| 2.5 | Connect one 130 ml container having an alphabetical code K + one 120 ml container having an alphabetical code B and infuse the full volume |
| 2.6 | Connect two 130 ml container having an alphabetical code K and infuse the full volume |

According to yet another embodiment for gemcitabine, the dose for a particular indication is 1250 mg/$m^2$ in accordance with body surface area as the patient parameter. The table (56) below provides instruction for calculation of total dose to be delivered to a patient based on the body surface area and instructions for selecting one or more perfusion containers of gemcitabine from different sets, to deliver the calculated dose within ±5% variance:

TABLE 56

| Description of perfusion system of gemcitabine: | | | | | | | |
|---|---|---|---|---|---|---|---|
| | | First set of Perfusion container Gemcitabine concentration 10 mg/ml | | Second set of Top-up perfusion containers; Gemcitabine concentration 10 mg/ml: | | | |
| BSA ($m^2$) | Total Target Dose to be delivered (mg) D | Volume of perfusion container (ml) | Dose delivered from perfusion container (a) (mg) | Volume of top up container (ml) | Dose delivered from top-up container (b) (mg) | Total dose delivered (mg) (a + b) | % Variation** from delivered dose Vs calculated dose |
| 1.2 | 1500 | 150 | 1500 | 0 | 0 | 1500.00 | 0.00 |
| 1.3 | 1625 | 160 | 1600 | 0 | 0 | 1600.00 | −1.54 |
| 1.4 | 1750 | 170 | 1700 | 0 | 0 | 1700.00 | −2.86 |
| 1.5 | 1875 | 190 | 1900 | 0 | 0 | 1900.00 | 1.33 |
| 1.6 | 2000 | 200 | 2000 | 0 | 0 | 2000.00 | 0.00 |
| 1.7 | 2125 | 220 | 2200 | 0 | 0 | 2200.00 | 3.53 |
| 1.8 | 2250 | 220 | 2200 | 0 | 0 | 2200.00 | −2.22 |
| 1.9 | 2375 | 120 | 1200 | 120 | 1200 | 2400.00 | 1.05 |
| 2 | 2500 | 130 | 1300 | 120 | 1200 | 2500.00 | 0.00 |
| 2.1 | 2625 | 130 | 1300 | 130 | 1300 | 2600.00 | −0.95 |
| 2.2 | 2750 | 150 | 1500 | 120 | 1200 | 2700.00 | −1.82 |
| 2.3 | 2875 | 140 | 1400 | 140 | 1400 | 2800.00 | −2.61 |
| 2.4 | 3000 | 150 | 1500 | 150 | 1500 | 3000.00 | 0.00 |
| 2.5 | 3125 | 190 | 1900 | 120 | 1200 | 3100.00 | −0.80 |
| 2.6 | 3250 | 160 | 1600 | 160 | 1600 | 3200.00 | −1.54 |

The containers of the perfusion system of Table (56) may be alphabetically coded as follows:

| First set of Perfusion containers; gemcitabine concentration 10 mg/ml | |
|---|---|
| Volume of perfusion container (ml) | Alphabetical code |
| 120 | B |
| 130 | K |
| 140 | L |
| 150 | C |
| 160 | M |
| 170 | N |
| 190 | O |
| 200 | P |
| 220 | Q |

The perfusion system of Table (56) is accompanied by suitable instructions for example as below:

| BSA (m$^2$) | Instructions |
|---|---|
| 1.2 | Infuse the full volume from one 150 ml container having an alphabetical code C |
| 1.3 | Infuse the full volume from one 160 ml container having an alphabetical code M |
| 1.4 | Infuse the full volume from one 170 ml container having an alphabetical code N |
| 1.5 | Infuse the full volume from one 190 ml container having an alphabetical code O |
| 1.6 | Infuse the full volume from one 200 ml container having an alphabetical code P |
| 1.7 and 1.8 | Infuse the full volume from one 220 ml container having an alphabetical code Q |
| 1.9 | Infuse the full volume from two 120 ml container having an alphabetical code B |
| 2.0 | Connect one 130 ml container having an alphabetical code K + one 120 ml container having an alphabetical code B and infuse the full volume |
| 2.1 | Infuse the full volume from two 130 ml container having an alphabetical code K |
| 2.2 | Connect one 150 ml container having an alphabetical code C + one 120 ml container having an alphabetical code B and infuse the full volume |
| 2.3 | Infuse the full volume from two 140 ml container having an alphabetical code L |
| 2.4 | Infuse the full volume from two 150 ml container having an alphabetical code C |
| 2.5 | Connect one 190 ml container having an alphabetical code O + one 120 ml container having an alphabetical code B and infuse the full volume |
| 2.6 | Infuse the full volume from two 160 ml container having an alphabetical code M |

According to the instructions, one or more perfusion containers can be selected from first, second and/or third set of perfusion containers to deliver the calculated target dose within ±5% of variation.

According to the present invention, the below embodiment provides perfusion system for administration of azacitidine or its pharmaceutically acceptable salt. Table 57 below provides details of the perfusion system having containers of first, second and/or third set with the ranges of concentration and volume of the solution per set.

TABLE 57

| Perfusion system of azacitidine: | | | |
|---|---|---|---|
| | From set of container of the perfusion system | | |
| | First set of perfusion container | Second set of top up perfusion container | Third set of top up perfusion container |
| Concentration range (mg/ml) | 0.07-5.0 | 0.05-0.5 | 0.05-0.5 |
| Preferred concentration range (mg/ml) | 0.5-2.5 | 0.1-0.2 | 0.05-0.07 |
| Volume range (ml) | 50-500 | 50-250 | 50-100 |
| Preferred volume range (ml) | 50-100 | 50-100 | 50-100 |

The perfusion system may comprise one or more perfusion containers in the first set and one or more perfusion containers in the second and/or third set. The containers in different sets according to one preferred embodiment of the present invention are given below in Tables 58-60

TABLE 58

| Perfusion containers of the first set having Azacitidine: | | | | | | | |
|---|---|---|---|---|---|---|---|
| | Perfusion containers of first set | | | | | | |
| Volume of solution in bag (ml) | 60 | 70 | 80 | 90 | 100 | 120 | 200 |
| AZACITIDINE amount per bag (mg) (at a concentration of 0.5 mg/ml) | 30 | 35 | 40 | 45 | 50 | 60 | 100 |
| AZACITIDINE amount per bag (mg) (at a concentration of 1.0 mg/ml) | 60 | 70 | 80 | 90 | 100 | 120 | 200 |
| AZACITIDINE amount per bag (mg) (at a concentration of 1.5 mg/ml) | 90 | 105 | 120 | 135 | 150 | 180 | 300 |
| AZACITIDINE amount per bag (mg) (at a concentration of 2.5 mg/ml) | 150 | 175 | 200 | 225 | 250 | 300 | 500 |

TABLE 59

Perfusion containers of the second set having Azacitidine:

| | Perfusion containers of second set | | | | |
|---|---|---|---|---|---|
| Volume of solution in bag (ml) | 25 | 40 | 50 | 60 | 100 |
| Azacitidine amount per bag (mg) (at a concentration of 0.2 mg/ml) | 5.0 | 8.0 | 10.0 | 12.0 | 20.0 |

TABLE 60

Perfusion containers of the third set having Azacitidine:

| | Perfusion containers of third set | | |
|---|---|---|---|
| Volume of solution in bag (ml) | 20 | 25 | 40 |
| Azacitidine amount per bag (mg) (at a concentration of 0.05 mg/ml) | 1.0 | 1.25 | 2.0 |

In one particularly preferred embodiment wherein the antineoplastic drug is Azacitidine, the first set of infusion containers comprise perfusion solution having Azacitidine at a concentration ranging from about 0.07 mg/ml to 5.0 mg/ml and volume of solution ranging from about 40 ml to about 1000 ml, further wherein the second or third set of infusion containers comprise perfusion solution having Azacitidine at a concentration ranging from about 0.05 mg/ml to 0.5 mg/ml and volume of solution ranging from about 20 ml to about 100 ml.

According to one embodiment, the dose of Azacitidine for a particular indication is 100 mg/m² based on body surface area as the patient parameter. There is provided instructions for calculating the total dose to be delivered to a patient based on the body surface area and instructions for selecting one or more perfusion containers of Azacitidine from different sets, to deliver the calculated dose within ±5% variance and is presented in table (61)

TABLE 61

Description of perfusion system of Azacitidine:

| | | First set of Perfusion container; Azacitidine concentration—2.5 mg/ml | | Second set of Top-up perfusion containers—Azacitidine concentration—0.2 mg/ml | | | |
|---|---|---|---|---|---|---|---|
| BSA (m²) | Total Target Dose to be delivered D (mg) | Volume of perfusion container (ml) | Dose delivered from perfusion container (a) (mg) | Volume of top up container (ml) | Dose delivered from top-up container (b) (mg) | Total dose delivered (mg) (a + b) | % Variation** from delivered dose Vs calculated dose % |
| 1.4 | 140 | 55 | 137.5 | 0 | 0 | 137.5 | −1.8 |
| 1.5 | 150 | 55 | 137.5 | 50 | 10 | 147.5 | −1.7 |
| 1.6 | 160 | 65 | 162.5 | 0 | 0 | 162.5 | 1.6 |
| 1.7 | 170 | 65 | 162.5 | 50 | 10 | 172.5 | 1.5 |
| 1.8 | 180 | 65 | 162.5 | 50 | 10 | 172.5 | −4.2 |
| 1.9 | 190 | 75 | 187.5 | 0 | 0 | 187.5 | −1.3 |
| 2 | 200 | 80 | 200 | 0 | 0 | 200 | 0.0 |
| 2.1 | 210 | 80 | 200 | 50 | 10 | 210 | 0.0 |
| 2.2 | 220 | 80 | 200 | 50 | 10 | 210 | −4.5 |
| 2.3 | 230 | 90 | 225 | 0 | 0 | 225 | −2.2 |
| 2.4 | 240 | 90 | 225 | 50 | 10 | 235 | −2.1 |

**% Variation from delivered dose Vs calculated dose = [((a + b) − D]/D × 100

The containers of the perfusion system of Table (61) may be alphabetically coded as follows:

| First set of Perfusion containers; azacitidine concentration 2.5 mg/ml | | Second set of top-up perfusion containers; azacitidine concentration 0.2 mg/ml | |
|---|---|---|---|
| Volume of perfusion container (ml) | Alphabetical code | Volume of top up container (ml) | Alphabetical code |
| 55 | A | 50 | F |
| 65 | B | | |
| 75 | C | | |
| 80 | D | | |
| 90 | E | | |

The perfusion system of Table (61) is accompanied by suitable instructions for example as below:

| BSA (m$^2$) | Instructions |
|---|---|
| 1.4 | Infuse the full volume from one 55 ml container having an alphabetical code A |
| 1.5 | Connect one 55 ml container having an alphabetical code A with one 50 ml container having an alphabetical code F and Infuse the full volume |
| 1.6 | Infuse the full volume from one 65 ml container having an alphabetical code B |
| 1.8 | Connect one 65 ml container having an alphabetical code B with one 50 ml container having an alphabetical code F and Infuse the full volume |
| 1.9 | Infuse the full volume from one 75 ml container having an alphabetical code C |
| 2.0 | Infuse the full volume from one 80 ml container having an alphabetical code D |
| 2.1 and 2.2 | Connect one 80 ml container having an alphabetical code D with one 50 ml container having an alphabetical code F and Infuse the full volume |
| 2.3 | Infuse the full volume from one 90 ml container having an alphabetical code E |
| 2.4 | Connect one 90 ml container having an alphabetical code E with one 50 ml container having an alphabetical code F and Infuse the full volume |

According to the instructions, one or more perfusion containers can be selected from first, second and/or third set of perfusion containers and full volume is infused to deliver the calculated target dose within ±5% of variation.

According to the present invention, the below embodiment provides perfusion system for administration of arsenic trioxide or its pharmaceutically acceptable salt. Table 62 below provides details of the perfusion system having containers of first, second and/or third set with the ranges of concentration and volume of the solution per set.

TABLE 62

Perfusion system of arsenic trioxide:

| | From set of container of the perfusion system | | |
|---|---|---|---|
| | First set of perfusion container | Second set of top up perfusion container | Third set of top up perfusion container |
| Concentration range (mg/ml) | 0.03-0.2 | 0.03-0.07 | 0.03-0.07 |
| Preferred concentration range (mg/ml) | 0.05-0.1 | 0.03-0.05 | 0.03-0.05 |
| Volume range (ml) | 50-500 | 50-250 | 25-200 |
| Preferred volume range (ml) | 100-250 | 50-100 | 50-100 |

The perfusion system may comprise one or more perfusion containers in the first set and one or more perfusion containers in the second and/or third set. The containers in different sets according to one preferred embodiment of the present invention are given below in Tables 63-65.

TABLE 63

Perfusion containers of the first set having arsenic trioxide:

| | Perfusion containers of first set | | | | | | |
|---|---|---|---|---|---|---|---|
| Volume of solution in bag (ml) | 100 | 110 | 140 | 150 | 190 | 200 | 230 |
| Arsenic trioxide amount per bag (mg) (at a concentration of 0.07 mg/ml) | 7 | 7.7 | 9.8 | 10.5 | 13.3 | 14.0 | 16.1 |

TABLE 64

Perfusion containers of the second set having arsenic trioxide:

| | Perfusion containers of second set | | |
|---|---|---|---|
| Volume of solution in bag (ml) | 50 | 75 | 100 |
| Arsenic trioxide amount per bag (mg) (at a concentration of 0.03 mg/ml) | 1.5 | 2.25 | 3.0 |

TABLE 65

Perfusion containers of the third set having arsenic trioxide:

| | Perfusion containers of third set | |
|---|---|---|
| Volume of solution in bag (ml) | 50 | 80 |
| Arsenic trioxide amount per bag (mg) (at a concentration of 0.02 mg/ml) | 1.0 | 1.6 |

In one particularly preferred embodiment wherein the antineoplastic drug is Arsenic trioxide, the first set of infusion containers comprise perfusion solution having Arsenic trioxide at a concentration ranging from about 0.03 mg/ml to 0.2 mg/ml and volume of solution ranging from about 50 ml to about 500 ml, further wherein the second or third set of infusion containers comprise perfusion solution having Arsenic trioxide at a concentration ranging from about 0.03-0.07 mg/ml and volume of solution ranging from about 20 ml to about 100 ml.

According to one embodiment, the dose of Arsenic trioxide for a particular indication is 0.15 mg/Kg based on body weight as the patient parameter. There is provided instructions for calculating the total dose to be delivered to a patient based on the body surface area and instructions for selecting one or more perfusion containers of Arsenic trioxide from different sets, to deliver the calculated dose within ±5% variance and is presented in table (66):

TABLE 66

Description of perfusion system of Arsenic trioxide:

| | | First set of perfusion container; Arsenic Trioxide concentration—0.07 mg/mL | | Second set of Top-up perfusion containers; Arsenic Trioxide concentration—0.03 mg/mL | | | |
|---|---|---|---|---|---|---|---|
| Body Weight | Total Target Dose to be delivered D (mg) | Volume of perfusion container (ml) | Dose delivered from perfusion container (a) (mg) | Volume of top up container (ml) | Dose delivered from top-up container (b) (mg) | Total Dose delivered a + b (mg) | % Variation** from delivered dose Vs. calculated dose |
| 50 | 7.50 | 110 | 7.7 | 0 | 0 | 7.7 | 2.7 |
| 55 | 8.25 | 100 | 7 | 50 | 1.5 | 8.5 | 3.0 |
| 60 | 9.00 | 110 | 7.7 | 50 | 1.5 | 9.2 | 2.2 |
| 65 | 9.75 | 140 | 9.8 | 0 | 0 | 9.8 | 0.5 |
| 70 | 10.50 | 150 | 10.5 | 0 | 0 | 10.5 | 0.0 |
| 75 | 11.25 | 140 | 9.8 | 50 | 1.5 | 11.3 | 0.4 |
| 80 | 12.00 | 150 | 10.5 | 50 | 1.5 | 12.0 | 0.0 |
| 85 | 12.75 | 190 | 13.3 | 0 | 0 | 13.3 | 4.3 |
| 90 | 13.50 | 190 | 13.3 | 0 | 0 | 13.3 | −1.5 |
| 95 | 14.25 | 190 | 13.3 | 50 | 1.5 | 14.8 | 3.7 |
| 100 | 15.00 | 190 | 13.3 | 50 | 1.5 | 14.8 | −1.3 |
| 105 | 15.75 | 230 | 16.1 | 0 | 0 | 16.1 | 2.2 |
| 110 | 16.50 | 230 | 16.1 | 0 | 0 | 16.1 | −2.4 |
| 115 | 17.25 | 230 | 16.1 | 50 | 1.5 | 17.6 | 2.0 |
| 120 | 18.00 | 230 | 16.1 | 50 | 1.5 | 17.6 | −2.2 |

**% Variation from delivered dose Vs calculated dose = [((a + b) − D]/D × 100

The containers of the perfusion system of Table (66) may be alphabetically coded as follows:

| First set of Perfusion containers; Arsenic Trioxide concentration 0.07 mg/ml | | Second set of top-up perfusion containers; Arsenic Trioxide concentration 0.03 mg/ml | |
|---|---|---|---|
| Volume of perfusion container (ml) | Alphabetical code | Volume of top up container (ml) | Alphabetical code |
| 100 | A | 50 | G |
| 110 | B | | |
| 140 | C | | |
| 150 | D | | |
| 190 | E | | |
| 230 | F | | |

The perfusion system of Table (66) is accompanied by suitable instructions for example as below:

| Body Weight | Instructions |
|---|---|
| 50 | Infuse the full volume from one 110 ml container having an alphabetical code B |
| 55 | Connect one 100 ml container having an alphabetical code A with one 50 ml container having an alphabetical code G and Infuse the full volume |
| 60 | Connect one 110 ml container having an alphabetical code B with one 50 ml container having an alphabetical code G and Infuse the full volume |
| 65 | Infuse the full volume from one 140 ml container having an alphabetical code C |
| 70 | Infuse the full volume from one 150 ml container having an alphabetical code D |
| 75 | Connect one 140 ml container having an alphabetical code C with one 50 ml container having an alphabetical code G and Infuse the full volume |
| 80 | Connect one 150 ml container having an alphabetical code D with one 50 ml container having an alphabetical code G and Infuse the full volume |
| 85 and 90 | Infuse the full volume from one 190 ml container having an alphabetical code E |
| 95 and 100 | Connect one 190 ml container having an alphabetical code E with one 50 ml container having an alphabetical code G and Infuse the full volume |
| 105 and 110 | Infuse the full volume from one 230 ml container having an alphabetical code F |
| 115 and 120 | Connect one 230 ml container having an alphabetical code F with one 50 ml container having an alphabetical code G and Infuse the full volume |

According to the instructions, one or more perfusion containers can be selected from first, second and/or third set of perfusion containers and full volume is infused to deliver the calculated target dose within ±5% of variation.

According to the present invention, the below embodiment provides perfusion system for administration of fluorouracil or its pharmaceutically acceptable salt. Table 67 below provides details of the perfusion system having containers of first, second and/or third set with the ranges of concentration and volume of the solution per set.

TABLE 67

Perfusion system of fluorouracil:

| | From set of container of the perfusion system | | |
|---|---|---|---|
| | First set of perfusion container | Second set of top up perfusion container | Third set of top up perfusion container |
| Concentration range (mg/ml) | 0.50 to 6.0 | 0.1-1.0 | 0.1-1.0 |
| Preferred concentration range (mg/ml) | 0.85 to 2.6 | 1.0 | 0.5 |
| Volume range (ml) | 50-1000 mL | 25-100 mL | 20-100 mL |
| Preferred volume range (ml) | 200-500 mL | 50 mL | 50 mL |

The perfusion system may comprise one or more perfusion containers in the first set and one or more perfusion containers in the second and/or third set. The containers in different sets according to one preferred embodiment of the present invention are given below in Tables 68-70.

TABLE 68

Other Perfusion containers of the first set having 0.85 mg/ml fluorouracil:

| | Perfusion containers of first set | | | | | | |
|---|---|---|---|---|---|---|---|
| Volume of solution in bag (ml) | 200 | 250 | 300 | 350 | 400 | 450 | 500 |
| Fluorouracil amount per bag (mg) (at a concentration of 0.85 mg/ml) | 170 | 212.5 | 255 | 297.5 | 340 | 382.5 | 425 |

TABLE 69

Perfusion containers of the second set having fluorouracil:

| | Perfusion containers of second set | | | |
|---|---|---|---|---|
| Volume of solution in bag (ml) | 25 | 50 | 75 | 100 |
| Fluorouracil amount per bag (mg) (at a concentration of 0.5 mg/ml) | 12.5 | 25 | 37.5 | 50 |

TABLE 70

Perfusion containers of the third set having fluorouracil:

| | Perfusion containers of third set | | | |
|---|---|---|---|---|
| Volume of solution in bag (ml) | 20 | 50 | 75 | 100 |
| Fluorouracil amount per bag (mg) (at a concentration of 0.25 mg/ml) | 5 | 12.5 | 18.75 | 25 |

In one particularly preferred embodiment wherein the antineoplastic drug is Fluorouracil, the first set of infusion containers comprise perfusion solution having Fluorouracil at a concentration ranging from about 0.5 mg/ml to 6.0 mg/ml and volume of solution ranging from about 50 ml to about 1000 ml, further wherein the second or third set of infusion containers comprise perfusion solution having Fluorouracil at a concentration ranging from about 0.1-1.0 mg/ml and volume of solution ranging from about 20 ml to about 100 ml.

According to one embodiment, the dose of Fluorouracil for a particular indication is 5 mg/Kg based on body weight as the patient parameter. There is provided instructions for calculating the total dose to be delivered to a patient based on the body weight and instructions for selecting one or more perfusion containers of Fluorouracil from different sets, to deliver the calculated dose within ±5% variance and is presented in table (71):

TABLE 71

Description of perfusion system of Fluorouracil:

| | | First set of Perfusion container; Fluorouracil concentration 0.85 mg/ml | | Second set of Top-up perfusion container; Fluorouracil concentration 0.5 mg/ml: | | | |
|---|---|---|---|---|---|---|---|
| Body Weight kg | Total Target Dose to be delivered (mg) D | Volume of perfusion container (ml) | Dose delivered from perfusion container (a) (mg) | Volume of top up container (ml) | Dose delivered from top-up container (b) (mg) | Total dose delivered (mg) (a + b) | % Variation** from delivered dose Vs calculated dose |
| 50 | 250 | 300 | 255 | 0 | 0 | 255 | 2.0 |
| 55 | 275 | 300 | 255 | 50 | 25 | 280 | 1.8 |
| 60 | 300 | 300 | 255 | 100 | 50 | 305 | 1.7 |
| 65 | 325 | 400 | 340 | 0 | 0 | 340 | 4.6 |
| 70 | 350 | 400 | 340 | 0 | 0 | 340 | −2.9 |
| 75 | 375 | 400 | 340 | 50 | 25 | 365 | −2.7 |
| 80 | 400 | 400 | 340 | 100 | 50 | 390 | −2.5 |
| 85 | 425 | 500 | 425 | 0 | 0 | 425 | 0.0 |
| 90 | 450 | 500 | 425 | 50 | 25 | 450 | 0.0 |
| 95 | 475 | 500 | 425 | 100 | 50 | 475 | 0.0 |
| 100 | 500 | 600 | 510 | 0 | 0 | 510 | 2.0 |

**% Variation from delivered dose Vs calculated dose = [((a + b) − D]/D × 100

The containers of the perfusion system of Table (71) may be alphabetically coded as follows:

| First set of Perfusion containers; Fluorouracil concentration 0.85 mg/ml | | Second set of top-up perfusion containers; Fluorouracil concentration 0.5 mg/ml | |
|---|---|---|---|
| Volume of perfusion container (ml) | Alphabetical code | Volume of top up container (ml) | Alphabetical code |
| 300 | A | 50 | E |
| 400 | B | 100 | F |
| 500 | C | | |
| 600 | D | | |

The perfusion system of Table (71) is accompanied by suitable instructions for example as below:

| Body Weight | Instructions |
|---|---|
| 50 | Infuse the full volume from one 300 ml container having an alphabetical code A |
| 55 | Connect one 300 ml container having an alphabetical code A with one 50 ml container having an alphabetical code E and Infuse the full volume |
| 60 | Connect one 300 ml container having an alphabetical code A with one 100 ml container having an alphabetical code F and Infuse the full volume |
| 65 and 70 | Infuse the full volume from one 400 ml container having an alphabetical code B |
| 75 | Connect one 400 ml container having an alphabetical code B with one 50 ml container having an alphabetical code E and Infuse the full volume |
| 80 | Connect one 400 ml container having an alphabetical code B with one 100 ml container having an alphabetical code F and Infuse the full volume |
| 85 | Infuse the full volume from one 500 ml container having an alphabetical code C |
| 90 | Connect one 500 ml container having an alphabetical code C with one 50 ml container having an alphabetical code E and Infuse the full volume |
| 95 | Connect one 500 ml container having an alphabetical code C with one 100 ml container having an alphabetical code F and Infuse the full volume |
| 100 | Infuse the full volume from one 600 ml container having an alphabetical code D |

According to the instructions, one or more perfusion containers can be selected from first, second and/or third set of perfusion containers and full volume is infused to deliver the calculated target dose within ±5% of variation.

According to the present invention, the below embodiment provides perfusion system for administration of paclitaxel or its pharmaceutically acceptable salt. Table 72 below provides details of the perfusion system having containers of first, second and/or third set with the ranges of concentration and volume of the solution per set.

TABLE 72

Perfusion system of paclitaxel:

| | From set of container of the perfusion system | | |
|---|---|---|---|
| | First set of perfusion container | Second set of top up perfusion container | Third set of top up perfusion container |
| Concentration range (mg/ml) | 0.1 to 2 | 0.1 to 2 | 0.1 to 2 |
| Preferred concentration range (mg/ml) | 0.3 to 1.2 | 0.3 to 1.2 | 0.3 to 1.2 |
| Volume range (ml) | 40-600 | 50-150 | 50-150 |
| Preferred volume range (ml) | 50-500 | 50-100 | 50-100 |

The perfusion system may comprise one or more perfusion containers in the first set and one or more perfusion containers in the second and/or third set. The containers in different sets according to one preferred embodiment of the present invention are given below in Tables 73-75.

TABLE 73

Perfusion containers of the first set having paclitaxel:

| Volume of solution | Perfusion containers of first set | | | | | | | | |
|---|---|---|---|---|---|---|---|---|---|
| in bag (ml) | 120 | 130 | 140 | 160 | 175 | 205 | 245 | 290 | 350 |
| Paclitaxel amount per bag (mg) (at a concentration of 0.5 mg/ml) | 60 | 65 | 70 | 80 | 87.5 | 102.5 | 122.5 | 145 | 175 |

TABLE 74

Perfusion containers of the second set having paclitaxel:

| | Perfusion containers of second set | | | |
|---|---|---|---|---|
| Volume of solution in bag (ml) | 50 | 75 | 100 | 150 |
| Paclitaxel amount per bag (mg) (at a concentration of 0.4 mg/ml) | 20 | 30 | 40 | 60 |

TABLE 75

Perfusion containers of the third set having paclitaxel:

| | Perfusion containers of third set | | | |
|---|---|---|---|---|
| Volume of solution in bag (ml) | 50 | 75 | 100 | 150 |
| Paclitaxel amount per bag (mg) (at a concentration of 0.25 mg/ml) | 12.5 | 18.75 | 25 | 37.5 |

In one particularly preferred embodiment wherein the antineoplastic drug is Paclitaxel, the first set of infusion containers comprise perfusion solution having Paclitaxel at a concentration ranging from about 0.1 mg/ml to 2.0 mg/ml and volume of solution ranging from about 40 ml to about 600 ml, further wherein the second or third set of infusion containers comprise perfusion solution having Paclitaxel at a concentration ranging from about 0.1-2.0 mg/ml and volume of solution ranging from about 25 ml to about 150 ml.

According to one embodiment, the dose of Paclitaxel for a particular indication is 50 mg/m$^2$ based on body surface area as the patient parameter. There is provided instructions for calculating the total dose to be delivered to a patient based on the body surface area and instructions for selecting one or more perfusion containers of Paclitaxel from different sets, to deliver the calculated dose within ±5% variance and is presented in table (76):

TABLE 76

Description of perfusion system of Paclitaxel:

| | | First set of Perfusion container Paclitaxel concentration 0.5 mg/ml | | Second set of top-up perfusion containers; Paclitaxel concentration 0.4 mg/ml: | | | |
|---|---|---|---|---|---|---|---|
| BSA (m$^2$) | Total Target Dose to be delivered (mg) D | Volume of perfusion container (ml) | Dose delivered from perfusion container (a) (mg) | Volume of top up container (ml) | Dose delivered from top-up container (b) (mg) | Total dose delivered (mg) (a + b) | % Variation** from delivered dose Vs calculated dose |
| 1.4 | 70.0 | 145.0 | 72.5 | 0 | 0.0 | 72.5 | 3.6 |
| 1.5 | 75.0 | 145.0 | 72.5 | 0 | 0.0 | 72.5 | −3.3 |
| 1.6 | 80.0 | 160.0 | 80.0 | 0 | 0.0 | 80.0 | 0.0 |
| 1.7 | 85.0 | 175.0 | 87.5 | 0 | 0.0 | 87.5 | 2.9 |
| 1.8 | 90.0 | 175.0 | 87.5 | 0 | 0.0 | 87.5 | −2.8 |
| 1.9 | 95.0 | 145.0 | 72.5 | 50.0 | 20.0 | 92.5 | −2.6 |
| 2 | 100.0 | 160.0 | 80.0 | 50.0 | 20.0 | 100 | 0 |
| 2.1 | 105.0 | 210.0 | 105.0 | 0 | 0.0 | 105 | 0 |
| 2.2 | 110.0 | 175.0 | 87.5 | 50.0 | 20.0 | 107.5 | 2.3 |
| 2.3 | 115.0 | 200.0 | 100 | 50.0 | 20.0 | 120 | 4.3 |
| 2.4 | 120.0 | 245.0 | 122.5 | 0 | 0.0 | 122.5 | 2.1 |

**% Variation from delivered dose Vs calculated dose = [((a + b) − D]/D × 100

The containers of the perfusion system of Table (76) may be alphabetical coded as follows:

| First set of Perfusion containers; paclitaxel concentration 0.5 mg/ml | | Second set of top-up perfusion containers; paclitaxel concentration 0.4 mg/ml | |
|---|---|---|---|
| Volume of perfusion container (ml) | Alphabetical code | Volume of top up container (ml) | Alphabetical code |
| 145 | A | 50 | G |
| 160 | B | | |
| 175 | C | | |
| 200 | D | | |
| 210 | E | | |
| 245 | F | | |

The perfusion system of Table (76) is accompanied by suitable instructions for example as below:

| BSA (m$^2$) | Instructions |
|---|---|
| 1.4 and 1.5 | Infuse the full volume from one 145 ml container having an alphabetical code A |
| 1.6 | Infuse the full volume from one 160 ml container having an alphabetical code B |
| 1.7 and 1.8 | Infuse the full volume from one 175 ml container having an alphabetical code C |
| 1.9 | Connect one 145 ml container having an alphabetical code A with one 50 ml container having an alphabetical code G and Infuse the full volume |
| 2.0 | Connect one 160 ml container with B with one 50 ml container with G and Infuse the full volume |
| 2.1 | Infuse the full volume from one 210 ml container with E |
| 2.2 | Connect one 175 ml container with C with one 50 ml container with G and Infuse the full volume |
| 2.3 | Connect one 200 ml container with D with one 50 ml container with G and Infuse the full volume |
| 2.4 | Infuse the full volume from one 245 ml container with F |

According to the instructions, one or more perfusion containers can be selected from first, second and/or third set of perfusion containers and full volume is infused to deliver the calculated target dose within ±5% of variation.

According to the present invention, the below embodiment provides perfusion system for administration of cyclophosphamide or its pharmaceutically acceptable salt. Table 77 below provides details of the perfusion system having containers of first, second and/or third set with the ranges of concentration and volume of the solution per set.

TABLE 77

Perfusion system of cyclophosphamide:

| | From set of container of the perfusion system | | |
|---|---|---|---|
| | First set of perfusion container | Second set of top up perfusion container | Third set of top up perfusion container |
| Concentration range (mg/ml) | 5-30 | 1-15 | 1-15 |
| Preferred concentration range (mg/ml) | 15-25 | 5-10 | 1-10 |
| Volume range (ml) | 100-1000 | 30-150 | 30-150 |
| Preferred volume range (ml) | 100-500 | 50-100 | 50-100 |

The perfusion system may comprise one or more perfusion containers in the first set and one or more perfusion containers in the second and/or third set. The containers in different sets according to one preferred embodiment of the present invention are given below in Tables 78-80.

TABLE 78

Perfusion containers of the first set having cyclophosphamide:

| | Perfusion containers of first set | | | | | | | |
|---|---|---|---|---|---|---|---|---|
| Volume of solution in bag (ml) | 100 | 115 | 125 | 135 | 145 | 160 | 175 | 200 |
| Cyclophosphamide amount per bag (mg) (at a concentration of 20 mg/ml) | 2000 | 2300 | 2500 | 2700 | 2900 | 3200 | 3500 | 4000 |

TABLE 79

Perfusion containers of the second set having cyclophosphamide:

| | Perfusion containers of second set | | |
|---|---|---|---|
| Volume of solution in bag (ml) | 75 | 100 | 150 |
| Cyclophosphamide amount per bag (mg) (at a concentration of 10 mg/ml) | 750 | 1000 | 1500 |

TABLE 80

Perfusion containers of the third set having cyclophosphamide:

| | Perfusion containers of third set | | |
|---|---|---|---|
| Volume of solution in bag (ml) | 50 | 75 | 100 |
| Cyclophosphamide amount per bag (mg) (at a concentration of 5 mg/ml) | 250 | 375 | 500 |

In one particularly preferred embodiment wherein the antineoplastic drug is Cyclophosphamide, the first set of infusion containers comprise perfusion solution having Cyclophosphamide at a concentration ranging from about 5 mg/ml to 30 mg/ml and volume of solution ranging from about 100 ml to about 1000 ml, further wherein the second or third set of infusion containers comprise perfusion solution having Cyclophosphamide at a concentration ranging from about 1-15 mg/ml and volume of solution ranging from about 30 ml to about 100 ml.

According to one embodiment, the dose of Cyclophosphamide for a particular indication is 40 mg/kg based on body weight as the patient parameter. There is provided instructions for calculating the total dose to be delivered to a patient based on the body weight and instructions for selecting one or more perfusion containers of Cyclophosphamide from different sets, to deliver the calculated dose within ±5% variance and is presented in table (81):

TABLE 81

Description of perfusion system of Cyclophosphamide:

| Body Weight (Kg) | Total Target Dose to be delivered (mg) D | First set of Perfusion container; cyclophosphamide concentration 20 mg/ml | | Second set of Top-up perfusion containers; cyclophosphamide concentration 10 mg/ml: | | Total dose delivered (mg) (a + b) | % Variation** from delivered dose Vs calculated dose |
|---|---|---|---|---|---|---|---|
| | | Volume of perfusion container (ml) | Dose delivered from perfusion container (a) (mg) | Volume of top up container (ml) | Dose delivered from top-up container (b) (mg) | | |
| 50 | 2000.0 | 100 | 2000.00 | 0 | 0 | 2000.00 | 0.0 |
| 55 | 2200.0 | 105 | 2100.00 | 0 | 0 | 2100.00 | −4.5 |
| 60 | 2400.0 | 115 | 2300.00 | 0 | 0 | 2300.00 | −4.2 |
| 65 | 2600.0 | 125 | 2500.00 | 0 | 0 | 2500.00 | −3.8 |
| 70 | 2800.0 | 135 | 2700.00 | 0 | 0 | 2700.00 | −3.6 |
| 75 | 3000.0 | 145 | 2900.00 | 0 | 0 | 2900.00 | −3.3 |
| 80 | 3200.0 | 160 | 3200.00 | 0 | 0 | 3200.00 | 0.0 |
| 85 | 3400.0 | 115 | 2300.00 | 100 | 1000 | 3300.00 | −2.9 |
| 90 | 3600.0 | 135 | 2700.00 | 100 | 1000 | 3700.00 | 2.8 |
| 95 | 3800.0 | 135 | 2700.00 | 100 | 1000 | 3700.00 | −2.6 |
| 100 | 4000.0 | 145 | 2900.00 | 100 | 1000 | 3900.00 | −2.5 |

**% Variation from delivered dose Vs calculated dose = [((a + b) − D]/D × 100

The containers of the perfusion system of Table (81) may be alphabetical coded as follows:

| First set of Perfusion containers; cyclophosphamide concentration 0.85 mg/ml | | Second set of top-up perfusion containers; cyclophosphamide concentration 0.5 mg/ml | |
|---|---|---|---|
| Volume of perfusion container (ml) | Alphabetical code | Volume of top up container (ml) | Alphabetical code |
| 100 | A | 100 | H |
| 105 | B | | |
| 115 | C | | |
| 125 | D | | |
| 135 | E | | |
| 145 | F | | |
| 160 | G | | |

The perfusion system of Table (81) is accompanied by suitable instructions for example as below:

| Body Weight | Instructions |
|---|---|
| 50 | Infuse the full volume from one 100 ml container having an alphabetical code A |
| 55 | Infuse the full volume from one 105 ml container having an alphabetical code B |
| 60 | Infuse the full volume from one 115 ml container having an alphabetical code C |
| 65 | Infuse the full volume from one 125 ml container having an alphabetical code D |
| 70 | Infuse the full volume from one 135 ml container having an alphabetical code E |
| 75 | Infuse the full volume from one 145 ml container having an alphabetical code F |
| 80 | Infuse the full volume from one 160 ml container having an alphabetical code G |
| 85 | Connect one 115 ml container having an alphabetical code C with one 100 ml container having an alphabetical code H and Infuse the full volume |
| 90 and 95 | Connect one 135 ml container having an alphabetical code E with one 100 ml container having an alphabetical code A and Infuse the full volume |
| 100 | Connect one 145 ml container having an alphabetical code F with one 100 ml container having an alphabetical code H and Infuse the full volume |

According to the instructions, one or more perfusion containers can be selected from first, second and/or third set of perfusion containers and full volume is infused to deliver the calculated target dose within ±5% of variation.

The invention claimed is:

1. A perfusion system for direct administration of a dose of irinotecan or a pharmaceutically acceptable salt thereof to any patient in a patient population in need thereof, the dose calculated according to a patient parameter, wherein the parameter varies over a range in the patient population, said system comprising:
   a plurality of perfusion containers comprising:
      a first set of perfusion containers consisting essentially of a first ready-to-infuse, aqueous perfusion solution of irinotecan or a pharmaceutically acceptable salt thereof at a first concentration, each perfusion container of the first set having only one outlet for withdrawal of the aqueous perfusion solution therefrom during direct administration to a patient; and
      a second set of top-up perfusion containers, each top-up perfusion container of the second set consisting essentially of a second ready-to-infuse, aqueous perfusion solution of irinotecan or a pharmaceutically acceptable salt thereof at a second concentration, each top-up perfusion container of the second set having only one outlet for withdrawal of the aqueous perfusion solution therefrom during direct administration to a patient; and
   instructions for selecting one or more containers from the first set of perfusion containers and, if required, one or more top-up perfusion containers from the second set for directly administering a dose of irinotecan or a pharmaceutically acceptable salt thereof to a patient from the patient population based upon the calculated dose for the patient, wherein
   the perfusion system is to be used on any patient in the patient population regardless of the calculated dose, and
   the aqueous perfusion solutions contained within the plurality of perfusion containers are to be directly administered to the patient without any manipulation of the aqueous perfusion solutions prior to said administration.

2. The perfusion system of claim 1, wherein the number of containers per the first set and/or the second set is 1-4.

3. The perfusion system of claim 1, wherein the first concentration and the second concentration are different.

4. The perfusion system of claim 1, wherein the first concentration and the second concentration are the same.

5. The perfusion system of claim 1, wherein the first set of perfusion containers include a plurality of containers having at least two different volumetric amounts of the ready-to-infuse, aqueous perfusion solution.

6. The perfusion system of claim 1, wherein the patient parameter is selected from body surface area, body-weight, renal function and hepatic function.

7. The perfusion system of claim 1, wherein the instructions provide for selecting the one or more containers for directly administering the dose of irinotecan or a pharmaceutically acceptable salt thereof to any patient from the patient population in an amount equal to or less than ±5% of the calculated dose.

8. The perfusion system of claim 1, wherein the instructions provide for selecting the one or more containers for directly administering the dose of irinotecan or a pharmaceutically acceptable salt thereof to any patient from the patient population in an amount equal to or less than ±3% of the calculated dose.

9. The perfusion system of claim 1, wherein each of the first set of perfusion containers has an aqueous perfusion solution volume ranging from 80 to 500 ml, and the first concentration ranges from 1.0 to 3.0 mg/ml.

10. The perfusion system of claim 1, wherein
   each of the first set of perfusion containers has an aqueous perfusion solution volume ranging from 90 to 300 ml, and the first concentration ranges from 1.5 to 2.0 mg/ml.

11. The perfusion system of claim 1, wherein
   each of the first set of perfusion containers has an aqueous perfusion solution volume ranging from 80 to 500 ml, and the first concentration ranges from 1.0 to 3.0 mg/ml, and
   each of the second set of top-up perfusion containers has an aqueous perfusion solution volume ranging from 50 to 350 ml, and the second concentration ranges from 0.1 to 0.8 mg/ml.

12. The perfusion system of claim 1, wherein
   each of the first set of perfusion containers has an aqueous perfusion solution volume ranging from 90 to 300 ml, and the first concentration ranges from 1.5 to 2.0 mg/ml, and each of the second set of top-up perfusion containers has an aqueous perfusion solution volume ranging from 75 to 150 ml, and the second concentration ranges from 0.2 to 0.4 mg/ml.

13. The perfusion system of claim 1, wherein:

the plurality of perfusion containers further comprises a third set of top-up perfusion containers, each top-up perfusion container of the third set consisting essentially of a third ready-to-infuse, aqueous perfusion solution of irinotecan or a pharmaceutically acceptable salt thereof at a third concentration, each top-up perfusion container of the third set having only one outlet for withdrawal of the aqueous perfusion solution therefrom during direct administration to a patient; and the instructions further comprise instructions for selecting, if required, one or more top-up perfusion containers from the third set for directly administering the calculated dose of irinotecan or a pharmaceutically acceptable salt thereof from the selected perfusion containers.

14. The perfusion system of claim 13, wherein each of the perfusion containers in the first set of perfusion containers consists essentially of a first volume of the aqueous perfusion solution;

each of the perfusion containers in the second set of top-up perfusion containers consists essentially of a second volume of the aqueous perfusion solution; and each of the perfusion containers in the third set of top-up perfusion containers consists essentially of a third volume of the aqueous perfusion solution, wherein at least two of first volume, the second volume, and the third volume are different.

15. The perfusion system of claim 14, wherein at least two of the first concentration, the second concentration, and the third concentration are different.

16. The perfusion system of claim 14, wherein at least two of the first concentration, the second concentration, and the third concentration are the same.

17. The perfusion system of claim 13, wherein each of the perfusion containers in the first set of perfusion containers consists essentially of a first volume of the aqueous perfusion solution;

each of the perfusion containers in the second set of top-up perfusion containers consists essentially of a second volume of the aqueous perfusion solution; and each of the perfusion containers in the third set of top-up perfusion containers consists essentially of a third volume of the aqueous perfusion solution, wherein at least two of first volume, the second volume, and the third volume are the same.

18. The perfusion system of claim 17, wherein at least two of the first concentration, the second concentration, and the third concentration are different.

19. The perfusion system of claim 17, wherein at least two of the first concentration, the second concentration, and the third concentration are the same.

20. The perfusion system of claim 13, wherein each of the first set of perfusion containers has an aqueous perfusion solution volume ranging from 80 to 500 ml, and the first concentration ranges from 1.0 to 3.0 mg/ml, each of the second set of top-up perfusion containers has an aqueous perfusion solution volume ranging from 50 to 350 ml, and the second concentration ranges from 0.1 to 0.8 mg/ml, and each of the third set of top-up perfusion containers has an aqueous perfusion solution volume ranging from 50 to 350 ml, and the third concentration ranges from 0.1 to 0.8 mg/ml.

* * * * *